(12) United States Patent
Sugiura et al.

(10) Patent No.: US 8,828,565 B2
(45) Date of Patent: Sep. 9, 2014

(54) LUBRICANT COMPOSITION, FLUORINE-BASED COMPOUND, AND USE THEREOF

(75) Inventors: Hiroki Sugiura, Minami-ashigara (JP); Masayuki Harada, Minami-ashigara (JP); Ken Kawata, Minami-ashigara (JP); Akiko Hattori, Minami-ashigara (JP); Atsushi Tatsugawa, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 63 days.

(21) Appl. No.: 13/414,042

(22) Filed: Mar. 7, 2012

(65) Prior Publication Data

US 2012/0231297 A1    Sep. 13, 2012

(30) Foreign Application Priority Data

Mar. 7, 2011   (JP) ................. 2011-048763

(51) Int. Cl.
*G11B 5/33*        (2006.01)
*C07C 43/225*      (2006.01)
(Continued)

(52) U.S. Cl.
CPC .............. *G11B 5/725* (2013.01); *C07D 257/02* (2013.01); *C10M 2215/221* (2013.01); *C07D 251/54* (2013.01); *C10M 105/70* (2013.01); *C10M 2207/0235* (2013.01); *C10M 2213/0606* (2013.01); *C10N 2230/06* (2013.01); *C10M 2215/222* (2013.01); *C10N 2240/204* (2013.01); *C07D 251/30* (2013.01); *C10M 107/38* (2013.01); *C10M 105/68* (2013.01); *C10M 105/16* (2013.01); *C07C 43/23* (2013.01); *C10N 2250/121* (2013.01)

USPC ........ 428/814; 428/421; 428/835.8; 544/199; 544/221; 568/655; 540/474

(58) Field of Classification Search
None
See application file for complete search history.

(56) References Cited

U.S. PATENT DOCUMENTS 5,374,480 A * 12/1994 Nishikawa et al. ........... 428/336
5,456,980 A * 10/1995 Murakami et al. ........... 428/336
(Continued)

FOREIGN PATENT DOCUMENTS

| EP | 1 219 629 A1 | 7/2002 |
| EP | 1 295 934    | 3/2003 |

(Continued)

OTHER PUBLICATIONS

Derwent Abstract Translation of WO2010109851 A1 (published Sep. 2010).*

(Continued)

*Primary Examiner* — Kevin Bernatz
(74) *Attorney, Agent, or Firm* — Sughrue Mion, PLLC

(57) ABSTRACT

Disclosed is a lubricant composition comprising at least one kind of compound represented by following formula (1):

$$X \!-\! [\!-\! Y \!-\! [\!\{(CF_2)_{p1}(CF)_{p2}[CF(CF_3)]_{p3}[C(CF_3)_2]_{p4}O\}_q \!-\! C_nF_{2n+1}]_s]_t \quad (1)$$

where X represents a cyclic group that may be substituted; Y represents a divalent or higher-valent linking group having at least one polar group and having no aromatic cyclic group; p1 represents an integer of 1 to 4; p2, p3, and p4 each represent an integer of 0 to 4; q represents an integer of 0 to 30; n represents an integer of 1 to 10; s represents an integer of 1 to 4; and t represents an integer of 2 to 10.

35 Claims, 1 Drawing Sheet

(51) Int. Cl.
  *B32B 27/00* (2006.01)
  *C07D 257/02* (2006.01)
  *C07D 251/54* (2006.01)
  *C10M 105/70* (2006.01)
  *G11B 5/725* (2006.01)
  *C07D 251/30* (2006.01)
  *C10M 107/38* (2006.01)
  *C10M 105/68* (2006.01)
  *C10M 105/16* (2006.01)
  *C07C 43/23* (2006.01)

(56) References Cited

U.S. PATENT DOCUMENTS

| | | | |
|---|---|---|---|
| 5,536,578 A * | 7/1996 | Shoji et al. | 428/408 |
| 5,663,127 A * | 9/1997 | Flynn et al. | 508/250 |
| 6,608,009 B2 | 8/2003 | Akada et al. | |
| 8,492,011 B2 * | 7/2013 | Itoh et al. | 428/835.8 |
| 2002/0183211 A1 | 12/2002 | Akada et al. | |
| 2003/0138670 A1 * | 7/2003 | Liu et al. | 428/695 |
| 2003/0207774 A1 | 11/2003 | Negoro et al. | |
| 2006/0052262 A1 | 3/2006 | Akada et al. | |
| 2008/0194441 A1 | 8/2008 | Kawata et al. | |
| 2009/0143262 A1 | 6/2009 | Kawata | |
| 2011/0015107 A1 * | 1/2011 | Marchionni et al. | 508/465 |
| 2011/0026162 A1 | 2/2011 | Hamakubo et al. | |
| 2012/0021253 A1 * | 1/2012 | Nakata et al. | 428/810 |

FOREIGN PATENT DOCUMENTS

| | | |
|---|---|---|
| JP | 1-246237 A | 10/1989 |
| JP | 4-19816 A | 1/1993 |
| JP | 6-157471 A | 6/1994 |
| JP | 7-228575 A | 8/1995 |
| JP | 10-143838 A | 5/1998 |
| JP | 2001-174622 A | 7/2001 |
| JP | 2002-69472 A | 3/2002 |
| JP | 2003-192677 A | 7/2003 |
| JP | 2004-352999 A | 12/2004 |
| JP | 2006-257382 A | 9/2006 |
| JP | 2006-307201 A | 11/2006 |
| JP | 2006-307202 A | 11/2006 |
| JP | 2007-92055 A | 4/2007 |
| JP | 2008-195799 A | 8/2008 |
| JP | 2008-214603 A | 9/2008 |
| JP | 2010-143855 A | 7/2010 |
| JP | 2010-248463 A | 11/2012 |
| WO | 01/21630 A1 | 3/2001 |
| WO | 2004/031261 A | 4/2004 |
| WO | 2008/096875 A1 | 8/2008 |
| WO | 2009/123037 A1 | 10/2009 |
| WO | 2010/109851 A1 | 9/2010 |

OTHER PUBLICATIONS

Ken Kawata, "Orientation Control and Fixation of Discotic Liquid Crystal", The Chemical Record, The Japan Chemical Journal Forum and Wiley Periodicals, Inc., 2002, pp. 59-80, vol. 2.
Office Action dated Nov. 19, 2013 in Japanese Application No. 2009-216679.
Office Action dated Sep. 10, 2013 in Japanese Application No. 2011-048763.
Paul H. Kasai, et al., Degradation of perfluoropolyethers catalyzed by aluminum oxide, *Applied Surface Science* (1991), pp. 201-211, vol. 51.
Extended European Search Report dated Sep. 3, 2012 in European Patent Application No. 10755653.2.
English translation of International Preliminary Report on Patentability dated Oct. 27, 2011 in PCT/JP2010/002055.
International Preliminary Report on Patentability dated Oct. 6, 2011 in PCT/JP2010/002055.

* cited by examiner

| 6 Lubricating Layer |
|---|
| 5 Protective Layer |
| 4 Magnetic Recording Layer |
| 3 Intermediate Layer |
| 2 Soft Magnetic Layer |
| 1 Substrate |

LUBRICANT COMPOSITION, FLUORINE-BASED COMPOUND, AND USE THEREOF

CROSS-REFERENCE TO RELATED APPLICATIONS

The present application claims the benefit of priority from Japanese Patent Application No. 2011-048763, filed on Mar. 7, 2011, the contents of which are herein incorporated by reference in their entirety.

BACKGROUND OF THE INVENTION

1. Field of the Invention

The present invention relates to a fluorine-based compound containing a polar group and a pertluoroalkylene group, and a lubricant composition including the same. More specifically, the present invention relates to a lubricant composition which is useful as a lubricant for a recording medium such as a magnetic disk, a magnetic tape, and the like as a mass-storage recording medium. In addition, the present invention relates to various uses of the lubricant composition, and specifically to a film and a laminate having the film, a magnetic recording medium, a head slider, and a magnetic recording device, each of which is formed using the lubricant composition.

2. Background Art

A thin film type magnetic recording medium is produced by forming a magnetic layer formed of a ferromagnetic metal or an alloy thereof on a nonmagnetic substrate by means of various methods (for example, a sputtering method, a vapor deposition method, a non-electrolytic plating method, and the like). When the magnetic recording medium is practically used, it is brought into contact with a magnetic head at a high speed, so the medium suffers from abrasion damage or is caused to have deterioration in the magnetic characteristics in some cases. Accordingly, a protective film and a lubricating layer are provided on the magnetic layer so as to improve the abrasion resistance. A carbonaceous film has been generally used as a material of the protective film layer. In addition, a fluorine-based compound is generally used as a material of the lubricating layer.

In this way, the lubricating layer of the recording medium is very useful for the purpose of reducing the abrasion damage and the deterioration of magnetic characteristics caused by the contact that occurs between the head and the medium, by means of reducing a coefficient of kinetic friction. On the other hand, particularly, when the film thickness of the lubricating layer is large, the head floating becomes unstable due to attachment of the lubricating layer to a head or interaction between the lubricant and the head, and thus, there is a concern about occurrence of errors during the read-write or a crash with a disk. On the other hand, if the film thickness of the lubricating layer is reduced, the above phenomenon does not easily occur, but the function of the lubricating layer, that is, the suppression of the abrasion damage and deterioration of the magnetic characteristics caused by the contact between the head and the disk cannot be accomplished in some cases. In order to increase the surface recording density, it is required to keep the floating height of the head low and speed up the disk rotation, and thus, it is important to maintain the function of the lubricating layer.

Accordingly, various attempts for solving the above problem by carefully selecting a lubricant that is used for the lubricating layer have been made. In JP-A-2010-248463 discloses a fluorine-based compound having a predetermined structure containing a cyclic group, a polar group directly bonded to an aromatic ring, and a fluorine-based chain, and a lubricant composition including the same, but the adsorptive force with respect to a substrate and the shape of a coated surface are not always satisfactory. Accordingly, a further improvement in this is demanded.

Furthermore, various lubricant compositions using a polymer that includes a mesogen structure in a main chain or a side chain, and grease compositions have been proposed (for example, JP-A-2006-307202 and JP-A-2008-195799), but whether these compositions are useful as materials used for the lubricating layer for a recording medium has not been clarified.

SUMMARY OF THE INVENTION

The lubricant composition disclosed in JP-A-2010-248463 is excellent as a material of a lubricating layer of a recording medium, but there is a demand for further improvement in terms of the solubility in a solvent, the shape of the coated surface, and the adsorption performance with respect to a base material.

It is an object of the present invention to provide a lubricant composition having a further improvement in the characteristics required for a lubricant, particularly, the characteristics required for a lubricant for a recording medium.

It is another object of the present invention to provide a lubricant composition having a further improvement, particularly, in view of the solubility in a solvent, the shape of the coated surface, and the adsorption performance with respect to a base material.

It is a still another object of the present invention to provide various uses of the lubricant composition, and provide a film and a laminate having the film, a magnetic recording medium, a head slider, and a magnetic recording device, which are produced using the composition.

It is a yet still another object of the present invention to provide a novel fluorine-based compound that is useful in various uses, for example, as a lubricant.

Means for Solving the Problem

In order to solve the above problems, the present inventors have made an extensive investigation, and as a result, they have found that the structure of a linking group between a cyclic group and a perfluoroalkylene group, which has a polar group, has an effect on the lubricating performance. That is, the present inventors have also found that the lubricating performance is improved when the linking group has a flexible structure not containing an aromatic cyclic group, thereby completing the present invention.

The means for achieving the above-described objects are as follows.

<1> A lubricant composition comprising at least one kind of compound represented by following formula (1):

$$X\!-\!\!\left[Y\!-\!\!\left[\{(CF_2)_{p1}(CF)_{p2}[CF(CF_3)]_{p3}[C(CF_3)_2]_{p4}O\}_q\!-\!C_nF_{2n+1}\right]_s\right]_t \quad (1)$$

where X represents a cyclic group that may be substituted; Y represents a divalent or higher-valent linking group having at least one polar group and having no aromatic cyclic group; p1 represents an integer of 1 to 4; p2, p3, and p4 each represent an integer of 0 to 4; q represents an integer of 0 to 30; n represents an integer of 1 to 10; s represents an integer of 1 to 4; and t represents an integer of 2 to 10, provided that the binding sequence of $-(CF_2)_{p1}-$, $-(CF)_{p2}-$, $-[CF(CF_3)]_{p3}-$, and $-[C(CF_3)_2]_{p4}-$ that constitute $-\{(CF_2)_{p1}(CF)_{p2}[CF(CF_3)]_{p3}[C(CF_3)_2]_{p4}O\}-$ in formula (1) is not limited, and $-\{(CF_2)_{p1}(CF)_{p2}[CF(CF_3)]_{p3}[C(CF_3)_2]_{p4}O\}-$ means a perfluoroalkyleneoxy group in which a perfluoroalkylene unit selected from $-(CF_2)_{p1}-$, $-(CF)_{p2}-$, $-[CF(CF_3)]_{p3}-$, and $-[C(CF_3)_2]_{p4}-$ and an oxygen atom are distributed randomly; when q is 2 or more, a plurality of $-\{(CF_2)_{p1}(CF)_{p2}[CF(CF_3)]_{p3}[C(CF_3)_2]_{p4}O\}-$ may be the same as or different from each other; when s is 2 or more, a plurality of n's and q's may be the same as or different from each other; and when t is 2 or more, a plurality of s's and Y's may be the same as or different from each other; and when p2 is 1 or more, the perfluoroalkyleneoxy group has a branched structure.

<2> The lubricant composition according to <1>, wherein the fluorine content per molecule of the compound is 37% by mass or more and 76% by mass or less.

<3> The lubricant composition according to <1> or <2>, wherein X is an aromatic cyclic group or non-aromatic cyclic group, which may be substituted.

<4> The lubricant composition according to any one of <1> to <3>, wherein the polar group contained in Y is a polar group selected from a group consisting of a hydroxyl group, an amino group, a mercapto group, a carboxyl group, a carbamoyl group, a sulfonamide group, a phosphoric acid group, and a phosphate group.

<5> The lubricant composition according to any one of <1> to <4>, wherein the polar group contained in Y is a hydroxyl group.

<6> The lubricant composition according to any one of <1> to <5>, wherein Y is a linking group, which contains a $C_2$ to $C_{10}$ alkylene group, provided that one carbon atom or two or more carbon atoms that are not adjacent to each other in the alkylene group may be substituted with an oxygen atom, a nitrogen atom, a sulfur atom, or a carbonyl group (C=O), and further, a polar group is bonded to any carbon atom in the alkylene group or to a nitrogen atom in the case where the carbon atom is substituted with a nitrogen atom directly or via a $C_1$ to $C_5$ alkylene group.

<7> The lubricant composition according to any one of <1> to <6>, wherein Y contains a partial structure represented by the following formula:

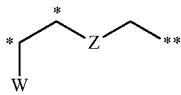

where W represents a polar group, Z represents an oxygen atom, a sulfur atom, or a nitrogen atom; any one of carbon atoms marked with * or Z in the case where Z is a nitrogen atom is bonded to X directly or via a $C_1$ to $C_8$ alkylene group (provided that one carbon atom or two or more carbon atoms that are not adjacent to each other in the alkylene group may be substituted with an oxygen atom, a nitrogen atom, a sulfur atom, or a carbonyl group (C=O)); and a carbon atom marked with ** is bonded to $-\{(CF_2)_{p1}(CF)_{p2}[CF(CF_3)]_{p3}[C(CF_3)_2]_{p4}O\}_q-C_nF_{2n+1}$.

<8> The lubricant composition according to any one of <1> to <7>, wherein Y is a group represented by any of the following formulae (Y1) to (Y3):

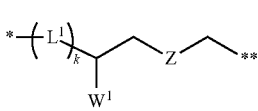
(Y1)

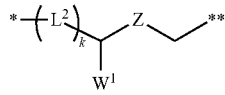
(Y2)

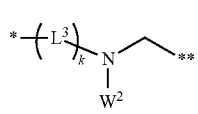
(Y3)

where $W^1$ and $W^2$ each represent a polar group, or a group having a polar group including one or more polar groups, one or more methylene groups ($CH_2$), one or more methine groups (CH), one or more quaternary carbon atoms, or a group formed by combination of two or more thereof; k represents 0 or 1; $L^1$ to $L^3$ each represent $-CH_2-$, $-OCH_2-$, $-CH_2O-$, or $-C(=O)-$; Z represents an oxygen atom or NH; and * and ** each represent binding positions with X and $-\{(CF_2)_{p1}(CF)_{p2}[CF(CF_3)]_{p3}[C(CF_3)_2]_{p4}O\}_q-C_nF_{2n+1}$, respectively.

<9> The lubricant composition according to any one of <1> to <8>, wherein the perfluoroalkyleneoxy group in the formula (1) is a group represented by the following formula (2a) or (2b):

(2a)

(2b)

where, in formulae (2a) and (2b), m represents an integer of 2 to 4, q represents an integer of 1 to 30, a plurality of m's in the case where q in the formula (2a) is 2 or more, and a plurality of m's in the formula (2b) may be the same as or different from each other, * represents a binding position with Y, and ** represents a binding position with $C_nF_{2n+1}$.

<10> The lubricant composition according to any one of <1> to <9>, wherein the perfluoroalkyleneoxy group in the formula (1) is a group represented by the following formula (3a) or (3b):

(3a)

(3b)

in the formulae (3a) and (3b), v represents an integer of 1 to 20 and w represents an integer of 1 to 20, provided that (v+w) is an integer of 1 to 30; the binding sequence of ($CF_2O$) and ($CF_2CF_2O$) is not limited, * represents a binding position with Y, and ** represents a binding position with $C_nF_{2n+1}$.

<11> The lubricant composition according to any one of <1> to <10>, wherein at least one kind of compound represented by the formula (1) is a compound represented by any of the following formulae (1a) to (1f):

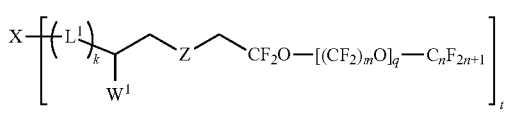
(1a)

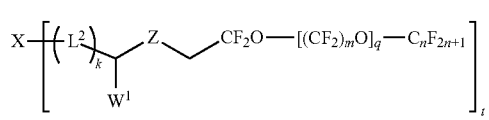
(1b)

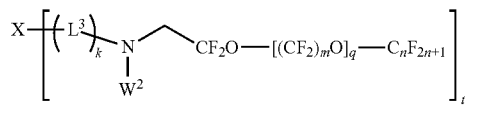
(1c)

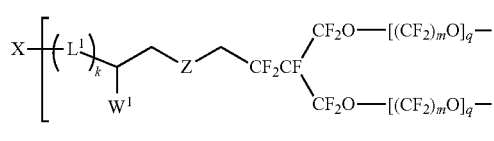
(1d)

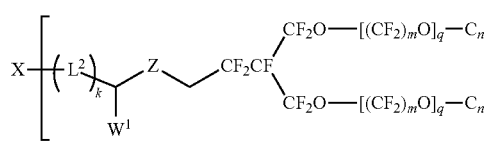
(1e)

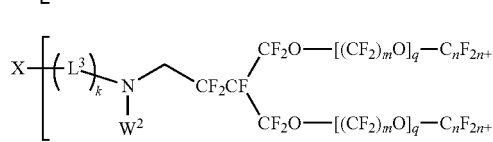
(1f)

where in the formulae, X represents a cyclic group which may be substituted; $W^1$ and $W^2$ each represent a polar group, or a group having a polar group including one or more polar groups, one or more methylene groups ($CH_2$), one or more methine groups (CH), one or more quaternary carbon atoms, or a group formed by combination of two or more thereof; k represents 0 or 1; $L^1$ to $L^3$ each represent —$CH_2$—, —$OCH_2$—, —$CH_2O$—, or —C(=O)—; Z represents an oxygen atom or NH; m represents an integer of 2 to 4; n represents an integer of 1 to 10; t represents an integer of 2 to 10; and q represents an integer of 1 to 30, provided that a plurality of $L^1$ to $L^3$, k, $W^1$, $W^2$, Z, m, n, and q each present in the formula may be the same as or different from each other.

<12> The lubricant composition according to any one of <1> to <10>, wherein at least one kind of compound represented by the formula (1) is a compound represented by any of the following formulae (1g) to (1l):

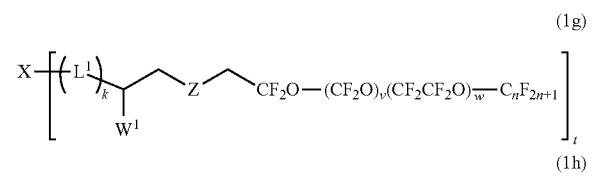

(1g)

(1h)

(1i)

(1j)

(1k)

(1l)

where, in the formulae, X represents a cyclic group which may be substituted; $W^1$ and $W^2$ each represent a polar group, or a group having a polar group including one or more polar groups, one or more methylene groups ($CH_2$), one or more methine groups (CH), one or more quaternary carbon atoms, or a group formed by combination of two or more thereof; k represents 0 or 1; $L^1$ to $L^3$ each represent —$CH_2$—, —$OCH_2$—, —$CH_2O$—, or —C(=O)—; Z represents an oxygen atom or NH; v represents an integer of 1 to 20; and w represents an integer of 1 to 20, provided that (v+w) is an integer of 1 to 30; the binding sequence of ($CF_2O$) and ($CF_2CF_2O$) is not limited; n represents an integer of 1 to 10; and t represents an integer of 2 to 10, provided that a plurality of $L^1$ to $L^3$, k, $W^1$, $W^2$, Z, v, w, and n each present in the formula may be the same as or different from each other.

<13> The lubricant composition according to any one of <1> to <12>, wherein the lubricant composition is used as a lubricant of a disk for a magnetic recording medium.

<14> A film comprising the lubricant composition according to any one of <1> to <13>.

<15> The film according to <14>, wherein the film is formed by a dip coating method, a spin coating method, or a vacuum-deposition method.

<16> A laminate comprising:
a substrate having carbon as a main raw material on at least a part of the surface; and
the film according to <14> or <15> on the substrate.

<17> The laminate according to <16>, wherein the laminate is formed by carrying out an ultraviolet ray irradiation treatment or a heat treatment for adherence onto the substrate.

<18> A magnetic recording medium comprising at least:
a magnetic layer and
the film according to <14> or <15>.

<19> The magnetic recording medium according to <18>, comprising a protective layer between the magnetic layer and the film.

<20> A head slider provided with a magnetic head, comprising the film according to <14> or <15> on at least a part of the surface.

<21> A magnetic recording device comprising at least one of the magnetic recording medium according to <18> or <19> and the head slider according to <20>.

<22> A fluorine-based compound represented by following formula (1):

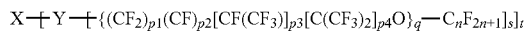

where X represents a cyclic group which may be substituted; Y represents a divalent or higher-valent linking group having at least one polar group and having no aromatic cyclic group; p1 represents an integer of 1 to 4; p2, p3, and p4 each represent an integer of 0 to 4; q represents an integer of 0 to 30; n represents an integer of 1 to 10; s represents an integer of 1 to 4; and t represents an integer of 2 to 10, provided that the binding sequence of $—(CF_2)_{p1}—$, $—(CF)_{p2}—$, $—[CF(CF_3)]_{p3}—$, and $—[C(CF_3)_2]_{p4}—$ that constitute $—\{(CF_2)_{p1}(CF)_{p2}[CF(CF_3)]_{p3}[C(CF_3)_2]_{p4}O\}—$ in the formula (1) is not limited, and $—\{(CF_2)_{p1}(CF)_{p2}[CF(CF_3)]_{p3}[C(CF_3)_2]_{p4}O\}—$ means a perfluoroalkyleneoxy group in which a perfluoroalkylene unit selected from $—(CF_2)_{p1}—$, $—(CF)_{p2}—$, $—[CF(CF_3)]_{p3}—$, and $—[C(CF_3)_2]_{p4}—$ and an oxygen atom are distributed randomly; when q is 2 or more, a plurality of $—\{(CF_2)_{p1}(CF)_{p2}[CF(CF_3)]_{p3}[C(CF_3)_2]_{p4}O\}—$ may be the same as or different from each other; when s is 2 or more, a plurality of n's and q's may be the same as or different from each other; and when t is 2 or more, a plurality of s's and Y's may be the same as or different from each other; and when p2 is 1 or more, the perfluoroalkyleneoxy group has a branched structure.

<23> The fluorine-based compound according to <22>, wherein the fluorine content per molecule is 37% by mass or more and 76% by mass or less.

<24> The fluorine-based compound according to <22> or <23>, wherein X is a group selected from a group consisting of benzene, cyclohexane, triazine, isocyanurate, pyrimidine, and 1,4,7,10-tetraazacyclododecane, which may be substituted.

<25> The fluorine-based compound according to <22> or <23>, wherein X is a cyclic group of any of the following formulae (X1) to (X4):

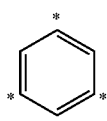

(X1)

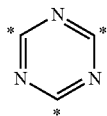

(X2)

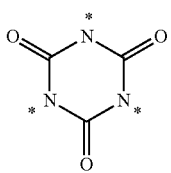

(X3)

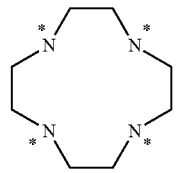

(X4)

where, in the formula, * represents a position at which Y can be bonded, and Y's are bonded to two or more * positions of the respective formulae, and other substituents may be bonded at the * position at which Y is not bonded or at the other positions at which Y can be bonded.

<26> The fluorine-based compound according to any one of <22> to <25>, wherein Y in the formula (1) is a linear or branched divalent to pentavalent linking group having 1 to 15 carbon atoms, having at least one atom or atom group selected from a group consisting of an ether-based oxygen atom, an amine-based nitrogen atom, and an amide bond.

<27> The fluorine-based compound according to any one of <22> to <26>, wherein Y is a linking group, which contains a $C_2$ to $C_{10}$ alkylene group, provided that one carbon atom or two or more carbon atoms that are not adjacent to each other in the alkylene group may be substituted with an oxygen atom, a nitrogen atom, a sulfur atom, or a carbonyl group ($—(C=O)—$), and further, a polar group is bonded to any carbon atom in the alkylene group or to a nitrogen atom in the case where the carbon atom is substituted with a nitrogen atom directly or via a $C_1$ to $C_5$ alkylene group.

<28> The fluorine-based compound according to any one of <22> to <27>, wherein Y contains a partial structure represented by the following formula:

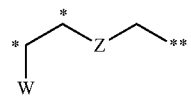

where, in the formula, W represents a polar group, Z represents an oxygen atom, a sulfur atom, or a nitrogen atom; any one of carbon atoms marked with * or Z in the case where Z is a nitrogen atom is bonded to X directly or via a $C_1$ to $C_8$ alkylene group (provided that one carbon atom or two or more carbon atoms that are not adjacent to each other in the alkylene group may be substituted with an oxygen atom, a nitrogen atom, a sulfur atom, or a carbonyl group (C=O)); and a carbon atom marked with ** is bonded to $—\{(CF_2)_{p1}(CF)_{p2}[CF(CF_3)]_{p3}[C(CF_3)_2]_{p4}O\}_q—C_nF_{2n+1}$.

<29> The fluorine-based compound according to any one of <22> to <28>, wherein Y is a linking group represented by any of the following formulae (Y1) to (Y3):

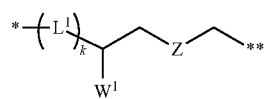

(Y1)

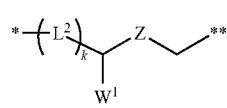

(Y2)

-continued

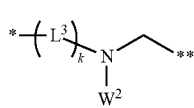
(Y3)

where, in the formula, $W^1$ and $W^2$ each represent a polar group, or a group having a polar group including one or more polar groups, one or more methylene groups ($CH_2$), one or more methine groups (CH), one or more quaternary carbon atoms, or a group formed by combination of two or more thereof; k represents 0 or 1; $L^1$ to $L^3$ each represent —$CH_2$—, —$OCH_2$—, —$CH_2O$—, or —C(=O)—; Z represents an oxygen atom or NH; and ** each represent binding positions with X and —{$(CF_2)_{p1}$ $(CF)_{p2}[CF(CF_3)]_{p3}[C(CF_3)_2]_{p4}O\}_q$—$C_nF_{2n+1}$.

<30> The fluorine-based compound according to any one of <22> to <29>, wherein the perfluoroalkyleneoxy group in the formula (1) is a group represented by the following formula (2a) or (2b):

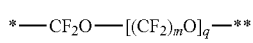
(2a)

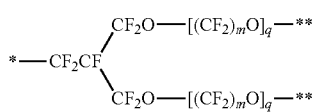
(2b)

where, in the formulae, m represents an integer of 2 to 4, q represents an integer of 1 to 30, a plurality of m's in the case where q in the formula (2a) is 2 or more, and a plurality of m's in the formula (2b) may be the same as or different from each other, * represents a binding position with Y, and ** represents a binding position with $C_nF_{2n+1}$.

<31> The fluorine-based compound according to any one of <22>-<29>, wherein the perfluoroalkyleneoxy group in the formula (1) is a group represented by the following formula (3a) or (3b):

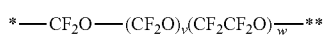
(3a)

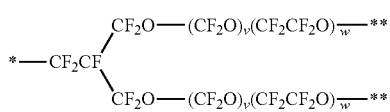
(3b)

where in the formulae, v represents an integer of 1 to 20 and w represents an integer of 1 to 20, provided that (v+w) is an integer of 1 to 30; the binding sequence of ($CF_2O$) and ($CF_2CF_2O$) is not limited, * represents a binding position with Y, and ** represents a binding position with $C_nF_{2n+1}$.

<32> A fluorine-based compound represented by any of following formulae (1a) to (1f):

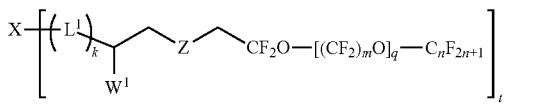
(1a)

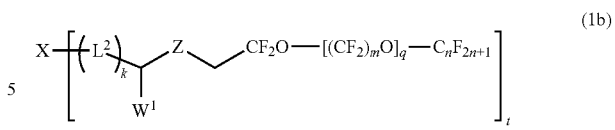
(1b)

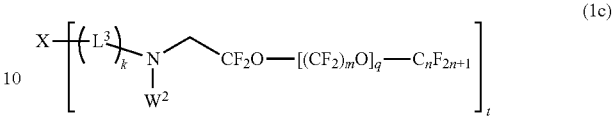
(1c)

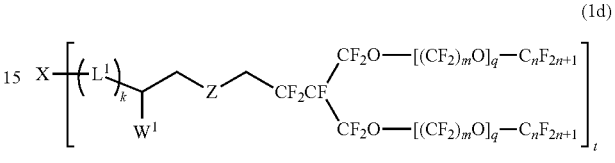
(1d)

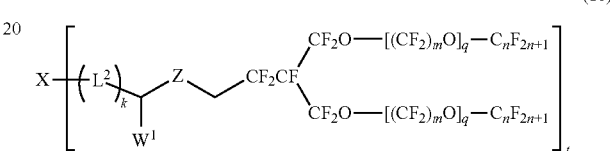
(1e)

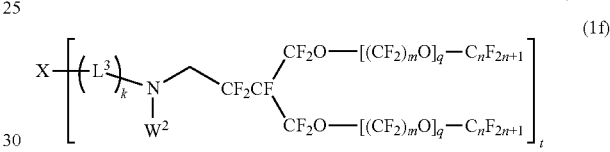
(1f)

where, in the formulae, X represents a cyclic group which may be substituted; $W^1$ and $W^2$ each represent a polar group, or a group having a polar group including one or more polar groups, one or more methylene groups ($CH_2$), one or more methine groups (CH), one or more quaternary carbon atoms, or a group formed by combination of two or more thereof; k represents 0 or 1; $L^1$ to $L^3$ each represent —$CH_2$—, —$OCH_2$—, —$CH_2O$—, or —C(=O)—; Z represents an oxygen atom or NH; m represents an integer of 2 to 4; n represents an integer of 1 to 10; t represents an integer of 2 to 10; and q represents an integer of 1 to 30, provided that a plurality of $L^1$ to $L^3$, k, $W^1$, $W^2$, Z, m, n, and q each present in the formula may be the same as or different from each other.

<33> A fluorine-based compound represented by any of following formulae (1g) to (1l):

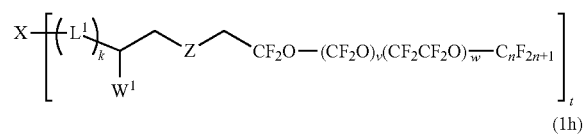
(1g)

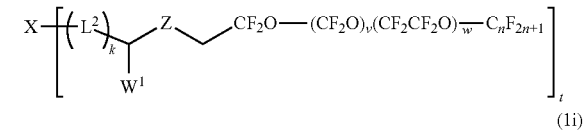
(1h)

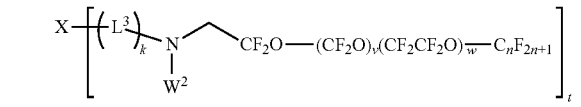
(1i)

-continued

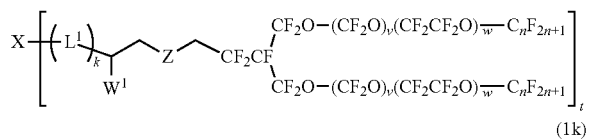
(1j)

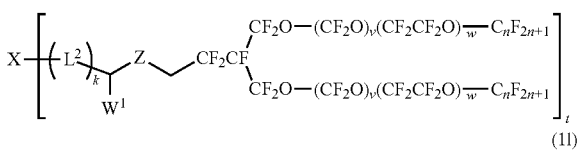
(1k)

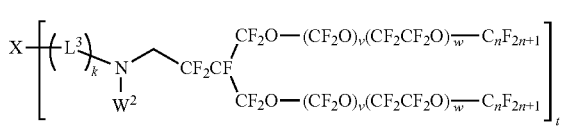
(1l)

where in the formulae, X represents a cyclic group which may be substituted; $W^1$ and $W^2$ each represent a polar group, or a group having a polar group including one or more polar groups, one or more methylene groups ($CH_2$), one or more methine groups (CH), one or more quaternary carbon atoms, or a group formed by combination of two or more thereof; k represents 0 or 1; $L^1$ to $L^3$ each represent —$CH_2$—, —$OCH_2$—, —$CH_2O$—, or —C(=O)—; Z represents an oxygen atom or NH; v represents an integer of 1 to 20; and w represents an integer of 1 to 20, provided that (v+w) is an integer of 1 to 30; the binding sequence of ($CF_2O$) and ($CF_2CF_2O$) is not limited; n represents an integer of 1 to 10; and t represents an integer of 2 to 10, provided that a plurality of $L^1$ to $L^3$, k, $W^1$, $W^2$, Z, v, w, and n each present in the formula may be the same as or different from each other.

<34> A fluorine-based compound of any of the following L-1 to L-14:

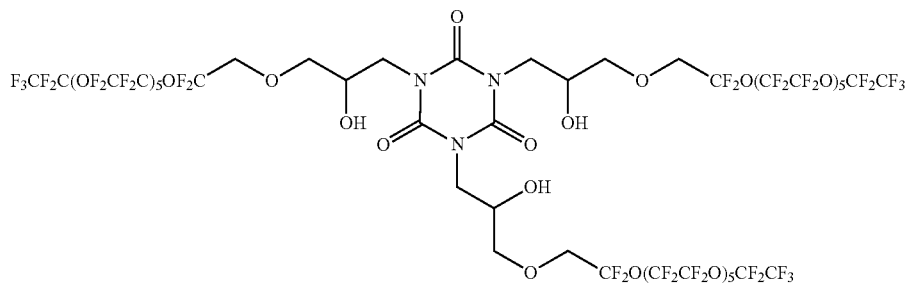
L-1

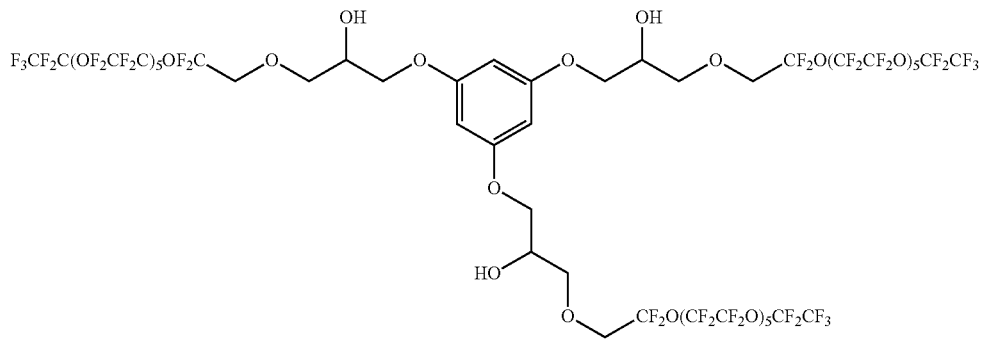
L-2

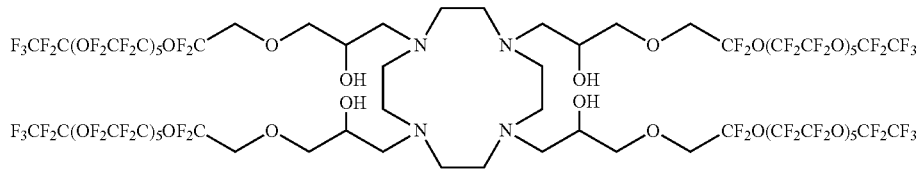
L-3

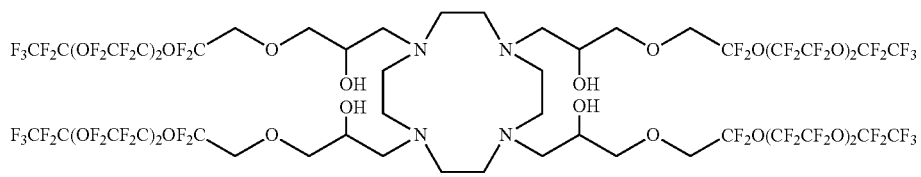
L-4

-continued
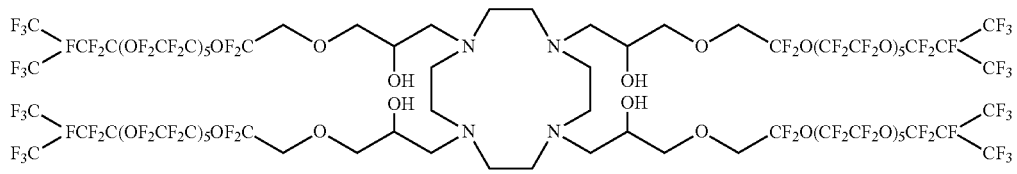
L-5
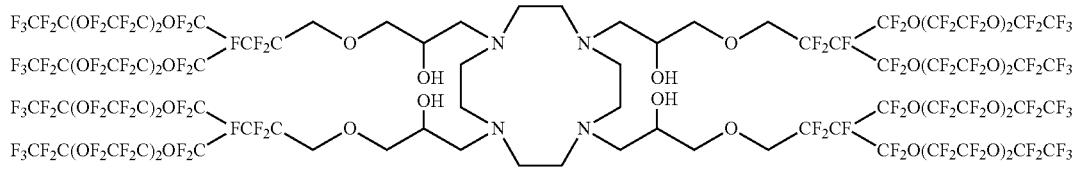
L-6
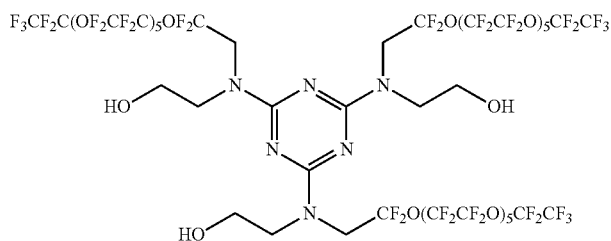
L-7
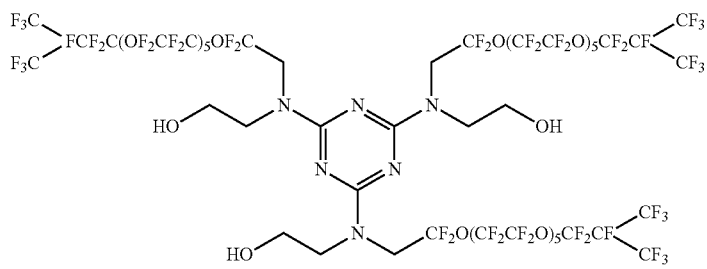
L-8
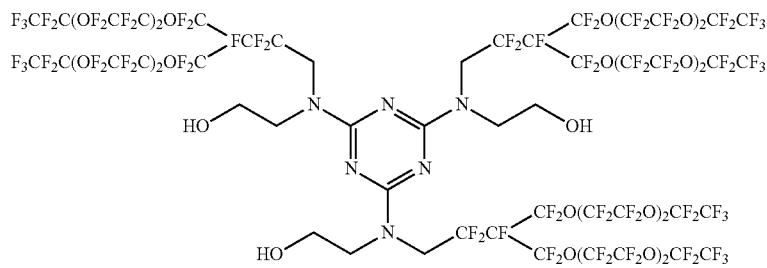
L-9
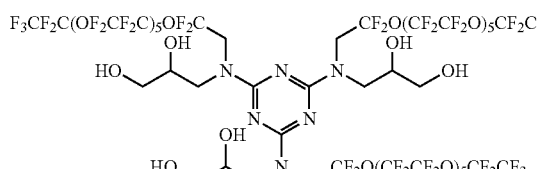
L-10
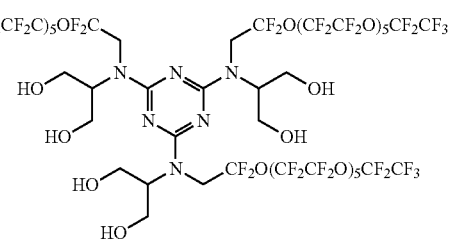
L-11

-continued

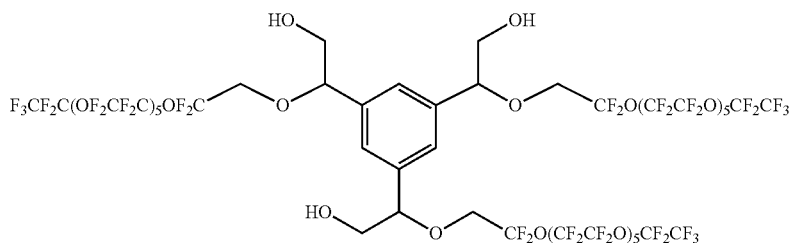

L-12

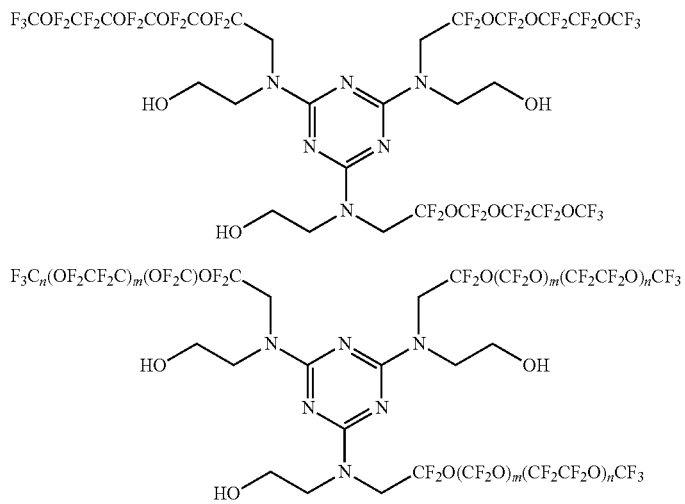

L-13

L-14 where, in the formula (L-14), m represents an integer of 1 to 20, n represents an integer of 1 to 20, provided that (m+n) is an integer of 1 to 30 and the binding sequence of ($CF_2O$) and ($CF_2CF_2O$) is not limited.

Advantage of the Invention

According to the present invention, a lubricant composition having further improved characteristics required for a lubricant, particularly further improved characteristics required for a lubricant for a recording medium can be provided.

Furthermore, according to the present invention, a lubricant composition that is further improved, particularly, in terms of the solubility in a solvent, the shape of the coated surface, and the adsorption performance with respect to a base material can be provided.

Moreover, according to the present invention, various uses of the lubricant composition, as well as a film and a laminate having the film, a magnetic recording medium, a head slider, and a magnetic recording device, each of which is produced using the composition, can be provided.

Furthermore, the present invention can provide a novel fluorine-based compound which is useful in various uses, for example, a use as a lubricant.

According to the present invention, a thinner lubricating layer can be obtained, and thus, a high substrate-adsorption property, sliding-resistance characteristic, high stability, surface smoothness, and a head transfer inhibiting property can be further improved.

BRIEF DESCRIPTION OF THE DRAWINGS

FIG. 1 is a schematic cross-sectional view of an example of a magnetic recording medium of the present invention.

DESCRIPTION OF REFERENCE NUMERALS AND SIGNS

1 Substrate
2 Soft Magnetic Layer
3 Intermediate Layer
4 Magnetic Recording Layer
5 Protective Layer
6 Lubricating Layer

DETAILED DESCRIPTION OF THE INVENTION

Hereinafter, the present invention will be described in detail. Further, in the present specification, a range of numerical values represented using "to" means a range that includes the numerical values described before and after the "to" as a minimum value and a maximum value.

1. Lubricant Composition

The present invention relates to a lubricant composition that contains at least one kind of compound represented by the following formula (1). The following compound contains a polar group such as a hydroxyl group and the like in Y in the formula. The polar group acts as a group adsorbing onto a substrate (or to a protective film layer such as a carbonaceous film, an oxide film such as $SiO_2$ and $ZrO_2$, a nitride film, and a boride film, which are formed on the substrate). For example, the well-known lubricants "FOMBLIN Z-DOL" and "FOMBLIN Z-TETRAOL", contain a polar group (hydroxyl group) at both terminals of a perfluoropolyether. With the compound, the adsorptive groups at both terminals are adsorbed on the substrate, and thus, it is difficult to obtain a thin film with a uniform film thickness since the perfluoropolyether chain is bent. As described above, the compound represented by the following formula (1) of the present invention has a polar group between one terminal of the perfluoroalkylene(oxy) group and a cyclic group. Accordingly, this compound has a higher degree of freedom of the perfluoroalkylene(oxy) group on the substrate, and the cyclic group and the polar group are brought into the substrate to form an alignment in which the perfluoroalkylene(oxy) group is upright with respect to the substrate. As a result, the lubricant composition of the present invention can provide a thinner lubricating layer uniformly, has excellent lubricating performance and excellent sliding-resistance characteristics, and can maintain the sliding-resistance characteristic even if the non-adsorptive layer is absent. Moreover, in the present invention, by using the compound of the following formula (1), the non-adsorptive layer can be removed, and the lubricating layer can be thinner.

Furthermore, the compound represented by the following formula (1) is characterized in that Y in the formula has no aromatic cyclic group. Due to this characteristic, as compared with a compound in which Y has an aromatic cyclic group, it becomes possible to provide a lubricant composition which is further improved in terms of the solubility in a solvent, the shape of the coated surface, and the adsorption performance with respect to a base material. By using the compound having such a characteristic, the specific mechanism for improvement of all of the characteristics is not clear, but when Y has no aromatic cyclic group, the structure of the compound becomes more flexible, and as a result, it is presumed that, for example, whether the crystallinity of the compound is removed or reduced has an effect thereon.

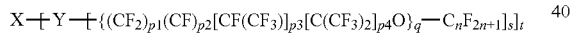

(1)

In the formula (1), X represents a cyclic group that may be substituted; and Y represents a divalent or higher-valent linking group having at least one polar group and having no aromatic cyclic group.

In the formula (1), X represents a cyclic group that may be substituted. Examples of the cyclic group include both the residue of an aromatic ring (aromatic cyclic group) and the residue of a non-aromatic ring (non-aromatic cyclic group such as an aza-crown ring including 12-aza-crown-4,15,18, 21,24-aza-crown, and the like and a cyclohexane ring). In addition, the cyclic group may be a residue of a ligand coordinated with a metal, or may be originally a chain-like group but forms a cyclic structure for the first time by being coordinated with a central metal. That is, in the present specification, the "cyclic group" is included in the meaning of a cyclic group as long as the cyclic group forms a cyclic structure type aggregate, supermolecule, or complex by clustering of a plurality of molecules, even if the "cyclic group" is originally a non-cyclic group such as a chain-like group and the like. Though there is no particular limitation on atoms constituting the cyclic group, it is preferable that at least a carbon atom be included as a ring-constituting atom. The cyclic group may be selected from cyclic groups including only the carbon atom as the ring-constituting atom, or from cyclic groups including a hetero atom such as a nitrogen atom, an oxygen atom, a sulfur atom, and the like as the ring-constituting atom together with the carbon atom. From the viewpoint of an adsorption property with respect to a substrate, it is preferable that the cyclic group be selected from cyclic groups including the hetero atom as the ring-constituting atom, and particularly, from cyclic groups including the nitrogen atom, such as a residue of a triazine ring and the like. Furthermore, X may be a cyclic group having plural rings formed by connecting a plurality of residues of hetero rings into a ring shape (for example, phthalocyanine, porphyrin, corrole, and the like). Further, these cyclic groups may be in a state of being coordinated to the central metal.

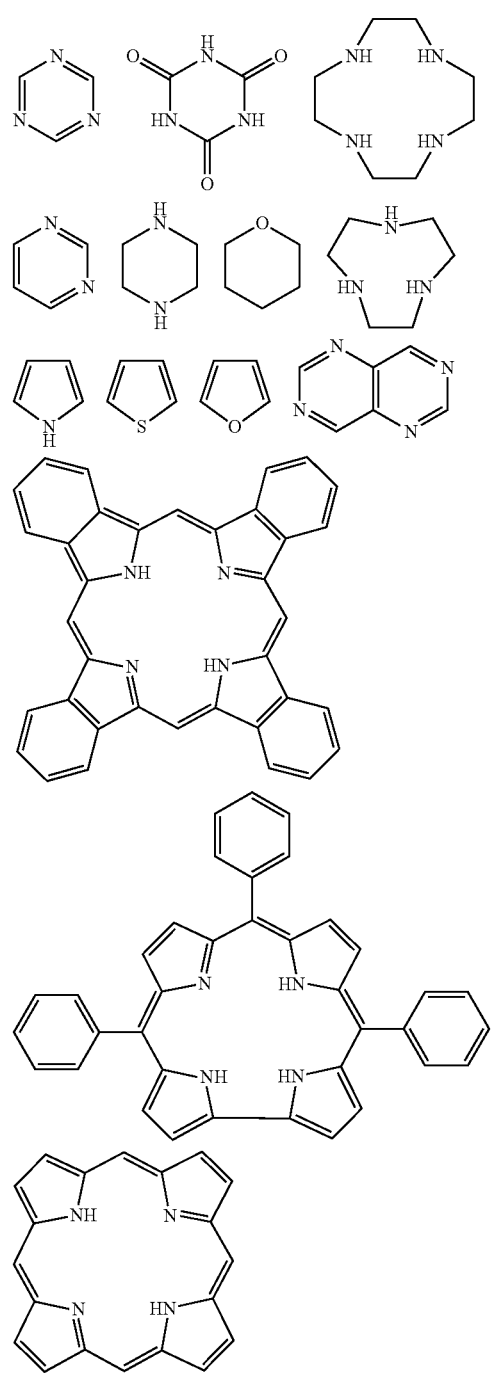

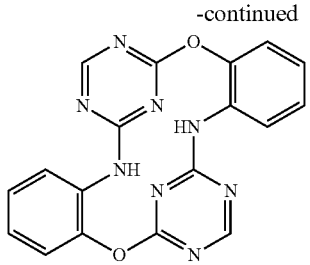

Examples of the aromatic cyclic group having only carbon atoms as the ring-constituting atom include a residue of a benzene ring. A residue of a ring (for example, triphenylene, phenylene, and coronene) formed by the condensation of a plurality of benzene rings, and a cyclic group formed when a plurality of benzene rings are connected into a ring shape are also preferable. Hereinbelow, examples of the aromatic cyclic group including only the carbon atoms as the ring-constituting atom are shown, but the cyclic group is not limited thereto. Moreover, hereinbelow, the substituent is removed, and only the skeleton of the cyclic group is shown. Y may be substituted in any position, and among the cyclic groups shown below, any of substitutable hydrogen atoms may be substituted with Y.

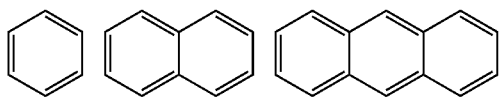

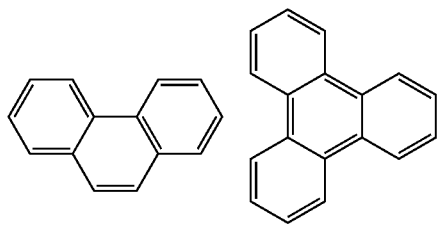

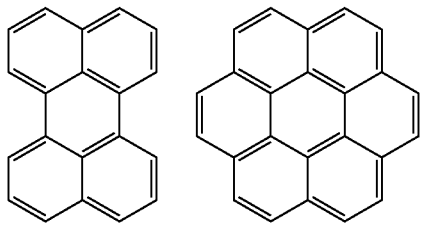

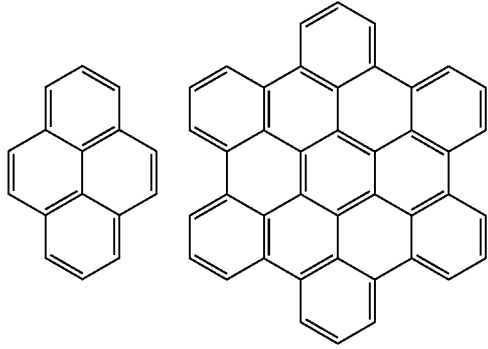

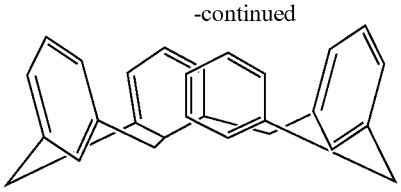

Examples of the non-aromatic alicyclic group include the following ones, but the alicyclic group is not limited thereto. Moreover, hereinbelow, the substituent is removed, and only the skeleton of the cyclic group is shown. Y may be substituted in any position, and among the cyclic groups shown below, any of substitutable hydrogen atoms may be substituted with Y.

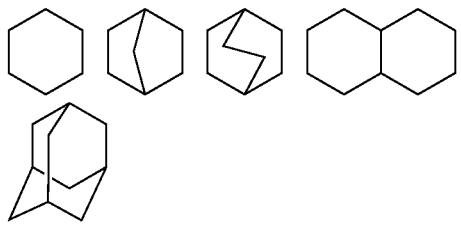

X preferably represents a monocyclic compound residue which may have at least one substituent, more preferably is a residue selected from the group consisting of the residues of benzene, cyclohexane, triazine, isocyanuric acid, pyrimidine, 1,4,7-triaza cyclononane and 1,4,7,10-tetraza cyclododecane, or is even more preferably a cyclic group represented by any one of following formulae (X1)-(X4).

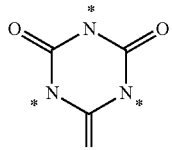 (X1)

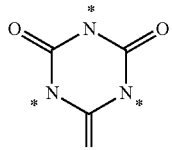 (X2)

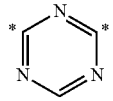 (X3)

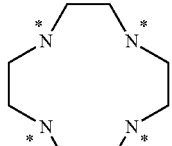 (X4)

In the formulae, "*" indicates a site capable of linking, Y links to the two or more site indicated by "*", and other substituent (s) may link to the site(s) indicated by "*" where Y doesn't link or any sites capable of linking.

The cyclic group represented by X may have at least one substituent. Examples of the substituent include any substituents containing a polar group such as hydroxy. The polar group may bind to any atom(s) which is embedded in the cyclic group directly or via any linking group. Examples of the linking group include a $C_{1-20}$ alkylene, $C_{2-20}$ alkenylene, $C_{2-20}$ alkynylene and $C_{1-20}$ aromatic group (a carbon atom or two or more carbon atoms, not adjacent to each other, may be replaced with an oxygen, nitrogen or sulfur atom and any hydrogen atom(s) therein may be replaced with fluorine atom).

And, examples of the substituent with which the cyclic group represented by X may be substituted include a hydrogen atom and the following Substituent Group T.

Substituent Group T:

Halogen atoms (e.g., fluorine, chlorine, bromine and iodine atoms), alkyls (preferably $C_{1-30}$ alkyls such as methyl, ethyl, n-propyl, isopropyl, tert-butyl, n-octyl and 2-ethylhexyl), cycloalkyls (preferably $C_{3-30}$ substituted or non-substituted cycloalkyls such as cyclohexyl, cyclopentyl and 4-n-dodecyl cyclohexyl), bicycloalkyls (preferably $C_{5-30}$ substitute or non-substituted bicycloalkyls, namely monovalent residues formed from $C_{5-30}$ bicycloalkanes from which a hydrogen atom is removed, such as bicyclo[1,2,2]heptane-2-yl and bicyclo[2,2,2]octane-3-yl), alkenyls (preferably $C_{2-30}$ alkenyls such as vinyl and allyl); cycloalkenyls (preferably $C_{3-30}$ substituted or non-substituted cycloalkenyls, namely monovalent residues formed from $C_{3-30}$ cycloalkenes from which a hydrogen atom is removed, such as 2-cyclopentene-1-yl and 2-cyclohexene-1-yl), bicycloalkenyls (preferably $C_{5-30}$ substituted or non-substituted bicycloalkenyls, namely monovalent residues formed from $C_{5-30}$ bicycloalkenes from which a hydrogen atom is removed, such as bicyclo[2,2,1]hepto-2-en-1-yl and bicyclo[2,2,2]octo-2-en-4-yl), alkynyls (preferably $C_{2-30}$ substitute or non-substituted alkynyls such as etynyl and propargyl), aryls (preferably $C_{6-30}$ substitute or non-substituted aryls such as phenyl, p-tolyl and naphthyl), heterocyclic groups (preferably (more preferably $C_{3-30}$) substituted or non-substituted, 5-membered or 6-membered, aromatic or non-aromatic heterocyclic monovalent residues such as 2-furyl, 2-thienyl, 2-pyrimidinyl and 2-benzothiazolyl), cyano, hydroxyl, nitro, carboxyl, alkoxys (preferably $C_{1-30}$ substituted or non-substituted alkoxys such as methoxy, ethoxy, iso-propoxy, tert-butoxy, n-octyloxy and 2-methoxyethoxy), aryloxys (preferably $C_{6-30}$ substituted or non-substituted aryloxys such as phenoxy, 2-methylphenoxy, 4-t-butylphenoxy, 3-nitrophenoxy and 2-tetradecanoyl aminophenoxy), silyloxys (preferably $C_{3-20}$ silyloxys such as trimethylsilyloxy and tert-butyldimethylsilyloxy), hetero-cyclic-oxys (preferably $C_{2-30}$ substituted or non-substituted hetero-cyclic-oxys such as 1-phenyltetrazole-5-oxy and 2-tetrahydropyrenyloxy), acyloxys (preferably $C_{2-30}$ substitute or non-substituted alkylcarbonyloxys and $O_{6-30}$ substituted or non-substituted arylcarbonyloxys such as formyloxy, acetyloxy, pivaloyloxy, stearoyoxy, benzoyloxy and p-methoxyphenylcarbonyloxy), carbamoyloxys (preferably $C_{1-30}$ substituted or non-substituted carbamoyloxys such as N,N-dimethyl carbamoyloxy, N,N-diethyl carbamoyloxy, morpholinocarbonyloxy, N,N-di-n-octylaminocarbonyloxy and N-n-octylcarbamyloxy), alkoxy carbonyloxys (preferably $C_{2-30}$ substituted or non-substituted alkoxy carbonyloxys such as methoxy carbonyloxy, ethoxy carbonyloxy, tert-butoxy carbonyloxy and n-octyloxy carbonyloxy), aryloxy carbonyloxys (preferably $C_{7-30}$ substituted or non-substituted aryloxy carbonyloxys such as phenoxy carbonyloxy, p-methoxyphenyl carbonyloxy and p-n-hexadecyloxyphenoxy carbonyloxy), aminos (preferably $C_{0-30}$ substituted or non-substituted alkylaminos and $C_{6-30}$ substituted or non-substituted arylaminos such as amino, methylamino, dimethylamino, anilino, N-methyl-anilino and diphenylamino), acylaminos (preferably $O_{1-30}$ substituted or non-substituted alkylcarbonylaminos and $C_{6-30}$ substituted or non-substituted arylcarbonylaminos such as formylamino, acetylamino, pivaloylamino, lauroylamino and benzoylamino), aminocarbonylaminos (preferably $C_{1-30}$ substituted or non-substituted aminocarbonylaminos such as carbamoylamino, N,N-dimethylaminocarbonylamino, N,N-diethylamino carbonylamino and morpholino carbonylamino), alkoxycarbonylaminos (preferably $C_{2-30}$ substituted or non-substituted alkoxycarbonylaminos such as methoxycarbonylamino, ethoxycarbonylamino, tert-butoxycarbonylamino, n-octadecyloxycarbonylamino and N-methyl-methoxy carbonylamino), aryloxycarbonylaminos (preferably $C_{7-30}$ substituted or non-substituted aryloxycarbonylaminos such as phenoxycarbonylamino, p-chloro phenoxycarbonylamino and m-n-octyloxy phenoxy carbonylamino), sulfamoylaminos (preferably $C_{0-30}$ substituted or non-substituted sulfamoylaminos such as sulfamoylamino, N,N-dimethylamino sulfonylamino and N-n-octylamino sulfonylamino), alkyl- and aryl-sulfonylaminos (preferably $C_{1-30}$ substituted or non-substituted alkyl-sulfonylaminos and $C_{6-30}$ substituted or non-substituted aryl-sulfonylaminos such as methyl-sulfonylamino, butyl-sulfonylamino, phenyl-sulfonylamino, 2,3,5-trichlorophenyl-sulfonylamino and p-methylphenyl-sulfonylamino), mercapto, alkylthios (preferably substituted or non-substituted $C_{1-30}$ alkylthios such as methylthio, ethylthio and n-hexadecylthio), arylthios (preferably $C_{6-30}$ substituted or non-substituted arylthios such as phenylthio, p-chlorophenylthio and m-methoxyphenylthio), heterocyclic-thios (preferably $C_{2-30}$ substituted or non-substituted heterocyclic-thios such as 2-benzothiazolyl thio and 1-phenyltetrazol-5-yl-thio), sulfamoyls (preferably $C_{0-30}$ substituted or non-substituted sulfamoyls such as N-ethylsulfamoyl, N-(3-dodecyloxypropyl)sulfamoyl, N,N-dimethylsulfamoyl, N-acetylsulfamoyl, N-benzoylsulfamoyl, N—(N'-phenylcarbamoyl)sulfamoyl), sulfo, alkyl- and aryl-sulfinyls (preferably $C_{1-30}$ substituted or non-substituted alkyl- or $C_{6-30}$ substituted or non-substituted aryl-sulfinyls such as methylsulfinyl, ethylsulfinyl, phenylsulfinyl and p-methylphenylsulfinyl), alkyl- and aryl-sulfonyls (preferably $C_{1-30}$ substituted or non-substituted alkyl-sulfonyls and $C_{6-30}$ substituted or non-substituted arylsulfonyls such as methylsulfonyl, ethylsulfonyl, phenylsulfonyl and p-methylphenylsulfonyl), acyls (preferably $C_{2-30}$ substituted non-substituted alkylcarbonyls, and $C_{7-30}$ substituted or non-substituted arylcarbonyls such as formyl, acetyl and pivaloyl benzyl), aryloxycarbonyls (preferably $C_{7-30}$ substituted or non-substituted aryloxycarbonyls such as phenoxycarbonyl, o-chlorophenoxycarbonyl, m-nitrophenoxycarbonyl and p-tert-butylphenoxycarbonyl), alkoxycarbonyls (preferably $C_{2-30}$ substituted or non-substituted alkoxycarbonyls such as methoxycarbonyl, ethoxycarbonyl, tert-butoxycarbonyl and n-octadecyloxycarbonyl), carbamoyls (preferably $C_{1-30}$ substituted or non-substituted carbamoyls such as carbamoyl, N-methylcarbamoyl, N,N-dimethylcarbamoyl, N,N-di-n-octylcarbamoyl and N-(methylsulfonyl)carbamoyl), aryl- and heterocyclic-azos (preferably $C_{6-30}$ substituted or non-substituted arylazos and $C_{3-30}$ substituted or non-substituted heterocicazos such as phenylazo, p-chlorophenylazo, 5-ethylthio-1,3,4-thiadiazol-2-yl-azo), imides (preferably, N-succinimide and N-phthalimide), phosphinos (preferably $C_{2-30}$ substituted or non-substituted phosphinos such as dimethyl phosphino, diphenyl phosphino and methylphenoxy phosphino), phosphinyls (preferably $C_{2-30}$ substituted or non-substituted phosphinyls such as phosphinyl, dioctyloxy phosphinyl and diethoxy phosphinyl), phosphinyloxys (preferably $C_{2-30}$ substituted or non-substituted phosphinyloxys such as diphenoxyphosphinyloxy and dioctyloxyphosphinyloxy), phosphinylaminos (preferably $C_{2-30}$ substituted or non-substituted phosphinylaminos such as dimethoxy phosphinylamino and dimethylamino phosphinylamino) and silyls (preferably $C_{3-30}$ substituted or non-substituted silyls such as trimethylsilyl, tert-butylmethylsilyl and phenyldimethylsilyl).

Moreover, preferable examples of the substituent of X in the formula (1) include a substituent containing a polar group such as a hydroxyl group (including a polar group itself, such as a hydroxyl group), a substituent containing a halogen atom such as a fluorine atom (including a halogen atom itself), and a $C_1$ to $C_5$ alkoxy group. X preferably has a substituent containing a polar group such as a hydroxyl group or has no substituent.

Furthermore, the compound of the formula (1) may be a multimer such as a bis-form compound, in which two or more X's are bonded directly or via a carbon atom or the like (for example, —$CH_2$—). In the case of the multimer, the structures of each monomer may be the same as or different from each other.

In the formula (1), Y represents a divalent or higher-valent linking group having at least one polar group, and having no aromatic cyclic group. The polar group may be a monovalent group at the terminal or a divalent group at a position other than the terminal. From the viewpoint of the adsorption property with respect to the substrate surface, the polar group is preferably a monovalent group at the terminal. Examples of the polar group include a hydroxyl group (—OH), an amino group (—$NH_2$), a mercapto group (—SH), a carboxyl group (—COOH), an alkoxycarbonyl group (—COOR; in which R is an alkyl group), a carbamoyl group (—$CONH_2$), a ureido group (—$NHCONH_2$), a sulfonamide group (—$SO_2NH_2$), a phosphoric acid group (—OP(=O)(OH)$_2$), a sulfonic acid group (—$SO_3H$), a sulfino group (—S(=O)OH), a sulfide group (—S—), a disulfide group (—S—S—), a sulfinyl group (—S(=O)—), an aminocarbonyl group (—NHCO—), a ureylene group (—NHCONH—), an imino group (C=NH or C=NR (in which R is a substituent)), an imide group (—C(=O)NHC(=O)—), a sulfonimide group (—S(=O)$_2$NHS(=O)$_2$—), and an aminosulfonyl group (—$NHSO_2$—).

Among these, from the above-described viewpoints, a monovalent polar group is preferable, and a hydroxyl group is more preferable.

The divalent or higher-valent linking group represented by Y is preferably a divalent or higher-valent linking group having a substituted or unsubstituted imino group (C=NH or C=NR (in which R is a substituent)), a sulfide group (S), an alkylene group having 1 to 20 carbon atoms (provided that one carbon atom, or two or more carbon atoms that are not adjacent to each other may be substituted with an atom such as oxygen, nitrogen and sulfur and a hydrogen atom may be substituted with a halogen atom (a fluorine atom, a chlorine atom, a bromine atom, and an iodine atom)), an alkenylene group having 2 to 20 carbon atoms, an alkynylene group having 2 to 20 carbon atoms, a carbonyl group (C=O), a sulfinyl group (S=O), a sulfonyl group (S(=O)$_2$), a phosphoryl group (P=O), an oxygen atom (O), and a combination of one or more selected therefrom.

Preferable examples of Y include a linear or branched divalent to pentavalent linking group having 1 to 15 carbon atoms (more preferably 1 to 10 carbon atoms), which contains at least one atom or atom group selected from a group consisting of an ether-based oxygen atom, an amine-based nitrogen atom, and an amide bond.

Furthermore, examples of Y include a linking group, which contains a $C_2$ to $C_{10}$ alkylene group, provided that one carbon atom or two or more carbon atoms that are not adjacent to each other in the alkylene group may be substituted with an oxygen atom, a nitrogen atom, a sulfur atom, or a carbonyl group (C=O), and further, a polar group is bonded to any carbon atom in the alkylene group (or to a nitrogen atom in the case where the carbon atom is substituted with a nitrogen atom) directly or via a $C_1$ to $C_5$ alkylene group. For example, the following perfluoroalkyleneoxy group is bonded to a carbon atom at the terminal of the alkylene group.

Moreover, examples of Y include a linking group containing a partial structure represented by the following formula.

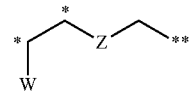

In the formula, W represents a polar group, Z represents an oxygen atom, a sulfur atom, or a nitrogen atom; any one of carbon atoms marked with * or Z in the case where Z is a nitrogen atom is bonded to X directly or via a $C_1$ to $C_8$ alkylene group (provided that one carbon atom or two or more carbon atoms that are not adjacent to each other in the alkylene group may be substituted with an oxygen atom, a nitrogen atom, a sulfur atom, or a carbonyl group (C=O)); and a carbon atom marked with ** is bonded to —{$(CF_2)_{p1}(CF)_{p2}[CF(CF_3)]_{p3}[C(CF_3)_2]_{p4}O$}$_q$—$C_nF_{2n+1}$ directly or via a $C_1$ to $C_8$ alkylene group (provided that one carbon atom or two or more carbon atoms that are not adjacent to each other in the alkylene group may be substituted with an oxygen atom, a nitrogen atom, a sulfur atom, or a carbonyl group (C=O)).

Furthermore, examples of Y include a linking group represented by any of the following formulae (Y1) to (Y3).

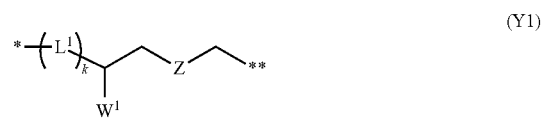
(Y1)

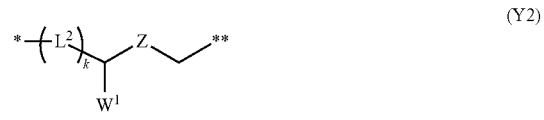
(Y2)

(Y3)

In the formula, $W^1$ and $W^2$ each represent a polar group, or a group having a polar group including one or more polar groups, one or more methylene groups ($CH_2$), one or more methine groups (CH), one or more quaternary carbon atoms, or a group formed by combination of two or more thereof; k represents 0 or 1; $L^1$ to $L^3$ each represent —$CH_2$—, —$OCH_2$—, —$CH_2O$—, or —C(=O)—; Z represents an oxygen atom or NH; and * and ** each represent binding positions with X and —{$(CF_2)_{p1}(CF)_{p2}[CF(CF_3)]_{p3}[C(CF_3)_2]_{p4}O$}$_q$—$C_nF_{2n+1}$, respectively.

Examples of the group having a polar group including one or more polar groups, one or more methylene groups ($CH_2$), one or more methine groups (CH), one or more quaternary carbon atoms, or a group formed by combination of two or more thereof represented by $W^1$ and $W^2$ include the following groups.

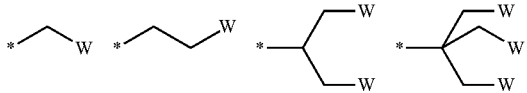

In the formula, W represents a polar group, and * represents the binding site with any of the formulae (Y1), (Y2), and (Y3).

The cyclic group X in the formula (1) has t perfluoroalkyleneoxy groups represented by the following formula. t represents an integer of 2 to 10, and a preferable range of t varies depending on the structure of the cyclic group. t is usually preferably from 2 to 6, and more preferably from 2 to 4.

$$-Y-[\{(CF_2)_{p1}(CF)_{p2}[CF(CF_3)]_{p3}[C(CF_3)_2]_{p4}O\}_q-C_nF_{2n+1}]_s$$

In the formula, Y represents the linking group, p1 represents an integer of 1 to 4, p2, p3, and p4 each represent an integer of 0 to 4, q represents an integer of 0 to 30, n represents an integer of 1 to 10, and s represents an integer of 1 to 4. However, the binding sequence of $-(CF_2)_{p1}-$, $-(CF)_{p2}-$, $-[CF(CF_3)]_{p3}-$, and $-[C(CF_3)_2]_{p4}-$ is not limited, and $-\{(CF_2)_{p1}(CF)_{p2}[CF(CF_3)]_{p3}[C(CF_3)_2]_{p4}O\}-$ means a perfluoroalkyleneoxy group in which a perfluoroalkylene unit selected from $-(CF_2)_{p1}-$, $-(CF)_{p2}-$, $-[CF(CF_3)]_{p3}-$, and $-[C(CF_3)_2]_{p4}-$ and an oxygen atom are distributed randomly. Further, when q is 2 or more, a plurality of $-\{(CF_2)_{p1}(CF)_{p2}[CF(CF_3)]_{p3}[C(CF_3)_2]_{p4}O\}-$ may be the same as or different from each other; when s is 2 or more, a plurality of n's and q's may be the same as or different from each other; and when t is 2 or more, a plurality of s's and Y's may be the same as or different from each other. Further, when p2 is 1 or more, that is, (CF) is included, the perfluoroalkyleneoxy group has a branched structure.

p1 is preferably from 1 to 3, p2 is preferably 0 or 1, p3 is preferably from 0 to 2, and p3 is preferably from 0 to 2. Further, q is preferably from 2 to 20, and more preferably from 3 to 10. s is preferably from 1 to 4, and more preferably from 1 to 3.

Examples of the perfluoroalkyleneoxy group include a group represented by the following formula (2a) or (2b).

 (2a)

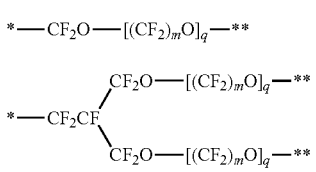 (2b)

In the formulae (2a) and (2b), m represents an integer of 2 to 4, q represents an integer of 1 to 30, * represents a binding position with Y, and ** represents a binding position with $C_nF_{2n+1}$. q is preferably from 3 to 10. A plurality of m's in the case where q in the formula (2a) is 2 or more, and a plurality of m's in the formula (2b) may be the same as or different from each other.

Moreover, examples of the perfluoroalkyleneoxy group include a group represented by the following formula (3a) or (3b).

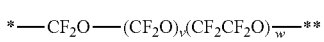 (3a)

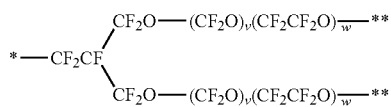 (3b)

In the formulae (3a) and (3b), w represents an integer of 1 to 30, provided that (v+w) is an integer of 1 to 30; * represents a binding position with Y; and ** represents a binding position with $C_nF_{2n+1}$. In the formula, the binding sequence of ($CF_2O$) and ($CF_2CF_2O$) is not particularly limited. v is preferably from 1 to 15, and more preferably from 1 to 10; and w is preferably from 1 to 15, and more preferably from 1 to 10. Further, (v+w) is preferably from 2 to 30, and more preferably from 2 to 20.

The perfluoroalkyleneoxy group has a perfluoroalkyl group, $-C_nF_{2n+1}$, at the terminal. The perfluoroalkyl group may be linear or branched. n is an integer of 1 to 10, and preferably 2 to 8.

A higher content of fluorine per molecule of the compound represented by the formula (1) is preferable from the viewpoint of a higher solubility in a fluorine-based solvent. The content of fluorine per molecule is preferably from 37 to 76% by mass, and more preferably from 50 to 76% by mass.

Examples of the compound represented by the formula (1) include the compounds represented by the following formulae (1a) to (1f).

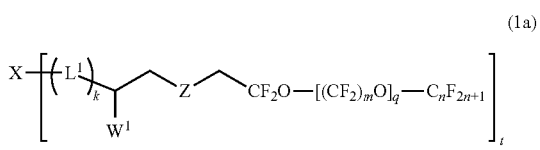 (1a)

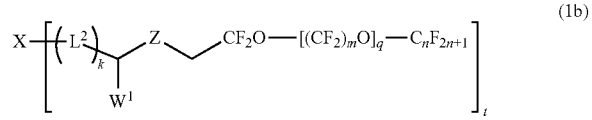 (1b)

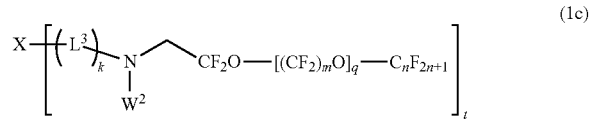 (1c)

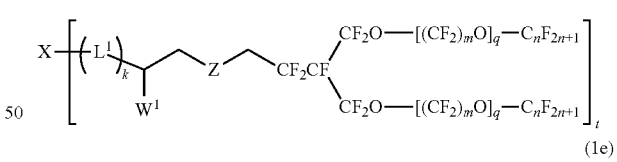 (1d)

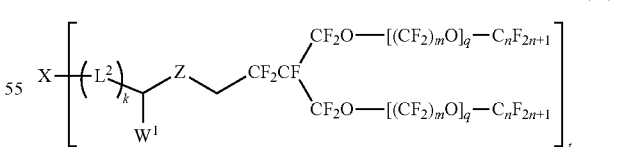 (1e)

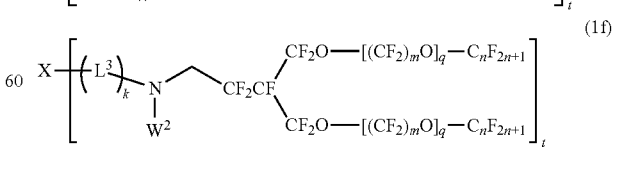 (1f)

Each of the definitions of symbols in the formulae is the same as above, and preferable ranges thereof are also the same.

Moreover, examples of the compound represented by the formula (1) include the groups represented by the following formula (1g) to (1l).

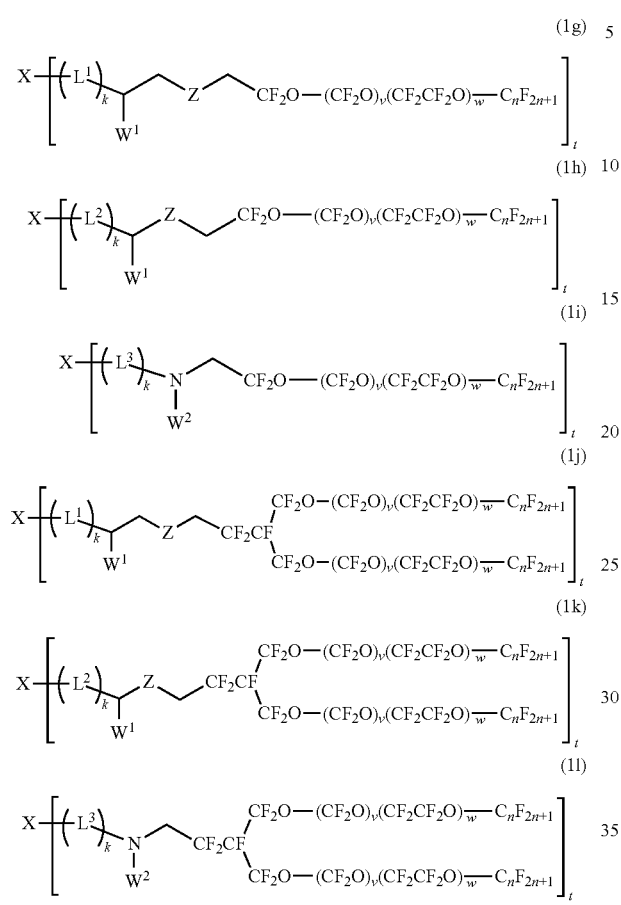

Each of the definitions of symbols in the formulae is the same as above, and preferable ranges thereof are also the same.

Specific examples of the compound represented by the formula (1) include, but are not limited to, those shown below. Further, the numerical value in the parenthesis added to each of the exemplified compound means the content of the fluorine atom. However, in the formula below, m represents an integer of 1 to 20, n represents an integer of 1 to 20, provided that (m+n) is an integer of 1 to 30 and the binding sequence of ($CF_2O$) and ($CF_2CF_2O$) is not limited.

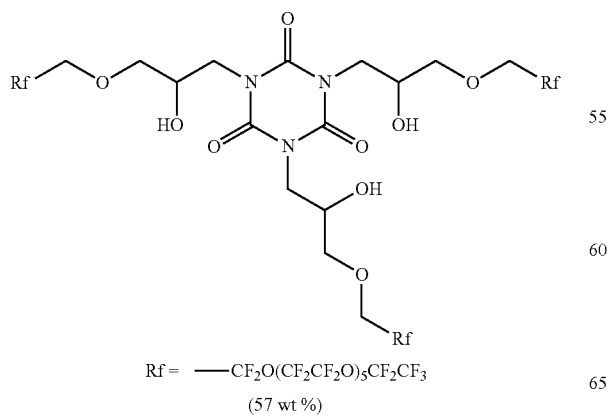

Rf = —$CF_2O(CF_2CF_2O)_5CF_2CF_3$ (57 wt %)

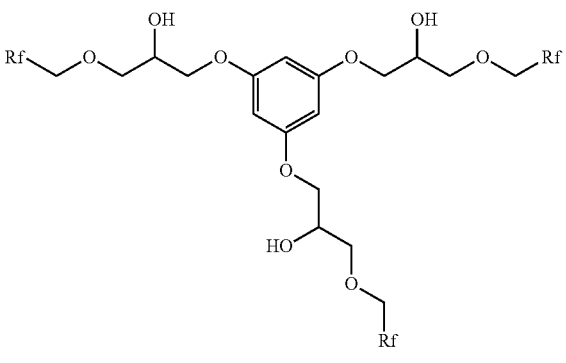

Rf = —$CF_2O(CF_2CF_2O)_5CF_2CF_3$ (57 wt %)

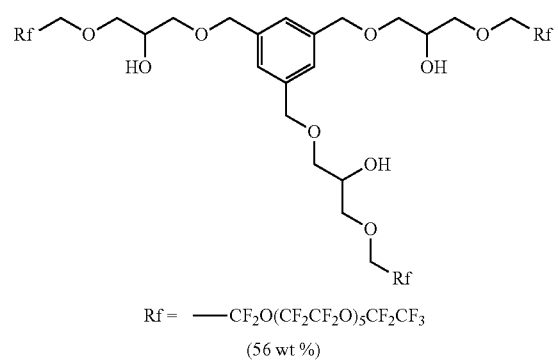

Rf = —$CF_2O(CF_2CF_2O)_5CF_2CF_3$ (56 wt %)

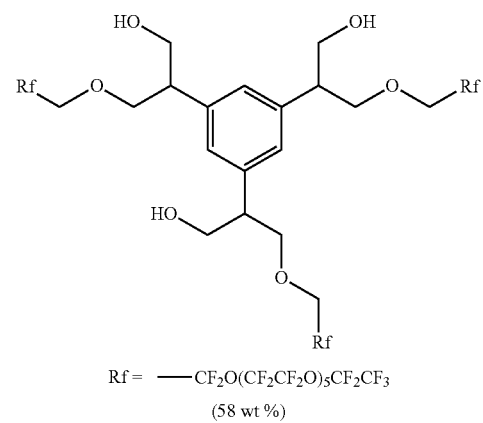

Rf = —$CF_2O(CF_2CF_2O)_5CF_2CF_3$ (58 wt %)

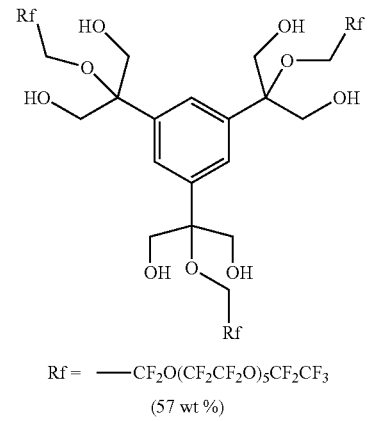

Rf = —$CF_2O(CF_2CF_2O)_5CF_2CF_3$ (57 wt %)

29
-continued
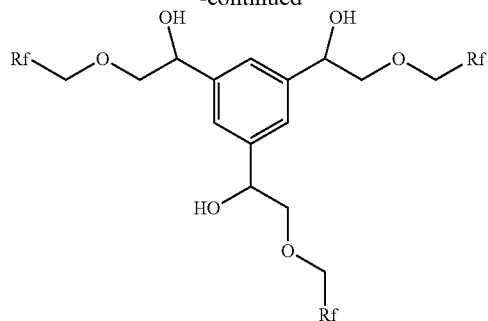
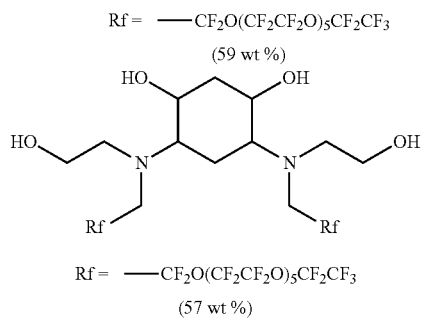
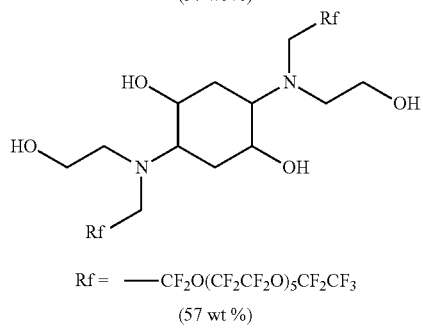
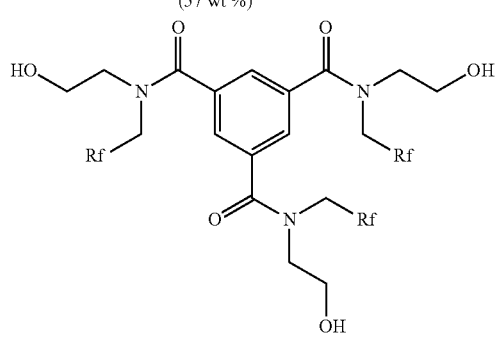
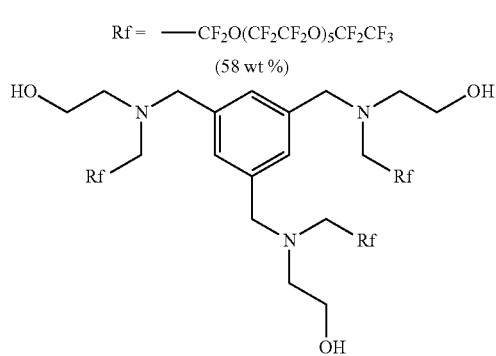
30
-continued
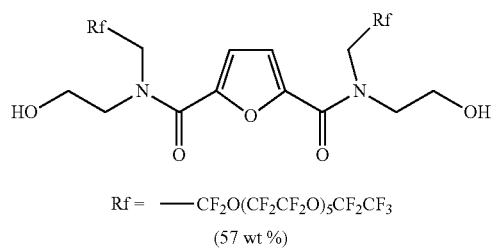
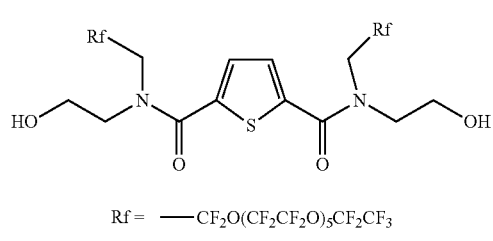
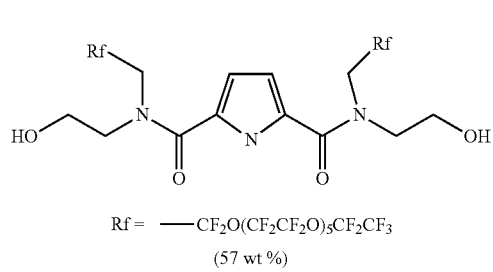
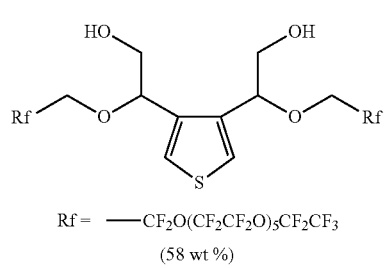
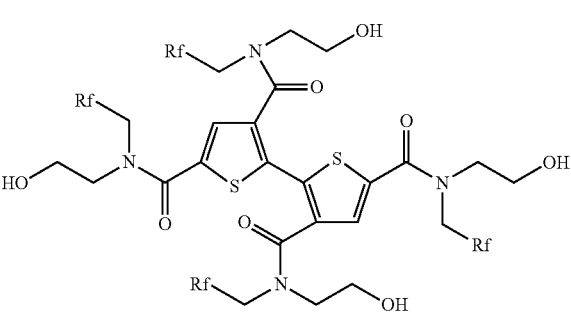

-continued
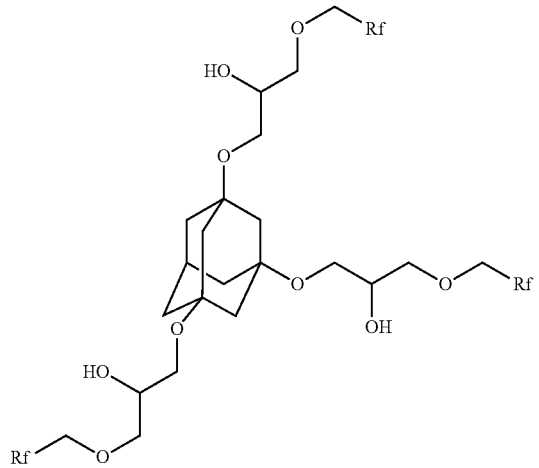
Rf = —CF₂O(CF₂CF₂O)₅CF₂CF₃
(56 wt %)
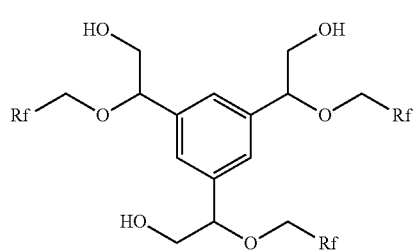
Rf = CF₂O(CF₂CF₂O)₅CF₂CF₃
(59 wt %)
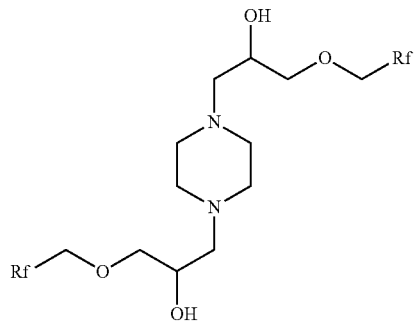
Rf = —CF₂O(CF₂CF₂O)₅CF₂CF₃
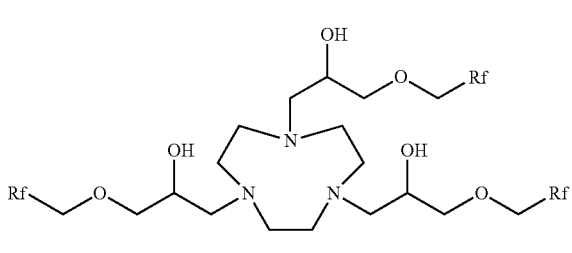
Rf = —CF₂O(CF₂CF₂O)₅CF₂CF₃
(57 wt %)
-continued
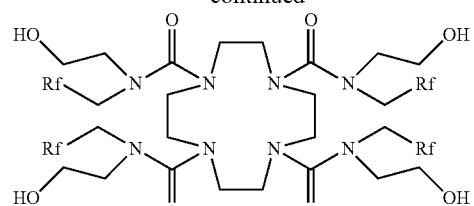
Rf = —CF₂O(CF₂CF₂O)₅CF₂CF₃
(56 wt %)
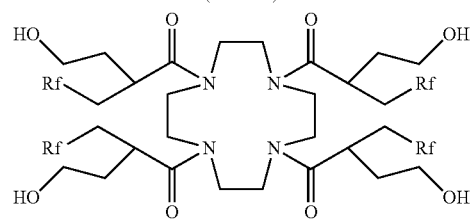
Rf = —CF₂O(CF₂CF₂O)₅CF₂CF₃
(57 wt %)
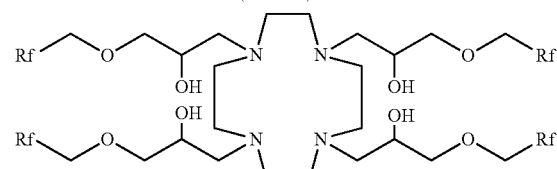
Rf = —CF₂O(CF₂CF₂O)₂CF₂CF₃
(52 wt %)
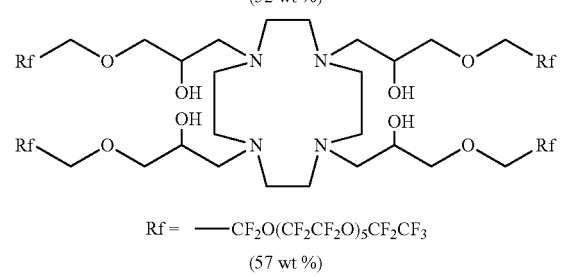
Rf = —CF₂O(CF₂CF₂O)₅CF₂CF₃
(57 wt %)
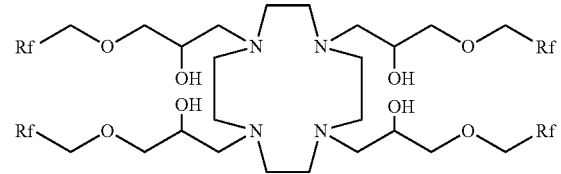
Rf = —CF₂O(CF₂CF₂O)₅CF₂CF(CF₃)₂
(59 wt %)
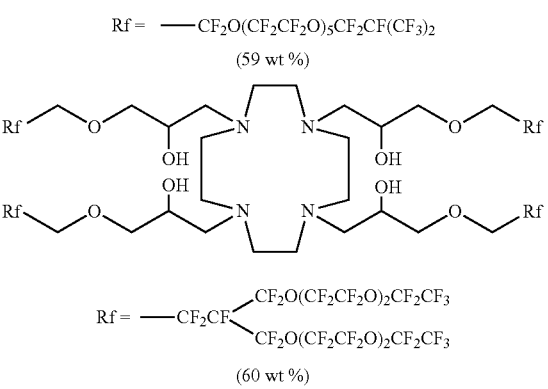
Rf = —CF₂CF⟨CF₂O(CF₂CF₂O)₂CF₂CF₃ / CF₂O(CF₂CF₂O)₂CF₂CF₃⟩
(60 wt %)

33
-continued

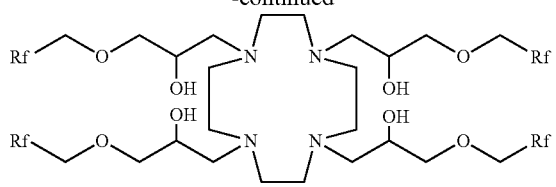

Rf = —CF₂CF$\begin{smallmatrix}CF_2O(CF_2CF_2O)_5CF_2CF_3\\CF_2O(CF_2CF_2O)_5CF_2CF_3\end{smallmatrix}$ (62 wt %)

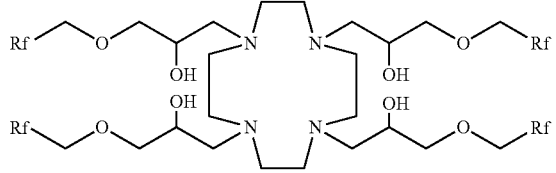

Rf = —CF₂O(CF₂CF₂O)₅CF₂C(CF₃)₃

(60 wt %)

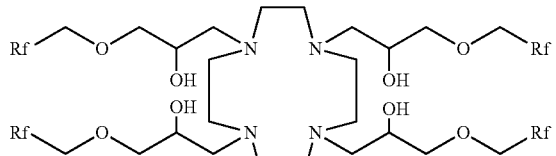

Rf = —CF₂OCF₂OCF₂CF₂OCF₃

(47 wt %)

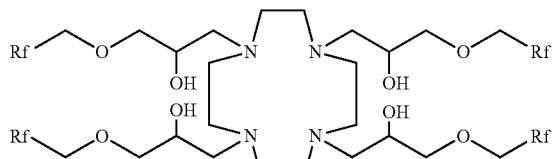

Rf = —CF₂O(CF₂O)$_m$(CF₂CF₂O)$_n$CF₃

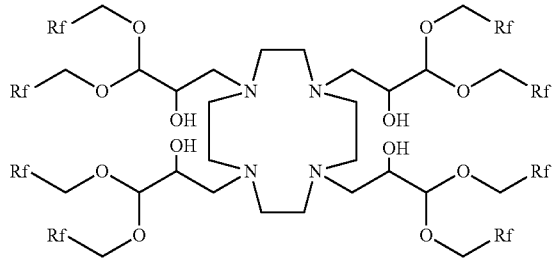

Rf = —CF₂O(CF₂CF₂O)₂CF₂CF₃

(57 wt %)

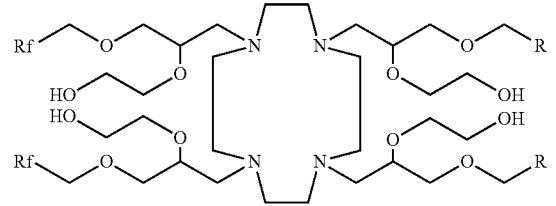

Rf = —CF₂O(CF₂CF₂O)₅CF₂CF₃

(55 wt %)

34
-continued

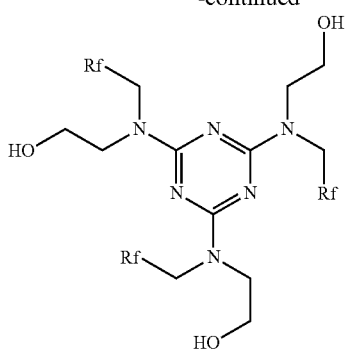

Rf = —CF₂O(CF₂CF₂O)₅CF₂CF₃

(59 wt %)

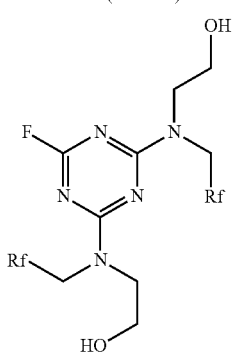

Rf = —CF₂O(CF₂CF₂O)₅CF₂CF₃

(58 wt %)

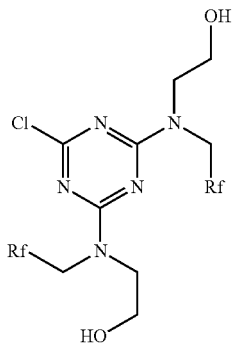

Rf = —CF₂O(CF₂CF₂O)₅CF₂CF₃

(57 wt %)

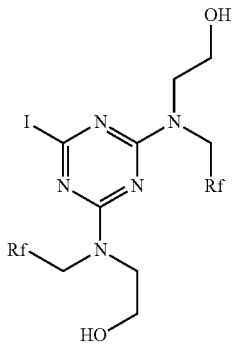

Rf = —CF₂O(CF₂CF₂O)₅CF₂CF₃

(55 wt %)

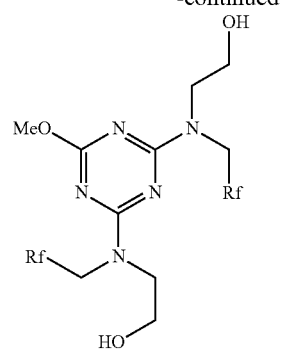
Rf = —CF₂O(CF₂CF₂O)₅CF₂CF₃
(57 wt %)
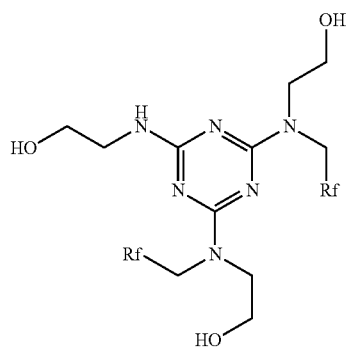
Rf = —CF₂O(CF₂CF₂O)₅CF₂CF₃
(60 wt %)
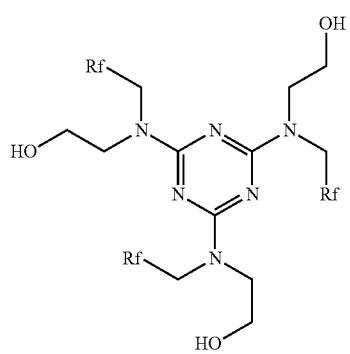
Rf = —CF₂O(CF₂CF₂O)₂CF₂CF₃
(55 wt %)
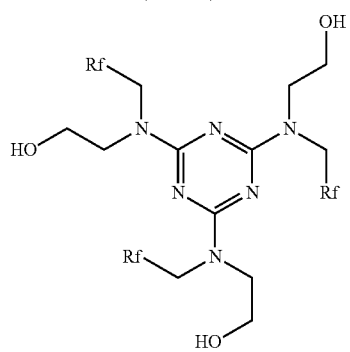
Rf = —CF₂O(CF₂CF₂O)₅CF₂CF(CF₃)₂
(61 wt %)
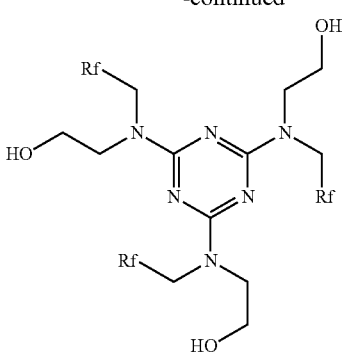
Rf = —CF₂CF⟨CF₂O(CF₂CF₂O)₂CF₂CF₃ / CF₂O(CF₂CF₂O)₂CF₂CF₃⟩
(62 % wt)
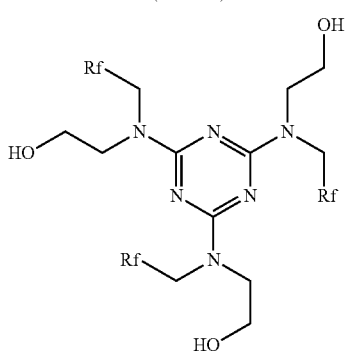
Rf = —CF₂O(CF₂CF₂O)₅CF₂C(CF₃)₃
(62 wt %)
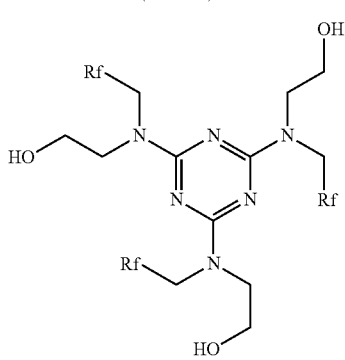
Rf = —CF₂OCF₂OCF₂CF₂OCF₃
(50 wt %)
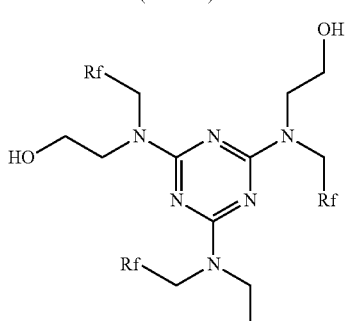
Rf = —CF₂O(CF₂O)ₘ(CF₂CF₂O)ₙCF₃

37
-continued

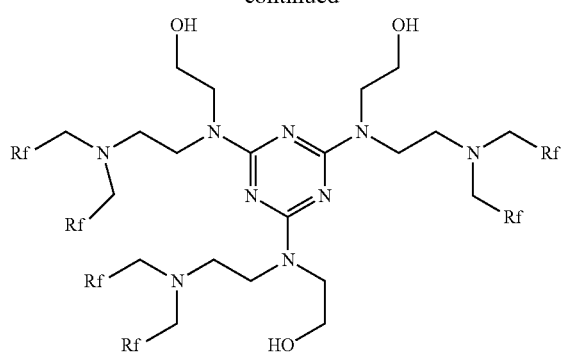

Rf = —CF$_2$O(CF$_2$CF$_2$O)$_2$CF$_2$CF$_3$
(58 wt %)

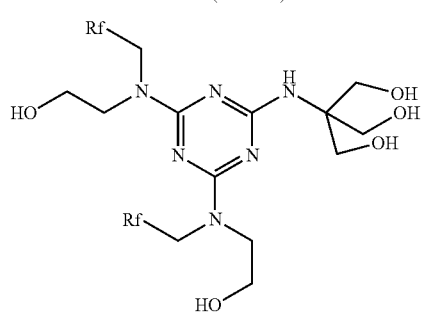

Rf = —CF$_2$O(CF$_2$CF$_2$O)$_5$CF$_2$CF$_3$
(55 wt %)

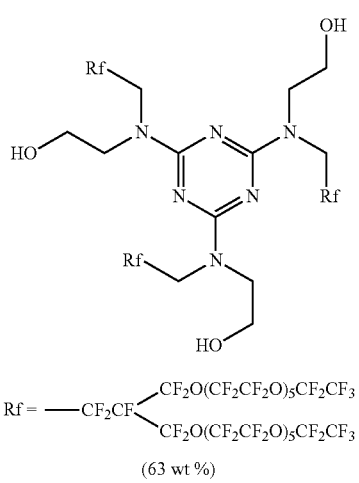

Rf = —CF$_2$CF$\begin{matrix}\text{CF}_2\text{O}(\text{CF}_2\text{CF}_2\text{O})_5\text{CF}_2\text{CF}_3\\\text{CF}_2\text{O}(\text{CF}_2\text{CF}_2\text{O})_5\text{CF}_2\text{CF}_3\end{matrix}$
(63 wt %)

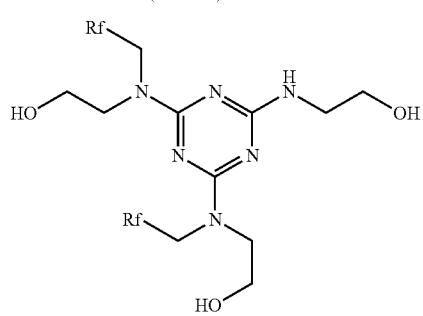

Rf = —CF$_2$O(CF$_2$CF$_2$O)$_5$CF$_2$CF$_3$
(57 wt %)

38
-continued

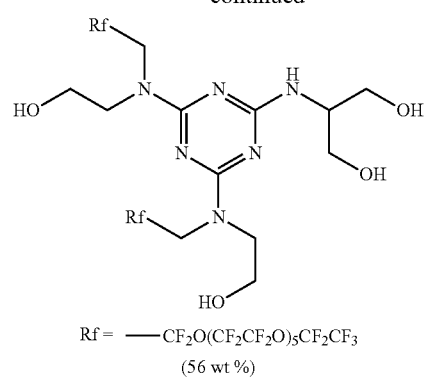

Rf = —CF$_2$O(CF$_2$CF$_2$O)$_5$CF$_2$CF$_3$
(56 wt %)

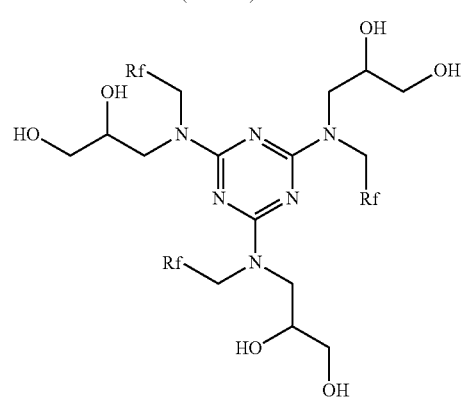

Rf = —CF$_2$O(CF$_2$CF$_2$O)$_5$CF$_2$CF$_3$
(57 wt %)

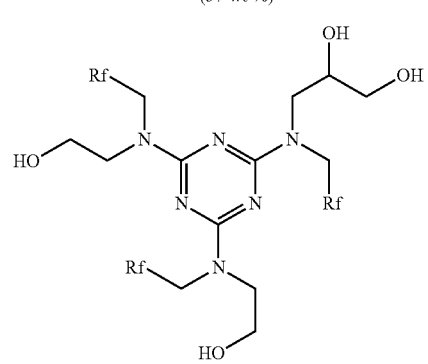

Rf = —CF$_2$O(CF$_2$CF$_2$O)$_5$CF$_2$CF$_3$
(59 wt %)

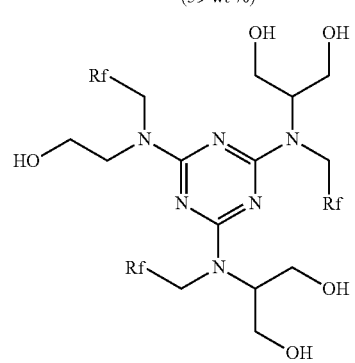

Rf = —CF$_2$O(CF$_2$CF$_2$O)$_5$CF$_2$CF$_3$
(58 wt %)

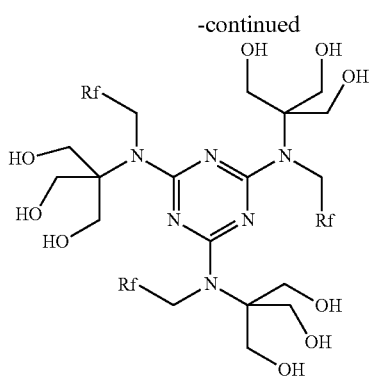

Rf = ——CF₂O(CF₂CF₂O)₅CF₂CF₃
(55 wt %)

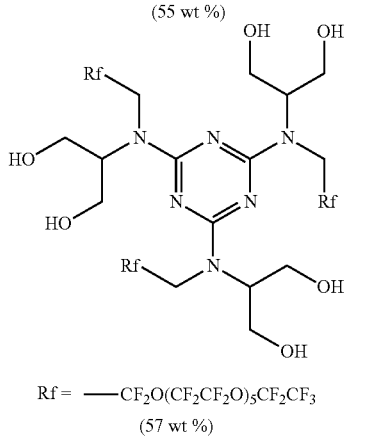

Rf = ——CF₂O(CF₂CF₂O)₅CF₂CF₃
(57 wt %)

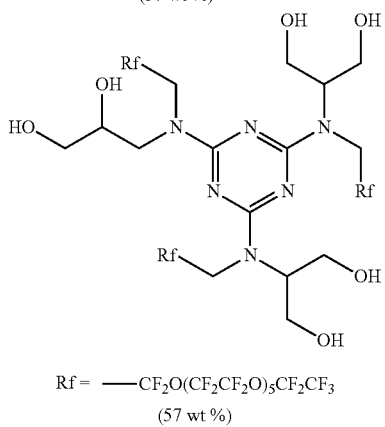

Rf = ——CF₂O(CF₂CF₂O)₅CF₂CF₃
(57 wt %)

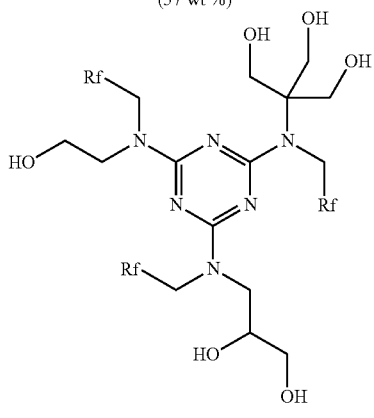

Rf = ——CF₂O(CF₂CF₂O)₅CF₂CF₃
(57 wt %)

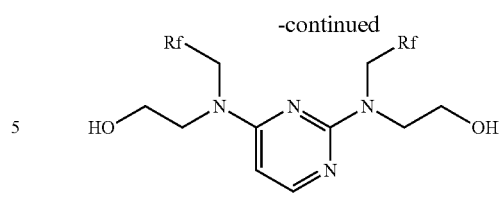

Rf = ——CF₂O(CF₂CF₂O)₅CF₂CF₃
(58 wt %)

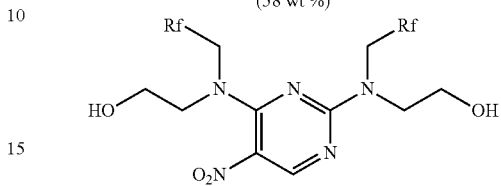

Rf = ——CF₂O(CF₂CF₂O)₅CF₂CF₃
(57 wt %)

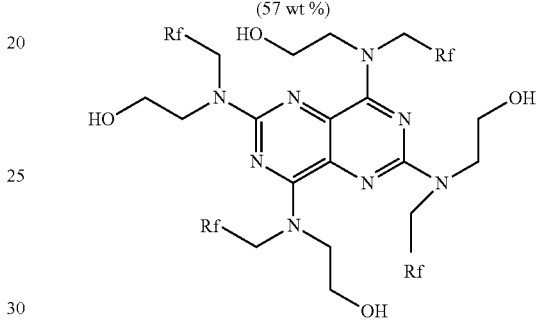

Rf = ——CF₂O(CF₂CF₂O)₅CF₂CF₃
(59 wt %)

The method for synthesizing the compound represented by the formula (1) is not particularly limited, and the compound can be synthesized by a combination of various well-known methods. For example, the basic constituents of the compound represented by the formula (1) is a cyclic group in the center, a perfluoroalkyleneoxy group at the terminal, a linking group linking these groups, or a polar group present in the cyclic group in the center or in the linking group. In respect of multi-point adsorption, it is preferable that a plurality of polar groups be arranged radially with the cyclic group as the center thereof. Accordingly, it is preferable that the polar group be introduced by a predetermined reaction to the linking moiety Y which links the cyclic group to the perfluoroalkyleneoxy group at the terminal.

The perfluoroalkyleneoxy group chain (hereinafter, simply referred to as a "fluorine chain" in some cases) at the terminal greatly changes the polarity of the compound. Therefore, it is preferable that the perfluoroalkyleneoxy group chain be introduced around the final step of the compound synthesis.

For example, the compound represented by any of the formulae (1a), (1b), (1d), and (1e), wherein $W^1$ represents a hydroxyl group or the polar group in $W^1$ is a hydroxyl group, can be synthesized by reacting a cyclic compound containing an epoxy group and an alcohol or amine having a fluorine chain, or the like to form a linking moiety Y. Alternatively, the compound can be synthesized by reacting a cyclic compound having a hydroxyl group, an amino group, or the like (for example, aza-crown) with an epoxy compound having a fluorine chain.

In addition, among the compounds represented by the formulae (1c) and (1f), the compound in which the cyclic group is triazine and k=0 can be synthesized by, for example, reacting an aliphatic amine having a polar group and a fluorine chain with a cyanuric halide. In this reaction, since there are some cases where a reaction between the amine and the cyanuric halide and a reaction between the polar group and the cyanuric halide can be competitive, it is preferable to protect the polar group in advance or introduce the polar group later, depending on the kind of the polar group. Further, the fluorine chain may be introduced in advance or later to the amine.

Examples of the production method for producing the compound of the formula (1) according to the present invention include production methods represented by the following schemes 1 to 3.

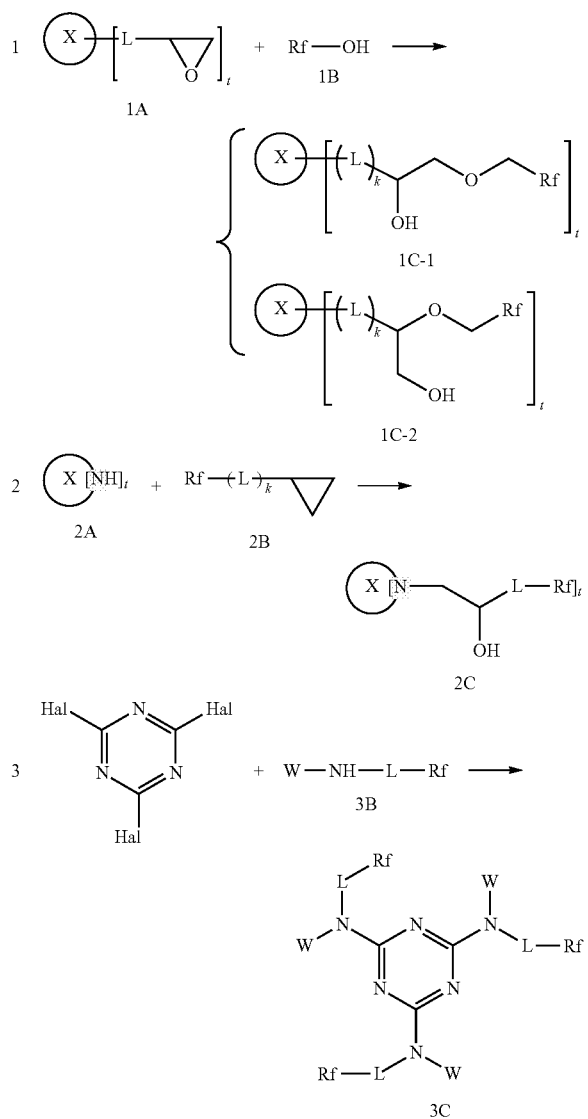

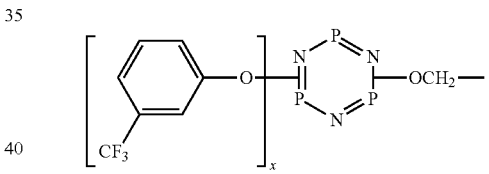

In the formula of each scheme, L is a linking group to be a part of Y in the formula (1), and represents an oxygen atom, an alkylene group, or a combination thereof, or the like, k is 0 or 1, Hal is a halogen atom (for example F, Cl, Br, and I), W is a substituent containing a polar group, Rf represents a perfluoroalkyleneoxy group in the formula (1), and t has the same definition as t in the formula (1).

The scheme 1 is suitable for the synthesis of the compound of the formula (1), in which the cyclic group X is an aromatic aryl group such as a phenyl group or a trione residue of cyanuric acid.

The reagent 2A in the scheme 2 is a cyclic compound that can be X in the formula (1), and means a cyclic compound such as tetraazacyclododecane, containing one or more NH. That is, the scheme 2 is suitable for the synthesis of the compound of the formula (1), in which the cyclic group X is a non-aromatic hetero ring residue containing a nitrogen atom as a ring-constituting atom.

The scheme 3 is suitable for the synthesis of the compound of the formula (1), in which the cyclic group X is a residue of triazine.

The lubricant composition of the invention may contain other compounds according to the uses together with the compound represents by Formula (1), within a range that does not diminish the effect of the invention. For example, the lubricant composition of the invention may contain the following compounds (a) to (d), within a range that does not diminish the effect of the invention. The lubricant composition of the invention may contain 2 or more kinds selected from the following compounds (a) to (d). By the addition of the following compounds (a) to (d), the viscosity of the lubricant composition of the invention is reduced, and as a result, friction (for example, in case of a magnetic recording medium, reduction in friction between a head and media) is intended to be further reduced.

$$A\text{-}CF_2O(CF_2CF_2O)_r(CF_2O)_sCF_2\text{-}B \tag{a}$$

[A and B independently represent $OHCH_2$— or at least one kind of group selected from the following formula; r is any number from 1 to 30; and s is any number from 1 to 30;

$$\left[\begin{array}{c}\text{\scriptsize benzene with }CF_3\end{array}\text{-O-}\begin{array}{c}\text{\scriptsize phosphazene ring}\end{array}\text{-OCH}_2\text{---}\right]_x$$

here, x is any number from 1 to 5]

$$X\text{---}CF_2O(CF_2CF_2O)_m(CF_2O)_nCF_2\text{---}Y \tag{b}$$

[X and Y independently represent a group selected from F, $HO(CH_2CH_2O)_tCH_2$—, $HOCH_2CH(OH)CH_2OCH_2$—, HOOC—, and a piperonyl group; m is any number from 1 to 60; n is any number from 1 to 60; and t is any number from 1 to 30]

$$F[CF(CF_3)CF_2O]_uCF(CF_3)\text{---}X' \tag{c}$$

[X' represents F or COOH—; and u is any number from 1 to 60]

$$F[CF_2CF_2CF_2O]_vCF_2CF_2CH_2\text{---}Z \tag{d}$$

[Z represents a group selected from F, HO—, and COOH—; and v is any number from 1 to 60]

Examples of the compound of the Formula (a) include "Fomblin Z-dol" (manufactured by Solvay Solexis, Inc.), "MORESCO PHOSFAROL A20H" (manufactured by MATSUMURA OIL RESEARCH CORP.), and the like. Examples of the compound of the Formula (b) include "Fomblin Z-03", "Z-dol TX", "Z-tetraol", "Z-DIAC", "AM2001", "AM3001" (all manufactured by Solvay Solexis, Inc.), and the like. Examples of the compound of Formula (c) include "KRYTOX 143", "157FS" (manufactured by DuPont), and the like.

Examples of the compound of Formula (d) include "DemnumSA", "DemnumSH" (all manufactured by DAIKIN INDUSTRIES, Ltd.), and the like.

The lubricant composition of the invention may be prepared as a coating liquid including a solvent. In an embodiment in which the lubricant composition is used as a material for a lubricating layer of a magnetic recording medium and the like, it is preferable to prepare the lubricant composition as a coating liquid and to form a thin layer (about 5 Å to 20 Å) by coating the coating liquid on the surface of a substrate or the like. There is no particular limitation on the solvent used for the preparation of the coating liquid. For example, commercially available products such as "Vertrel XF-UP" (manufactured by Du Pont-Mitsui Fluorochemicals Co., Ltd.), "HFE-7100DL" (manufactured by Sumitomo 3M, Ltd.), "HFE-7200" (manufactured by Sumitomo 3M, Ltd.), "AK-225" (manufactured by ASAHI GLASS CO., LTD.), acetone, and 2-butanone can be used. The concentration of the compound of formula in the coating liquid can be determined according to the thickness of the layer to be formed, coating amount, and the like, but the concentration is generally about 0.001% to 0.5% by mass.

2. Film and Laminate

The invention also relates to a film formed of the lubricant composition of the invention. The film of the invention can be formed by preparing the lubricant composition of the invention as a coating liquid and coating the coating liquid on the substrate surface, for example. There is no particular limitation on the coating method, and the film can be formed by a well-known method. Specifically, various coating methods such as a dip coating method, a spin coating method, a dip spin method, and an LB method can be used. The film can also be formed by vacuum deposition. In an embodiment in which the film of the invention is used as a lubricating layer of a magnetic recording medium such as a magnetic recording disk, or as a lubricating layer of a magnetic recording head, a film showing the excellent state of the coated surface is required to be formed as a thin film (for example, a thickness of about 5 Å to 20 Å). For the use, it is preferable to use a dip coating method, a spin coating method, and vacuum deposition, and particularly, the dip coating method is preferable.

Though there is no particular limitation on the solvent used for the preparation of a coating liquid, in the case of dip coating method, it is preferable to use a fluorine-based solvent such as "Vertrel XF-UP" (manufactured by Du Pont-Mitsui Fluorochemicals Co., Ltd.), "HFE-7100DL" (manufactured by Sumitomo 3M, Ltd.), "HFE-7200" (manufactured by Sumitomo 3M, Ltd.) for the preparation, among the above-described solvents.

There is no particular limitation on a substrate for forming the film of the invention, and the substrate can be selected according to the use. An example of the substrate includes a substrate in which at least a portion of the surface thereof includes carbon such as diamond-like carbon as a main material. When the lubricant composition of the invention is coated on the surface of the substrate including carbon such as diamond-like carbon as a main material, it is assumed that in the compound of the Formula (1), the cyclic group X as the center core thereof is oriented horizontally to the substrate surface, and the perfluoropolyether (PFPE) chain as the side chain thereof is oriented vertically. As a result, a particularly high lubricating performance is expected to be expressed. For example, when the lubricant composition (containing a compound that includes —$(OCF_2CF_2)_kOC_nF_{2n+1}$ (here, k+n is 8 or less, and k is 6 or less) at the terminal, as the compound of Formula (1)) of the invention is prepared as a coating liquid by using a fluorine-based solvent, and a film is formed by a dip coating method on the substrate surface formed of diamond-like carbon, in a FT-IR RAS spectrum of the film, a very strong peak attributed to a $CF_3$ group is created near 1260 $cm^{-1}$ (specifically, a range of ±5 $cm^{-1}$). On the other hand, when the same compound is formed as an LB monolayer film, and the FT-IR RAS spectrum is measured in the same manner, a very strong peak attributed to the $CF_3$ group is created near 1260 $cm^{-1}$ (specifically, a range of ±5 $cm^{-1}$). That is, from these results, it can be mentioned that the state of the molecules of the compound of Formula (1) in the film that is formed on the surface formed of carbon is the same as the state of the compound in the LB monolayer film. It is considered that the LB monolayer film is formed in a state in which hydrophilic or polar portions in the molecule face a water surface, and hydrophobic portions of the perfluoropolyether (PFPE) chain converge and are concentrated in an air interface side. Accordingly, the molecules of the compound of Formula (1) in the film that is formed on the surface formed of carbon are also assumed to form a film, in a state in which the PFPE chain is oriented vertically with respect to the substrate surface and concentrated. The uniformity of the molecular state between the LB monolayer film and the compound of Formula (1) can be confirmed from a result that the strength of the peak attributed to the $CF_3$ group near 1260 $cm^{-1}$ is equal to or greater than 50% of the strength of the same peak of the LB monolayer film. The peak strength could be identical in some cases, that is, could be 100%.

In all compounds for a lubricant used for a magnetic recording medium, which are used in the related art and include the PFPE chain, the long PFPE chain is oriented horizontally with respect to the substrate surface. The present inventors consider that such a property is a cause of limiting the performance of the lubricant in the related art. As described above, in the lubricant composition of the invention, the PFPE chain is oriented vertically, and for example, the $CF_3$ group positioned at the terminal of the PFPE chain is present in the uppermost surface of the lubricating layer that contacts a magnetic head. On the other hand, in the compound of the related art in which the PFPE chain is oriented horizontally with respect to the substrate surface, an alkylenoxy fluoride group such as $CF_2CF_2O$ is present on the uppermost surface of the lubricating layer. Compared to this state, a state in which the $CF_3$ group forms the uppermost surface of the lubricating layer is expected to further reduce the surface energy stochastically.

As described above, in the past, there was a problem in that —$OCF_2O$— was degraded in the presence of aluminum oxide ($\alpha$-$Al_2O_3$) that was a constituent component of a magnetic head. If the PFPE chain is oriented vertically, it is possible to arrange —$OCF_2O$— far away from the magnetic head. In addition, in the lubricant "FOMBLIN Z-TETRAOL" manufactured by Ausimont, Inc., when a polar adsorptive group is present at both terminals of the chain-like PFPE chain, the polar adsorptive group may interact with the adjacent adsorptive groups at the PFPE chain terminal. However, when the adsorptive groups at both terminals of the same molecule interact with each other, if the adsorptive groups are adsorbed onto the substrate surface, the film thickness becomes half of the chain-like PFPE chain at the maximum, and becomes approximately the thickness of —$(CF_2CF_2O)_{10}$— provided that the average molecular weight is 2000. Consequently, concerns over the creation of the lubricating layer looking like a densely wooded plain cannot be dispelled, and it is easy to imagine —$OCF_2O$— being degraded and transferred to the head. Therefore, the lubricating technique in the related art based on the premise of the horizontal orientation of the chain-like PFPE chain can be mentioned as a technique that has limitations for meeting the requirement for making the film thinner.

In respect of the adsorption efficiency, 2 chain-like PFPE chains are arranged in the molecule at the maximum. However, if the molecule has a structure in which 3 or more of the PFPE chains are radially arranged from the center of the molecule, and the adsorptive groups are arranged in the center core or the junction between the PFPE chain and the center core, it is easy to provide the adsorptive group with three or more adsorption points, and the chain-like PFPE chain can be expected to yield a preferable adsorption effect. In this case, by dividing the PFPE chain into a plurality of side chains, the length can be shortened, which is expected to directly lead to thinning of the lubricating layer. Particularly, if the center core is made into a flat cyclic structure, the substrate surface itself serves as an anisotropic field, and the flat cyclic structure, that is, a disk-like structure also has anisotropic property and planarity. Therefore, when the adsorptive group as a polar group is present near the disk surface, it would be enthalpically stable if the adsorptive group is oriented horizontally along the substrate surface. Meanwhile, a fact that the PFPE chain which extends radially from the disk surface also has a water-repellent property and oil-repellent property and tends to extend in a direction away from a polar surface, that is, extend vertically with respect to the substrate surface has been confirmed particularly in the LB monolayer film of a disk-like molecule that includes a hydrophobic side chain (see Kawata, K., The Chemical Record, Vol. 2, pp 59-80 (2002)).

As described above, the molecule of the compound of the Formula (1) can form a film on the surface of a carbon material such as diamond-like carbon, by vertically orienting and concentrating the PFPE chain. As a result, compared to the compound for lubricant in the related art, which includes the PFPE chain oriented horizontally, the compound of Formula (1) is expected to improve in all respects such as lubricating property, adsorptiveness, and durability.

In the use of a laminate that includes a lubricating film on a substrate in which at least a portion of the surface includes carbon as a main material, a magnetic recording medium, a head slider, and the like described later are included.

Hereinafter, as an example, a method of forming a lubricating film formed of the lubricant composition of the invention on a protective layer of a magnetic recording medium will be described.

An example of the method of forming the lubricating film on the protective layer of the magnetic recording medium includes 3 steps such as a pre-treatment step, a coating step, and a post-treatment step.

The purpose of the pre-treatment step is to wash and activate the protective layer surface, and the method thereof is not particularly limited. Examples of the method include UV irradiation, a plasma treatment, and the like. If the protective layer surface is sufficiently cleaned and activated, the pre-treatment step can be omitted.

The coating step is a step of coating the protective layer surface of the magnetic recording medium having undergone the pre-treatment with the lubricant composition, and forming a lubricating layer. The coating method is the same as the example of the film formation method described above. For the lubricating film of the magnetic recording medium, it is required that a film showing an excellent coated surface state is formed into a thin film (for example, a thickness of about 5 Å to 20 Å). In order to meet this requirement, it is preferable to form the film by using a dip coating method, a spin coating method, and vacuum deposition. Particularly, if the dip coating method is used, while a substrate is dipped in coating liquid of the lubricant composition, the compound of the Formula (1) is adsorbed onto and oriented in the protective layer surface. Accordingly, the dip coating method is particularly desirable.

The solvent used for the preparation of the coating liquid is the same as the solvent described above. To the coating liquid, other compounds (for example, other fluorine-based lubricants and the like) may be added according to the use, within a range that does not diminish the effect of the invention.

The purpose of the post-treatment step is to promote the lubricant composition to be adsorbed onto the protective layer surface. There is no particular limitation on the post-treatment method, but annealing, UV irradiation, and the like are preferable as the method. As an annealing condition, a temperature of 50° C. to 150° C. is preferable, and in a case of UV irradiation, it is preferable to use a UV lamp including light of wavelengths of 185 nm and 254 nm.

The lubricant composition of the present invention shows not only the above-described effect but also the unpredictable property of which absorbable ability to a substrate is improved by being subjected to ultraviolet-irradiation, and it is excellent in terms of the unpredictable property. The lubricant film formed by using the lubricant composition of the invention is intrinsically excellent in the absorbable ability, and is useful even without any modification; and furthermore, the lubricant film is preferably used after being subjected to ultraviolet irradiation for enhancing the absorbable ability.

3. Magnetic Recording Medium

The lubricant composition of the invention is useful as a lubricant composition for a magnetic recording medium.

Hereinafter, the magnetic recording medium of the invention that uses the lubricant composition of the invention will be described.

The lubricant composition of the invention is suitable as a material of a lubricating layer of a magnetic recording medium such as a magnetic recording disk and a magnetic tape. In the present specification, the "magnetic recording medium" includes all of a magnetooptical recording medium such as MO that concurrently uses magnetism and light, and a heat-assisted type recording medium that concurrently uses magnetism and heat, in addition to a hard disk, a Floppy (registered trademark) disk, a magnetic tape, and the like that only use magnetism for recording and reading information.

FIG. 1 is a schematic cross-sectional view of an example of a magnetic recording disk which is an embodiment of the magnetic recording medium of the invention. The relative relationship between the thicknesses of the respective layers may not match with the relationship of the actual magnetic recording disk in some cases. The magnetic recording disk shown in FIG. 1 includes a substrate 1 formed of an aluminum alloy or the like, and a plating film 2 of Ni—P or the like coated on the substrate 1 as a hard base layer. The magnetic recording disk also includes a base film layer 3 that is formed on the plating film 2 by sputtering or the like and is a metal film such as Cr; a magnetic recording layer 4 that is formed of a metal alloy such as a Co—Cr—Ta alloy; and a protective film layer 5 that is formed by the deposition of carbon such as diamond-like carbon. On the protective film layer 5, a lubricating layer formed of the lubricant composition of the invention is formed. The protective film layer 5 and the lubricating layer 6 reduce the abrasion damage of a disk and a head, which is caused, for example, when the magnetic head and the disk perform contact-slide at a high speed. Since the lubricating layer 6 is formed of the lubricant composition of the invention, the lubricating layer 6 is excellent in terms of adsorptiveness with respect to the protective layer and the surface smoothness, and shows a superior lubricating property. Consequently, head contamination is reduced, and the abrasion damage caused during the contact-slide between the disk and head is also reduced, whereby a magnetic recording disk with high reliability can be obtained.

The lubricant composition of the invention is also useful for forming a lubricating film of DTM (Discrete Track Media) and BPM (Bit Patterned Media). The lubricant composition of the invention has characteristics such as high viscosity and low vapor pressure property. Therefore, particularly in a process in which a concave-convex shape of the surface is not refilled, the lubricant composition can reduce the transfer of a non-adsorptive lubricant that excessively accumulates in a concave portion to the head, and the movement of the non-adsorptive lubricant to the surface of a data portion.

The lubricant composition of the invention is also useful as a lubricating film for heat-assisted recording of assisting energy and microwave-assisted recording. Particularly, since the lubricant composition of the invention has excellent heat durability, the lubricant composition is useful as a lubricating film for heat-assisted magnetic recording.

4. Head Slider

The invention also relates to a head slider that is provided with a magnetic head and includes a lubricating film formed of the lubricant composition of the invention on at least a portion of the surface. If the lubricating film is formed on the magnetic head surface, it is possible to reduce the friction force caused when the head contacts the disk. In addition, the compound of Formula (1) contained in the lubricant composition of the invention has a property in which the compound can coat the substrate surface with high density. Accordingly, the reduction in the contaminant attachment to the head is expected.

As a method of forming the lubricating film formed of the lubricant composition of the invention on the head slider surface, it is possible to use the above-described method of forming the lubricating film which is formed on the protective layer of the magnetic recording medium, and the preferable embodiment thereof is also the same. Moreover, the film thickness is also about the same as the film thickness of the lubricating film formed on the magnetic recording medium.

Between the head slider surface and the lubricating film formed of the lubricant composition of the invention, a protective layer may be formed. Similar to the protective layer of the magnetic recording medium, the protective layer is preferably formed by the deposition of carbon such as diamond-like carbon. The molecules of the compound of Formula (1) which is contained in the lubricant composition of the invention are preferable since the molecules show high adsorptiveness with respect to a surface formed of the material, and the PFPE chain can be oriented vertically and form a film by being concentrated, as described above.

The present invention also relates to a magnetic recording medium having a film including the lubricant composition of the present invention, and a magnetic recording medium having at least one of the head sliders having a film including the lubricant composition of the present invention. Since the magnetic recording device of the present invention has a film including the lubricant composition as a lubricating film, an effect of inhibiting the contamination of the head is excellent. Therefore, the present invention is effective particularly in an embodiment of a magnetic recording device having a high recording density, in which the head contamination becomes remarkable and the head floating amount is small.

EXAMPLES

Hereinafter, the present invention will be described in more detail with reference to Examples. The materials, reagents, ratios, operations, and the like shown in Examples shown below can be appropriately modified as long as the modification does not depart from the spirit of the present invention. Consequently, the range of the present invention is not limited to Examples shown below.

Herein, the nuclear magnetic resonance method is denoted as NMR, high performance liquid chromatography is denoted as HPLC, the matrix-assisted laser desorption and ionization method is denoted as MALDI, and the time of flight spectrometry is denoted as TOF. In $^1$H-NMR, the measurement was carried out using tetramethylsilane (TMS) as an internal standard. For $^{19}$F-NMR, the measurement was carried out using fluorotrichloromethane as an external standard.

1. Synthesis Example of Compound

Example 1

Synthesis of Compound (3)

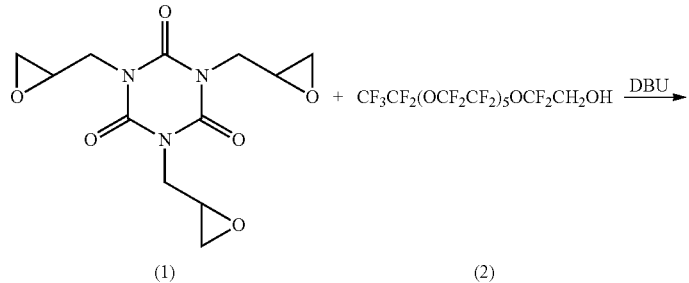

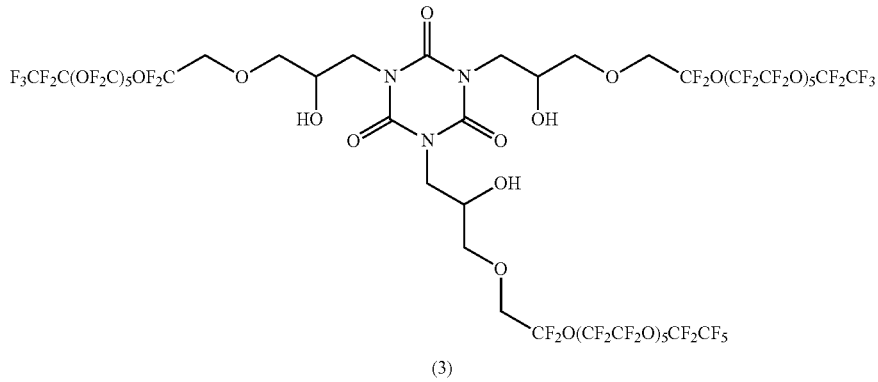

223 mg (0.75 mmol) of a compound (1) and 1.97 g (2.48 mmol) of a compound (2) were placed in a reaction vessel made of glass, and 13.7 mg (0.09 mmol) of 1,8-diazabicyclo[5.4.0]undec-7-ene (DBU) was added thereto. The mixture was reacted at 100° C. for 2 hours, and then purified by silica gel column chromatography to obtain 706 mg (0.263 mmol, yield 35.1%) of a compound (3).

Data for Identification of Compound (3):

$^1$H-NMR [CDCl$_3$]: δ [ppm]=3.50 (3H, m), 3.67 (3H, t, J=8.7 Hz), 3.83 (6H, d, J=4.2 Hz), 3.94 (6H, m), 4.78 (3H, m), 5.03 (3H, s).

$^{19}$F-NMR [CDCl$_3$]: δ [ppm] −88.8(66F, m), −86.9(9F, s), −77.9(6F, m).

Example 2

Synthesis of Compound (5)

7-ene (DBU) was added thereto. The mixture was reacted at 100° C. for 10 hours. After being left to cool, the mixture was subjected to liquid separation with ethyl acetate-15 wt % brine-FC-72 (trade name, manufactured by Sumitomo 3M Limited), and the FC-72 layer was dried over sodium sulfate. After filtration, the solvent was evaporated under reduced pressure, and the residue was purified by silica gel column chromatography to obtain 274 mg (0.102 mmol, yield 7.5%) of a compound (5).

Data for Identification of Compound (5)

$^1$H-NMR [CDCl$_3$]: δ [ppm]=2.38 (3H, d, J=3.6 Hz), 3.78 (6H, m), 3.90 (6H, t, J=7.5 Hz), 3.98 (6H, d, J=4.2 Hz), 4.15 (3H, m), 6.11 (3H, s).

$^{19}$F-NMR [CDCl$_3$]: δ [ppm] −88.9 (66F, m), −87.0 (9F, s), −78.0 (6F, m).

MALDI/TOF-MS: m/z=2704.2 [M$^+$+Na].

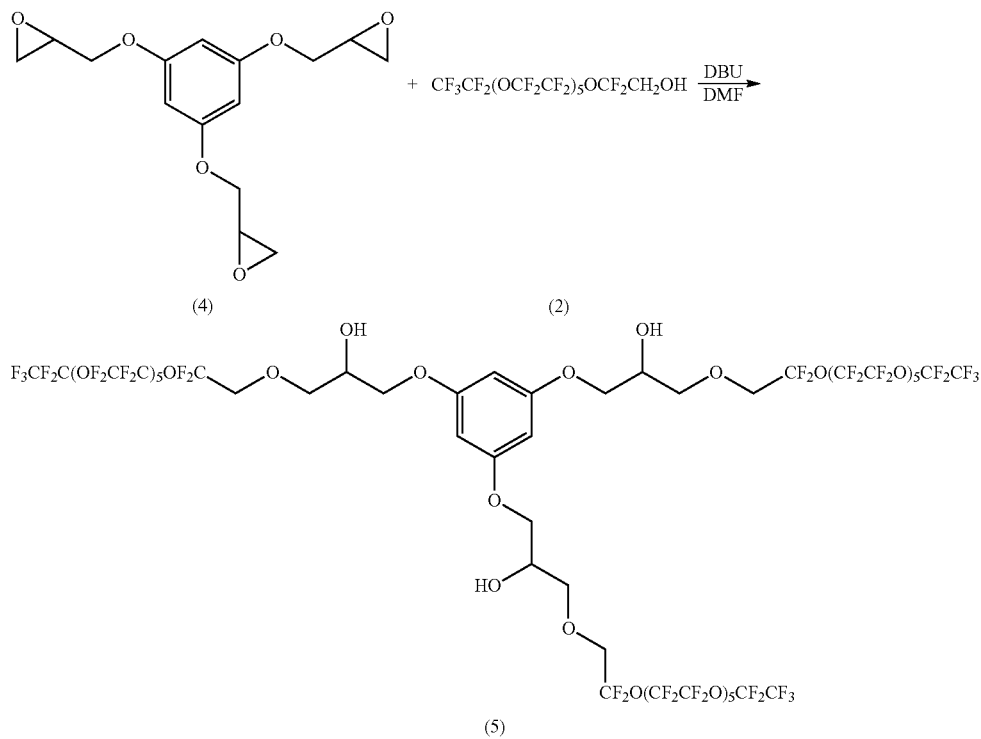

400 mg (1.36 mmol) of a compound (4), 1 mL of N,N-dimethylformamide (DMF), and 3.57 g (4.49 mmol) of the compound (2) were placed in a reaction vessel made of glass, and 24.8 mg (0.163 mmol) of 1,8-diazabicyclo[5.4.0]undec-

Example 3

Synthesis of Compound (8)

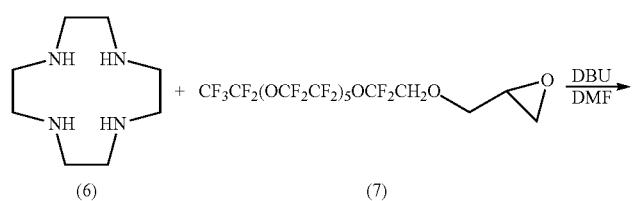

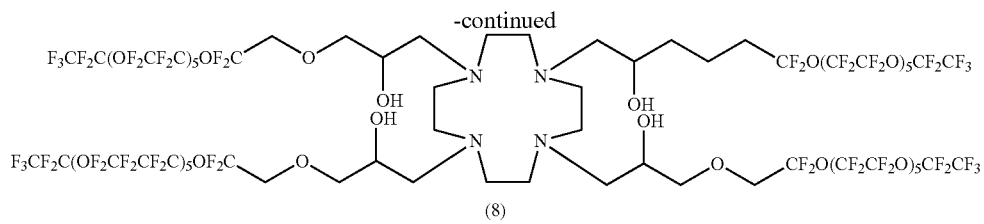

(8)

59 mg (0.343 mmol) of a compound (6), 1.29 g (1.51 mmol) of a compound (7), and 1 mL of N,N-dimethylformamide (DMF) were placed in a reaction vessel made of glass, and the mixture was reacted at 100° C. for 8 hours. After being left to cool, the mixture was subjected to liquid separation with ethyl acetate-15 wt % brine-FC-72, and the FC-72 layer was dried over sodium sulfate. After filtration, the solvent was evaporated under reduced pressure, and the residue was purified by silica gel column chromatography to obtain 794 mg (0.222 mmol, yield 64.6%) of a compound (8).

Data for Identification of Compound (8)

$^1$H-NMR [CDCl$_3$]: δ [ppm]=2.00-2.99 (24H, m), 3.59 (8H, m), 3.88 (12H, m).

$^{19}$F-NMR [CDCl$_3$]: δ [ppm] −90.1 to −87.1 (100F), −79.0 to −78.4 (8F).

MALDI/TOF-MS: m/z=3580.3 [M$^+$].

Example 4

Synthesis of Compound (10)

![Reaction scheme showing compound (6) cyclen + compound (9) CF$_3$CF$_2$(OCF$_2$CF$_2$)$_2$OCF$_2$CH$_2$O-epoxide with DBU/DMF yielding compound (10)]

(1.51 mmol) of the compound (7), 519 mg (0.237 mmol, yield 69.3%) of a compound (10) was obtained.

Data for Identification of Compound (10)

$^1$H-NMR [CDCl$_3$]: δ [ppm]=1.98-2.98 (24H, m), 3.58 (8H, m), 3.89 (12H, m).

$^{19}$F-NMR [CDCl$_3$]: δ [ppm] −89.9 to −86.9 (52F), −78.8 to −78.5 (8F).

MALDI/TOF-MS: m/z=2189.2 [M$^+$].

Example 5

Synthesis of Compound (12)

In the same manner as in Example 3 except that 761 mg (1.51 mmol) of the compound (9) was used instead of 1.29 g ![Reaction scheme showing compound (6) + compound (11) with DBU/DMF]

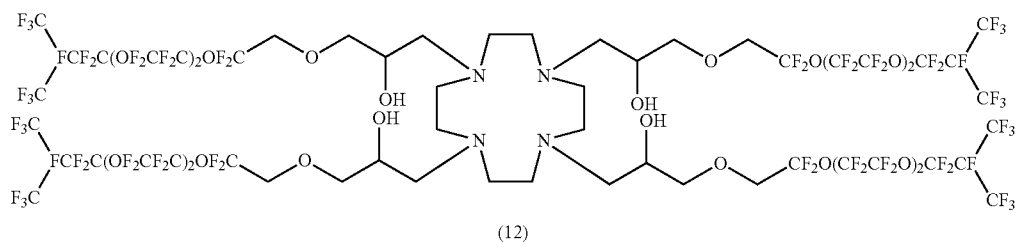

(12)

In the same manner as in Example 3 except that 912 mg (1.51 mmol) of the compound (11) was used instead of 1.29 g (1.51 mmol) of the compound (7), 610 mg (0.237 mmol, yield 68.7%) of a compound (12) was obtained.

Data for Identification of Compound (12)

$^1$H-NMR [CDCl$_3$]: δ [ppm]=1.98-2.99 (24H, m), 3.60 (8H, m), 3.89 (12H, m).

$^{19}$F-NMR [CDCl$_3$]: δ [ppm] −189.4 to −188.8 (4F), −89.8 to −87.0 (32F), −78.8 to −78.5 (8F), −77.2 to −76.7 (8F), −73.8 to −73.4 (24F).

MALDI/TOF-MS: m/z=2589.2 [M$^+$].

Example 6

Synthesis of Compound (14)

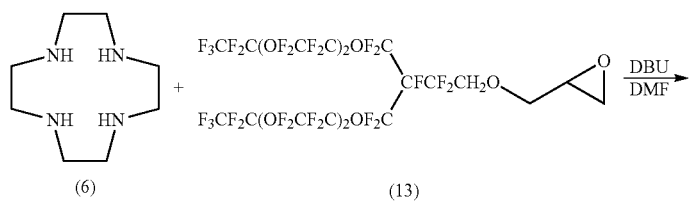

(6)    (13)

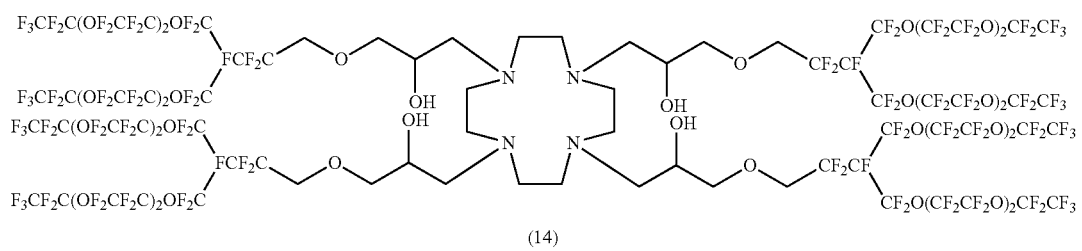

(14)

In the same manner as in Example 3 except that 1.51 g (1.51 mmol) of the compound (13) was used instead of 1.29 g (1.51 mmol) of the compound (7), 865 mg (0.207 mmol, yield 60.3%) of a compound (14) was obtained.

Data for Identification of Compound (14)

$^1$H-NMR [CDCl$_3$]: δ [ppm]=1.98-2.98 (24H, m), 3.58 (8H, m), 3.89 (12H, m).

$^{19}$F-NMR [CDCl$_3$]: δ [ppm] −186.1 to −183.2 (4F), −121.9 to −124.7 (8F), −90.2 to −86.9 (120F).

MALDI/TOF-MS: m/z=4181.7 [M$^+$].

Example 7

Synthesis of Compound (20)

(7-1) Synthesis of Compound (17):

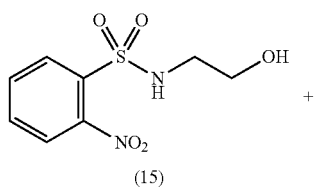

(15)

+

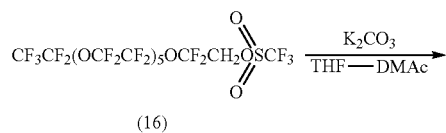

(16)

-continued

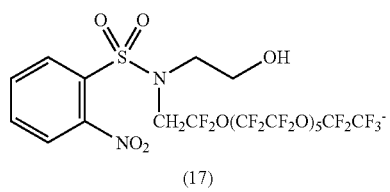

1.50 g (6.09 mmol) of a compound (15) was placed in a reaction vessel made of glass, and dissolved in 6 mL of tetrahydrofuran (THF) and 6 mL of N,N-dimethylacetamide (DMAc). 1.70 g (12.2 mmol) of potassium carbonate and 8.72 g (9.39 mmol) of a compound (16) were added thereto, and the mixture was reacted at 80° C. for 1 hour. After being left to cool, the mixture was subjected to liquid separation with ethyl acetate-water. The organic layer was washed with 10 wt % brine and 25 wt % brine, and dried over sodium sulfate. After filtration, the solvent was evaporated under reduced pressure, and the residue was purified by silica gel column chromatography to obtain 1.18 g (1.17 mmol, yield 19.3%) of a compound (17).

Data for Identification of Compound (17)

$^1$H-NMR [CDCl$_3$]: δ [ppm]=1.79 (1H, t, J=5.4 Hz), 3.61 (2H, t, J=5.1 Hz), 3.77 (2H, m), 4.16 (2H, t, 10.2 Hz), 7.73 (3H, m), 8.13 (1H, m).

$^{19}$F-NMR [CDCl$_3$]: δ [ppm] −88.7 (22F, m), −86.9 (3F, s), −73.3 (2F, m).

MALDI/TOF-MS: m/z=1046.9 [M$^+$+Na].

(7-2) Synthesis of Compound (18):

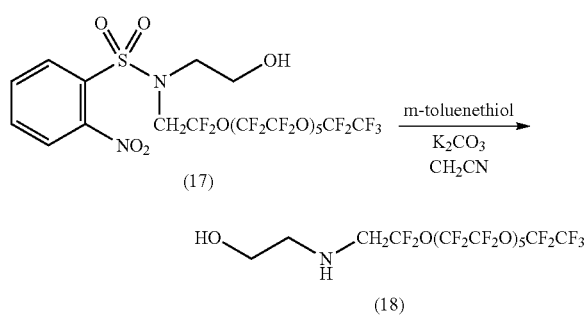

1.52 g (1.51 mmol) of a compound (17) was placed in a reaction vessel made of glass, and dissolved in 10 mL of acetonitrile. 626 mg (4.53 mmol) of potassium carbonate and 375 mg (3.02 mmol) of m-toluenethiol were added thereto, and the mixture was reacted at room temperature for 2 hours. The mixture was subjected to liquid separation with ethyl acetate-water-FC-72, and the FC-72 layer was dried over sodium sulfate. After filtration, the solvent was evaporated under reduced pressure, and the residue was purified by silica gel column chromatography to obtain 1.12 g (1.34 mmol, yield 88.6%) of a compound (18).

Data for Identification of Compound (18)

$^1$H-NMR [CDCl$_3$]: δ [ppm]=1.49 (1H, s), 2.12 (1H, s), 2.90 (2H, t, J=5.0 Hz), 3.23 (2H, t, 10.5 Hz), 3.64 (2H, m).

$^{19}$F-NMR [CDCl$_3$]: δ [ppm] −88.8 (22F, m), −86.9 (3F, s), −75.7 (2F, m).

(7-3) Synthesis of Compound (20):

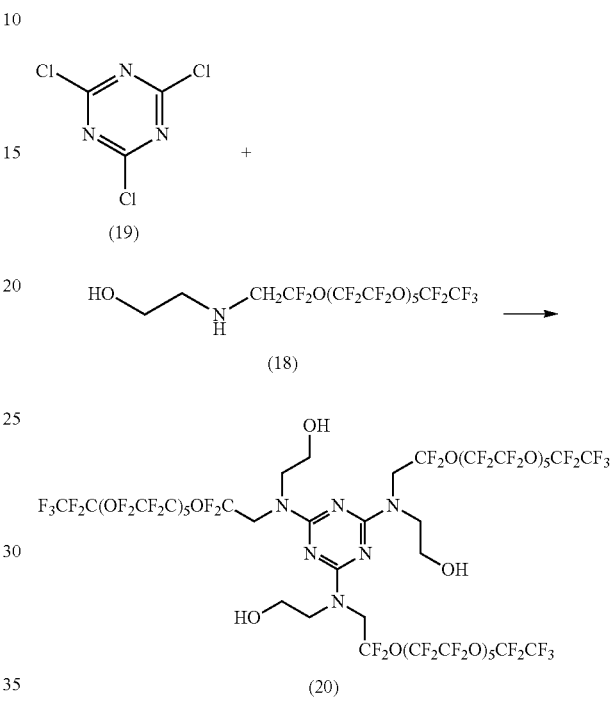

1.12 g (1.34 mmol) of the compound (18) was placed in a reaction vessel made of glass, and dissolved in 3 mL of tetrahydrofuran (THF). After being left to cool, 41.2 mg (0.223 mmol) of a compound (19) was added thereto, and the mixture was stirred for 1 hour. The mixture was reacted for 4 hours under heating and refluxing, THF was evaporated under reduced pressure. 3 mL of 1,4-dioxane was added thereto, and the mixture was reacted for 4 hours under heating and refluxing. Then, 1,4-dioxane was evaporated under reduced pressure. 2 mL of Halocarbon 1.8 Oil (trade name, manufactured by Halocarbon Products Corporation) was added thereto, and the mixture was reacted at 120° C. for 5 hours. After being left to cool, the mixture was subjected to liquid separation with FC-72-water, and the FC-72 layer was dried over sodium sulfate. After filtration, the solvent was evaporated under reduced pressure, and the residue was purified by silica gel column chromatography to obtain 170 mg (0.0656 mmol, yield 29.4%) of a compound (20).

Data for Identification of Compound (20)

$^1$H-NMR [CDCl$_3$]: δ [ppm]=3.72-3.90 (12H), 4.30 (6H).

$^{19}$F-NMR [CDCl$_3$]: δ [ppm] −73.2 to −74.9 (6F), −87.2 to −91.1 (75F).

MALDI/TOF-MS: m/z=2592.3 [M$^+$].

Example 8

Synthesis of Compound (22)

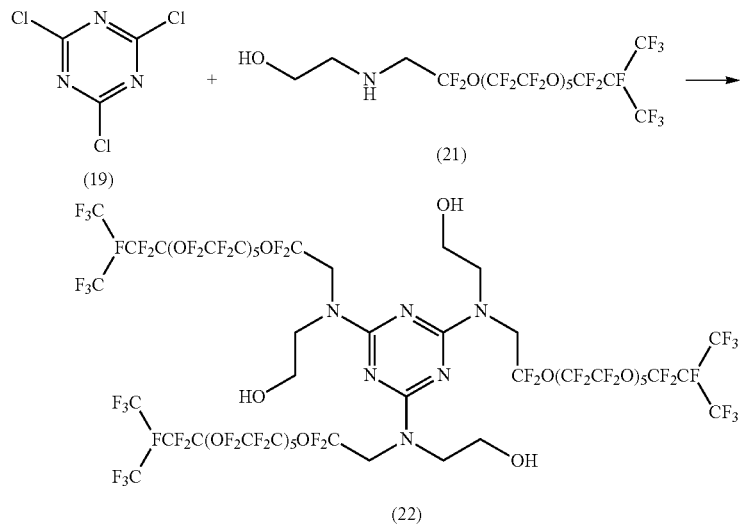

In the same manner as in Example 7-3 except that 1.26 g (1.34 mmol) of the compound (21) synthesized in the same manner as in Examples 7-1 and 7-2 was used instead of 1.12 g (1.34 mmol) of the compound (18), 194 mg (0.0671 mmol, yield 30.1%) of a compound (22) was obtained.

Data for Identification of Compound (22)

$^1$H-NMR [CDCl$_3$]: δ [ppm]=3.71-3.90 (12H), 4.31 (6H).
$^{19}$F-NMR [CDCl$_3$]: δ [ppm] −189.1 to −188.7 (3F), −73.8 to −73.4 (18F), −73.1 to −74.8 (6F), −87.2 to −91.4 (66F).
MALDI/TOF-MS: m/z=2893.4 [M$^+$].

Example 9

Synthesis of Compound (24)

In the same manner as in Example 7-3 except that 1.33 g (1.34 mmol) of the compound (23) synthesized in the same manner as in Examples 7-1 and 7-2 was used instead of 1.12 g (1.34 mmol) of the compound (18), 172 mg (0.0564 mmol, yield 25.3%) of a compound (24) was obtained.

Data for Identification of Compound (24)

$^1$H-NMR [CDCl$_3$]: δ [ppm]=3.72-3.92 (12H), 4.28 (6H).

$^{19}$F-NMR [CDCl$_3$]: δ [ppm] −186.3 to −182.9 (3F), −125.0 to −121.7 (6F), −90.5 to −87.3 (90F).

MALDI/TOF-MS: m/z=3042.9 [M$^+$].

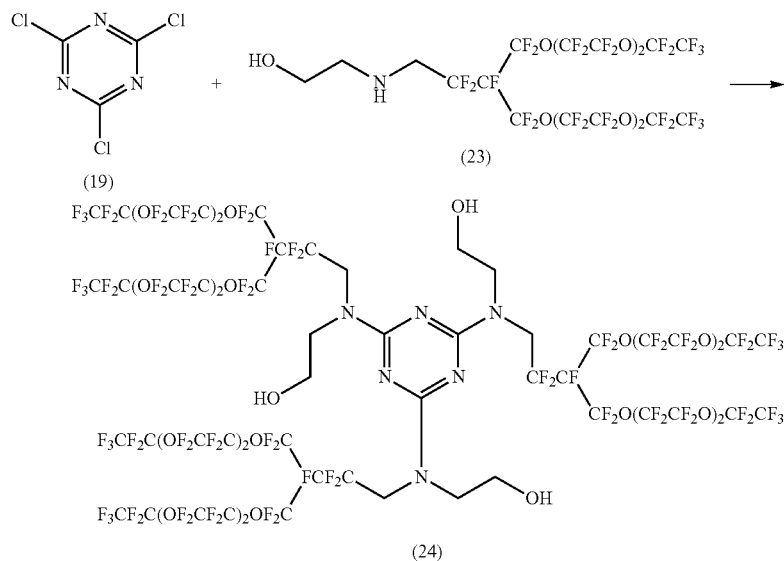

Example 10

Synthesis of Compound (26)

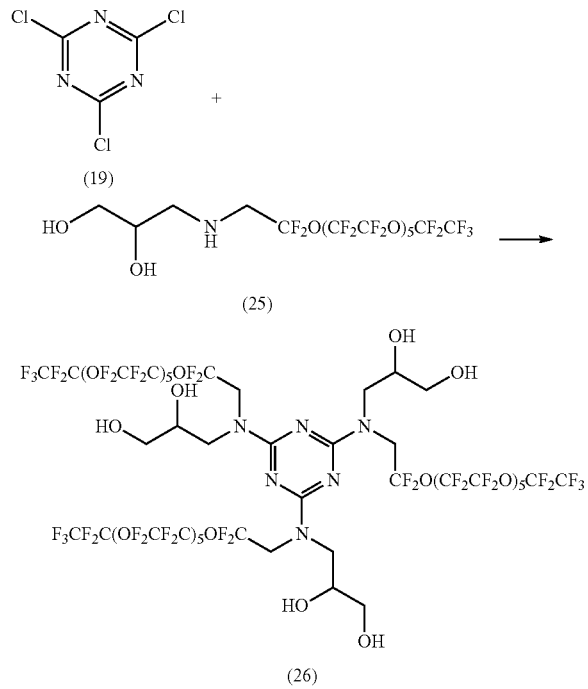

In the same manner as in Example 7-3 except that 1.16 g (1.34 mmol) of the compound (25) synthesized in the same manner as in Examples 7-1 and 7-2 was used instead of 1.12 g (1.34 mmol) of the compound (18), 123 mg (0.0459 mmol, yield 20.6%) of a compound (26) was obtained.

Data for Identification of Compound (26)

$^1$H-NMR [CDCl$_3$]: δ [ppm]=3.62-3.93 (15H), 4.30 (6H).

$^{19}$F-NMR [CDCl$_3$]: δ [ppm] −72.9 to −74.9 (6F), −87.2 to −91.0 (75F).

MALDI/TOF-MS: m/z=2683.2 [M$^+$].

Example 11

Synthesis of Compound (28)

In the same manner as in Example 7-3 except that 1.16 g (1.34 mmol) of the compound (27) synthesized in the same manner as in Examples 7-1 and 7-2 was used instead of 1.12 g (1.34 mmol) of the compound (18), 113 mg (0.0421 mmol, yield 18.9%) of a compound (28) was obtained.

Data for Identification of Compound (28)

$^1$H-NMR [CDCl$_3$]: δ [ppm]=3.61-3.88 (15H), 4.28 (6H).

$^{19}$F-NMR [CDCl$_3$]: δ [ppm] −72.9 to −74.8 (6F), −87.0 to −91.1 (75F).

MALDI/TOF-MS: m/z=2683.0 [M$^+$].

Example 12

Synthesis of Compound (31)

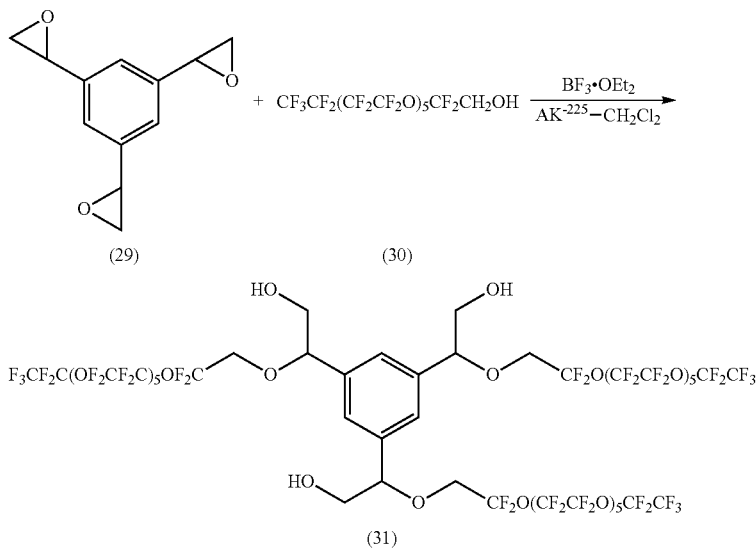

29.2 g (36.7 mmol) of a compound (30) and 20 mL of AK-225 (manufactured by Asahi Glass Co., Ltd.) were placed in a reaction vessel made of glass, and 31.3 mg (0.221 mmol) of a boron trifluoride-ethyl ether complex was added thereto under a nitrogen atmosphere. A mixture of 500 mg (2.45 mmol) of a compound (29) and 20 mL of dichloromethane was added thereto at an internal temperature of 30° C. over 2 hours, and the mixture was reacted for 5 hours. The reaction liquid was poured into ice water, followed by extraction with FC-72, and the FC-72 layer was dried over sodium sulfate. After filtration, the solvent was evaporated under reduced pressure, and the residue was purified by silica gel column chromatography to obtain 191 mg (0.0735 mmol, yield 3.0%) of a compound (31).

Data for Identification of Compound (31)

$^1$H-NMR [CDCl$_3$]: δ [ppm]=2.15 (3H, dd, J=9.9, 3.9 Hz) 3.59-3.86 (12H, m), 4.58 (3H, dd, J=8.4, 3.6 Hz), 7.13 (3H, s).

$^{19}$F-NMR [CDCl$_3$]: δ [ppm] −88.9 to −88.6 (66F, m), −86.9 (9F, s), −77.7 to −77.6 (6F, m).

MALDI/TOF-MS: m/z=2615.7 [M$^+$+Na].

Example 13

Synthesis of Compound (33)

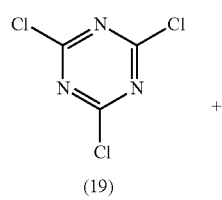

(19)

+

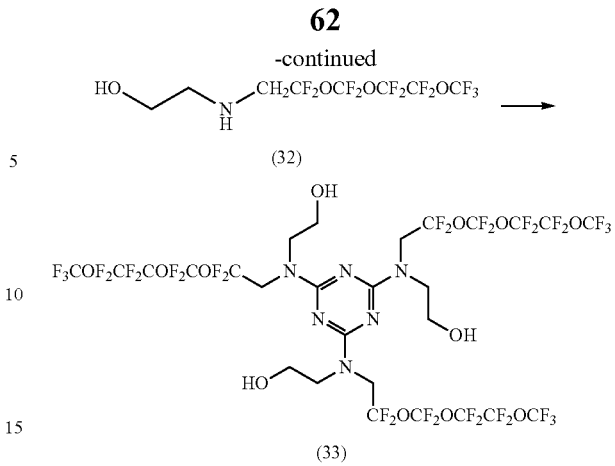

In the same manner as in Example 7-3 except that 524 mg (1.34 mmol) of the compound (32) synthesized in the same manner as in Examples 7-1 and 7-2 was used instead of 1.12 g (1.34 mmol) of the compound (18), 101 mg (0.0783 mmol, yield 35.1%) of a compound (33) was obtained.

Data for Identification of Compound (33)

$^1$H-NMR [CDCl$_3$]: δ [ppm]=3.70-3.87 (12H), 4.30 (6H).

$^{19}$F-NMR [CDCl$_3$]: δ [ppm] −51.7 (6F), −57.8 (9F), −77.8 (6F), −89.0 (6F), −90.3 (6F).

MALDI/TOF-MS: m/z=1291.0 [M$^+$].

Example 14

Synthesis of Compound (35)

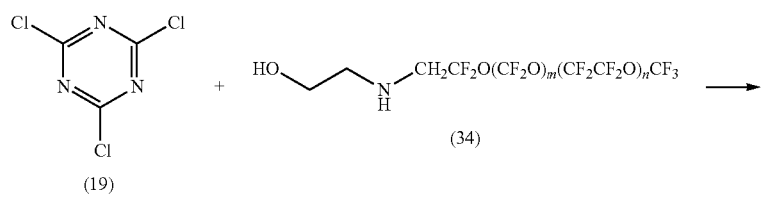

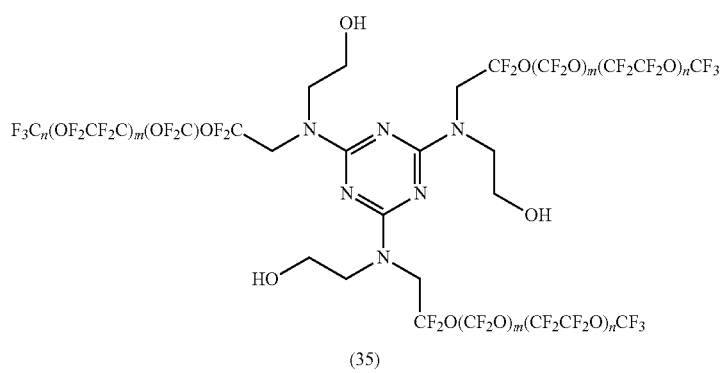

In the same manner as in Example 7-3 except that 1.50 g (molecular weight about 1000, from $^{19}$F-NMR, m:n≅2:3) of the compound (34) synthesized in the same manner as in Examples 7-1 and 7-2 was used instead of 1.12 g (1.34 mmol) of the compound (18), 202 mg of a compound (35) was obtained.

Data for Identification of Compound (35)

$^1$H-NMR [CDCl$_3$]: δ [ppm]=3.68-3.91 (12H), 4.30 (6H).
$^{19}$F-NMR [CDCl$_3$]: δ [ppm] −52.2 to −50.7, −59.7 to −56.1 (9F), −78.4 to −77.0 (6F), −91.1 to −88.1.

2. Preparation and Evaluation of Magnetic Recording Medium

Example 15

Preparation of Magnetic Recording Medium

A hard disk having the same configuration as shown in FIG. 1 was prepared. Specifically, the disk was produced in the following manner.

A soft magnetic film 2 was coated on a glass substrate 1 and then a non-magnetic intermediate layer 3, a magnetic recording layer 4, and carbon as a protective film layer 5 were deposited. On the surface of the protective film layer 5, a coating liquid prepared by the following method was coated by the following method, thereby forming a lubricating layer 6.

Preparation of Composition for Coating:

The compound (3) was dissolved in a fluorine-based solvent (Vertrel manufactured by Du Pont-Mitsui Fluorochemicals Co., Ltd., or HFE-7100DL manufactured by Sumitomo 3M, Ltd.) or trifluoroethanol in a concentration of 0.1% by mass, thereby preparing a coating liquid.

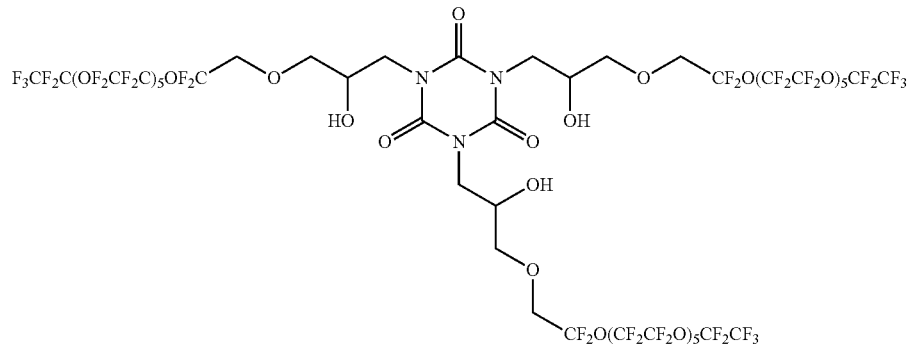

(3)

Formation of Lubricating Layer 6:

The prepared coating liquid was coated on the surface of the protective layer 5 by means of a dip coater (Mini Luber manufactured by Intevac San Jose Technology Corporation) under conditions of a dipping rate of 5 mm/sec, a dipping time of 60 sec, and a lifting rate of 1 mm/sec, followed by an ultraviolet radiation treatment for 5 minutes under a nitrogen atmosphere using an ultraviolet irradiating device (PL16-110D manufactured by Senengineering Co., Ltd.), thereby forming a lubricating layer 6, and thus obtaining a magnetic disk for test.

Example 16

In the same manner except that the compound (3) was changed to the following compound (5) in the preparation method of Example 15, a magnetic disk for test of Example 16 was obtained.

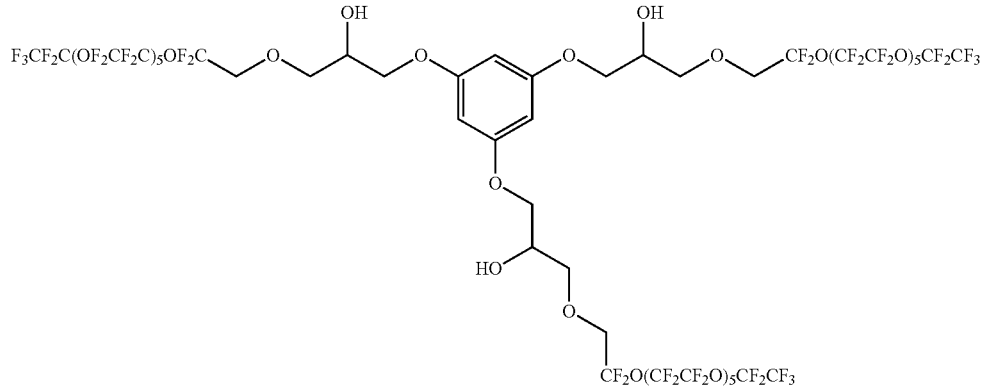

(5)

Example 17

In the same manner except that the compound (3) was changed to the following compound (8) and the compound (8) was dissolved in the concentration of 0.01% by mass in the preparation method of Example 15, a magnetic disk for test of Example 17 was obtained.

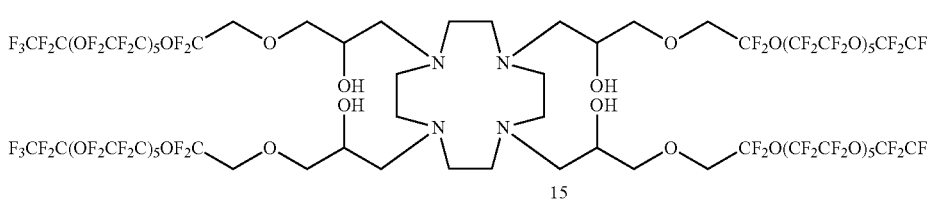
(8)

Example 18

In the same manner except that the compound (3) was changed to the following compound (10) and the compound (10) was dissolved in the concentration of 0.01% by mass in the preparation method of Example 15, a magnetic disk for test of Example 18 was obtained.

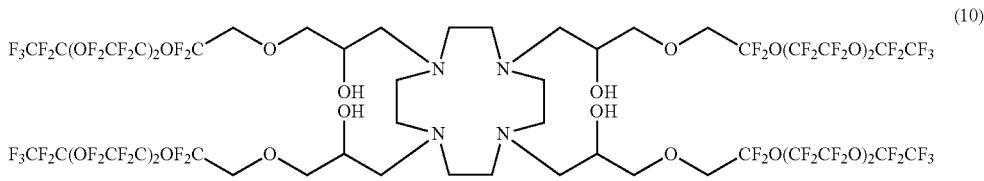
(10)

Example 19

In the same manner except that the compound (3) was changed to the following compound (12) and the compound (12) was dissolved in the concentration of 0.01% by mass in the preparation method of Example 15, a magnetic disk for test of Example 19 was obtained.

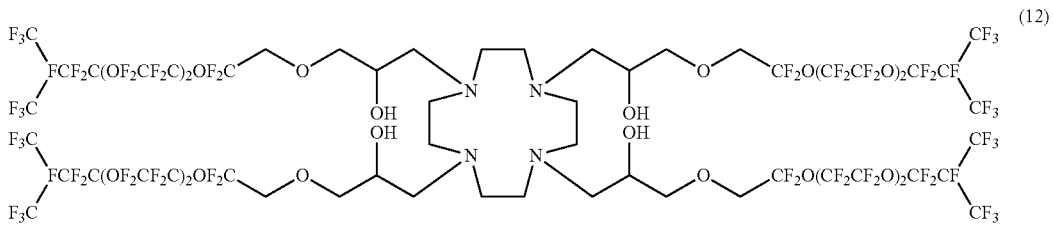
(12)

Example 20

In the same manner except that the compound (3) was changed to the following compound (14) and the compound (14) was dissolved in the concentration of 0.01% by mass in the preparation method of Example 15, a magnetic disk for test of Example 20 was obtained.

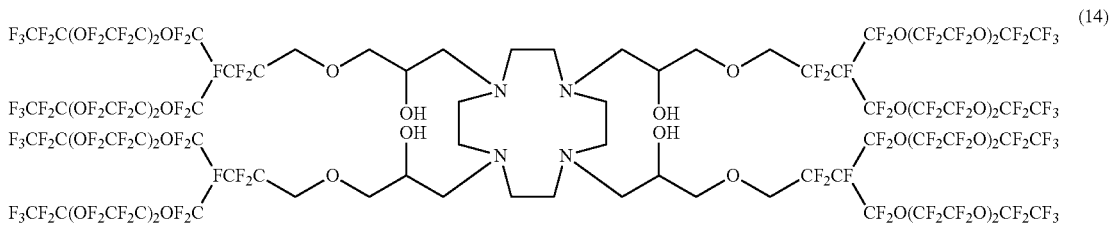
(14)

Example 21

In the same manner except that the compound (3) was changed to the following compound (20) and the compound (20) was dissolved in the concentration of 0.05% by mass in the preparation method of Example 15, a magnetic disk for test of Example 21 was obtained.

(20)

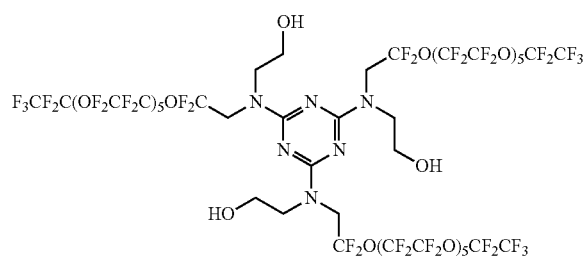

Example 22

In the same manner except that the compound (3) was changed to the following compound (22) and the compound (22) was dissolved in the concentration of 0.05% by mass in the preparation method of Example 15, a magnetic disk for test of Example 22 was obtained.

Example 24

In the same manner except that the compound (3) was changed to the following compound (26) and the compound (26) was dissolved in the concentration of 0.05% by mass in the preparation method of Example 15, a magnetic disk for test of Example 24 was obtained.

(26)

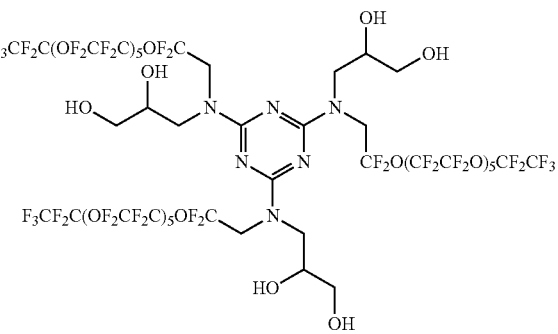

(22)

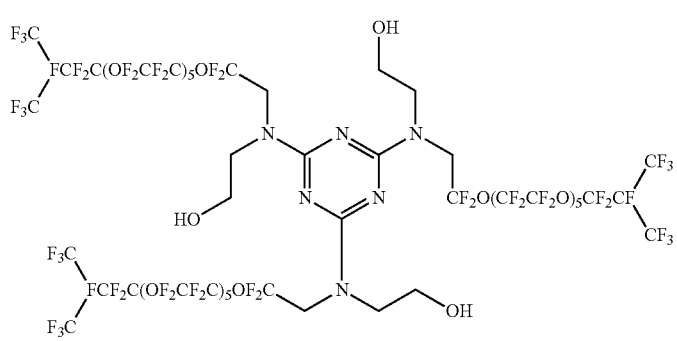

Example 23

In the same manner except that the compound (3) was changed to the following compound (24) and the compound (24) was dissolved in the concentration of 0.05% by mass in the preparation method of Example 15, a magnetic disk for test of Example 23 was obtained.

Example 25

In the same manner except that the compound (3) was changed to the following compound (28) and the compound (28) was dissolved in the concentration of 0.05% by mass in the preparation method of Example 15, a magnetic disk for test of Example 25 was obtained.

(24)

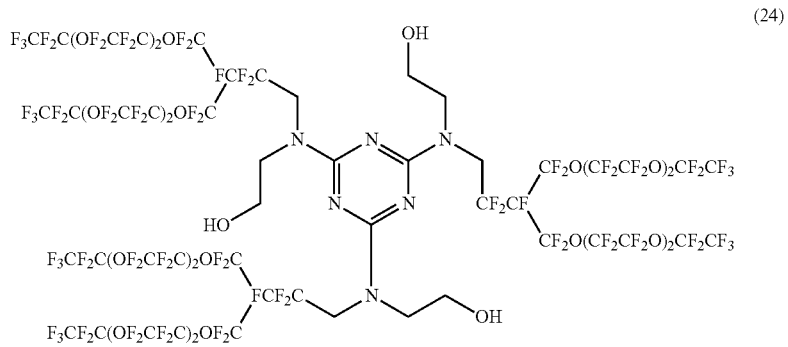

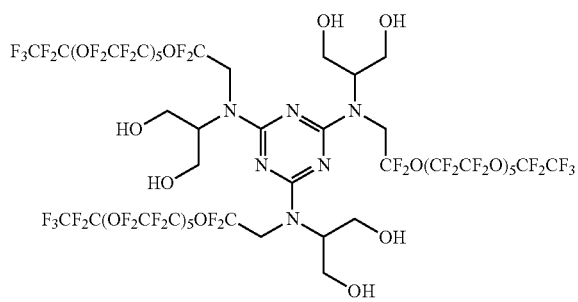

Example 26

In the same manner except that the compound (3) was changed to the following compound (31) and the compound (31) was dissolved in the concentration of 0.05% by mass in the preparation method of Example 15, a magnetic disk for test of Example 26 was obtained.

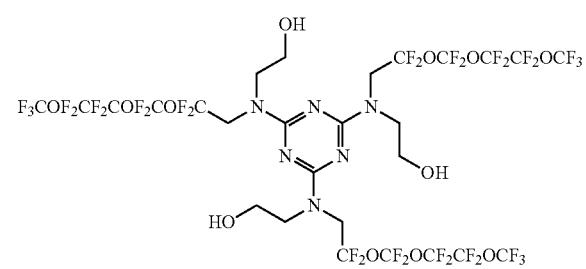

Example 28

In the same manner except that the compound (3) was changed to the following compound (35) and the compound (35) was dissolved in the concentration of 0.05% by mass in the preparation method of Example 15, a magnetic disk for test of Example 28 was obtained.

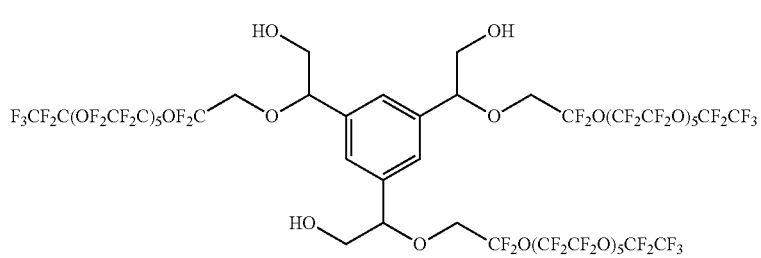

Example 27

In the same manner except that the compound (3) was changed to the following compound (33) and the compound (33) was dissolved in the concentration of 0.05% by mass in the preparation method of Example 15, a magnetic disk for test of Example 27 was obtained.

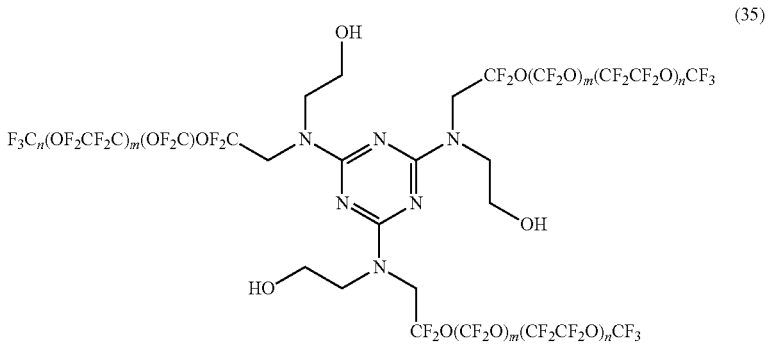

Comparative Example 1

In the same manner except that the compound (3) was changed to the following compound (36) and the compound (36) was dissolved in the concentration of 0.2% by mass in the preparation method of Example 15, a magnetic disk for test of Comparative Example 1 was obtained.

(36)

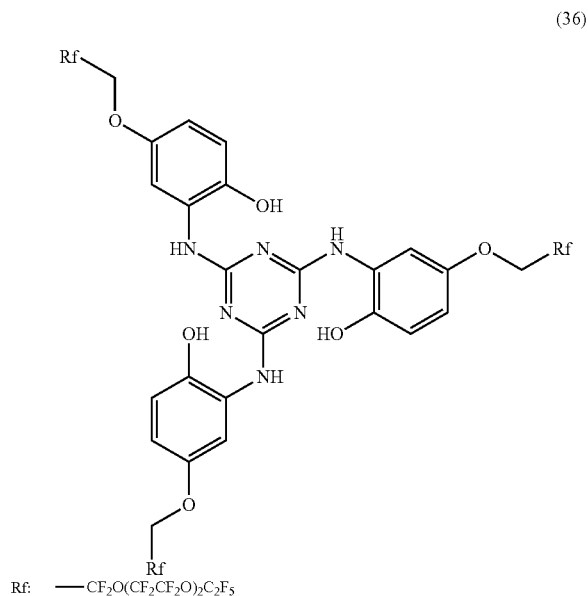

Rf: —CF$_2$O(CF$_2$CF$_2$O)$_2$C$_2$F$_5$

Comparative Example 2

In the same manner except that the compound (3) was changed to the following compound (37) and the compound (37) was dissolved in the concentration of 0.2% by mass in the preparation method of Example 15, a magnetic disk for test of Comparative Example 2 was obtained.

(37)

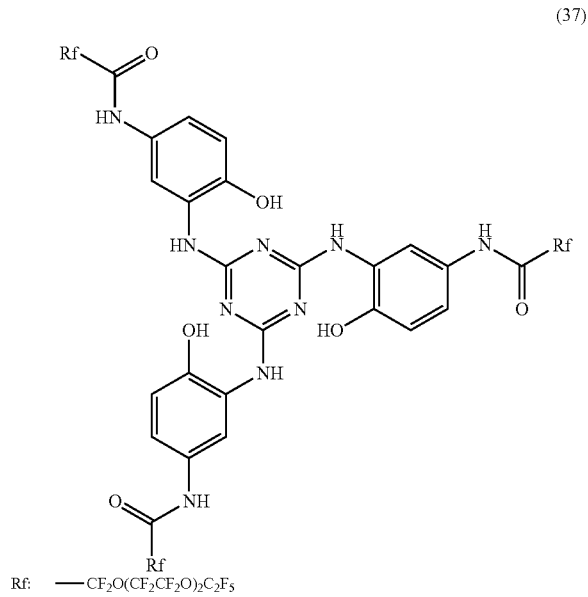

Rf: —CF$_2$O(CF$_2$CF$_2$O)$_2$C$_2$F$_5$

Comparative Example 3

In the same manner except that the compound (3) was changed to the following compound (38) and the compound (38) was dissolved in the concentration of 0.2% by mass in the preparation method of Example 15, a magnetic disk for test of Comparative Example 3 was obtained.

(38)

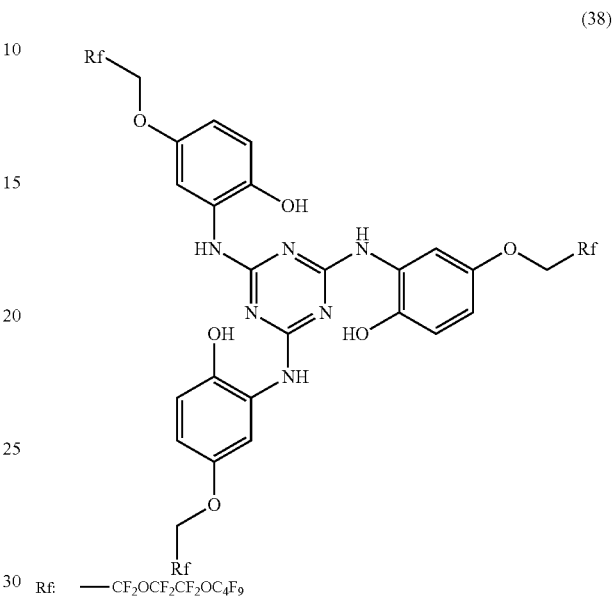

Rf: —CF$_2$OCF$_2$CF$_2$OC$_4$F$_9$

Comparative Example 4

In the same manner except that the compound (3) was changed to the following compound (39) and the compound (39) was dissolved in the concentration of 0.2% by mass in the preparation method of Example 15, a magnetic disk for test of Comparative Example 4 was obtained.

(39)

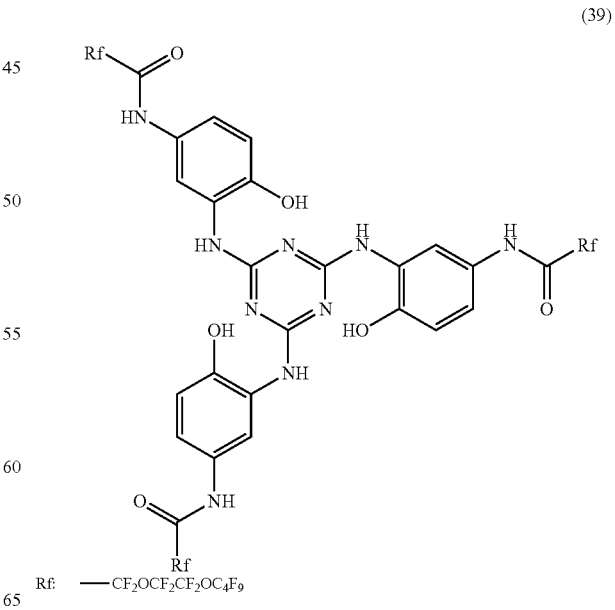

Rf: —CF$_2$OCF$_2$CF$_2$OC$_4$F$_9$

Comparative Example 5

In the same manner except that the compound (3) was changed to the following compound (40) and the compound (40) was dissolved in the concentration of 0.2% by mass in the preparation method of Example 15, a magnetic disk for test of Comparative Example 5 was obtained.

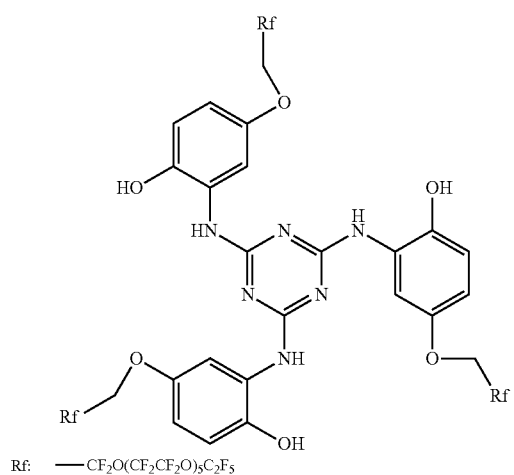

(40)

Rf: —CF$_2$O(CF$_2$CF$_2$O)$_5$C$_2$F$_5$

Evaluation:

Evaluation of Average Film Thickness

It is preferable that the average film thickness be as thin as possible, from the viewpoint of the reduction in spacing between the head and the disk. However, if the film thickness is 1 angstrom or less, it is determined that the lubricating layer is insufficiently coated. The average film thickness of the lubricating film was measured with respect to the lubricant-coated surface of the respective magnetic disk for test by means of an SRA manufactured by HDI Instrumentation, Inc., and a sensory evaluation was made at 4 levels by the following criteria.

AA: Ultra-thin film (1 to 10 angstroms)
A: Thin film (more than 10 angstroms, less than 20 angstroms)
B: Thick film (20 angstroms or more)
C: No film1 (less than 1 angstrom)

Evaluation of Coated Surface Shape

It is preferable that the surface of the magnetic disk be as smooth as possible so as to reduce the false recognition, head collision, or the like. Regarding the lubricant-coated surface of the respective magnetic disk for test, the surface roughness was observed by means of visual confirmation, a laser surface inspection device (SRA-10,000 manufactured by HDI Instrumentation, Inc.), and AFM (Dimension 3100 AFM manufactured by Veeco Instruments Inc.), and a sensory evaluation was made at 3 levels by the following criteria.

AA: No surface unevenness was observed by laser inspection and AFM.
A: No unevenness was observed by visual confirmation. Slight irregularities were observed by laser inspection and AFM.
B: Unevenness was observed by visual confirmation.

Adsorption Performance

The respective magnetic disks for test were dipping-washed in a fluorine-based solvent (Vertrel manufactured by Du Pont-Mitsui Fluorochemicals Co., Ltd. or HFE-7100DL manufactured by Sumitomo 3M, Ltd.) or trifluoroethanol using a dip coater (Mini Luber manufactured by Intevac San Jose Technology Corporation) under conditions of a dipping rate of 5 mm/sec, a dipping time of 60 sec, and a lifting rate of 1 mm/sec before and after an ultraviolet radiation treatment. Then, the film thickness was evaluated by the same method as for the average film thickness as described above.

AA: Good adsorption (more than 2.0 angstroms)
A: Adsorption possible (1.0 to 2.0 angstroms)
B: Insufficient adsorption (0.5 angstrom or more, less than 1.0 angstrom)
C: Adsorption not possible (less than 0.5 angstroms)

Evaluation of Head Floating Stability

First, the respective magnetic disks for test were rotated by a spin stand, and a reading head was floated. Subsequently, the head was fixed at a disk radius of 20 mm, and floated under a normal temperature and a normal pressure for 1 week. Subsequently, the head after the test was observed, and a sensory evaluation was made on the lubricant transferred to the head using an optical microscope at 4 levels by the following criteria. The used evaluation device was an HDF tester manufactured by Kubota Comps Corporation and the head was a femto slider.

AA: No transfer of the lubricant to the head was observed and the head was in the clear state.
A: Slight transfer of the lubricant to the head was observed, but there was contamination having a size of 10 μm or less at three or less places on the head.
B: Transfer of the lubricant to the head was observed, and there was contamination having a size of 10 μm or more or contamination having a size of 10 μm or less at four or more places on the head. However, the head was floatable.
C: Transfer of the lubricant to the front side of the head was observed, the head and the disk were normally brought into contact with each other, and the head was not floatable.

The measurement results and evaluation results above are summarized in the following Table.

TABLE 1

| | Material | Concentration (wt %) | Average film thickness | Shape of surface | Adsorption performance UV not irradiated | Adsorption performance UV irradiated | Head floating stability |
|---|---|---|---|---|---|---|---|
| Ex. 15 | Compound (3) | 0.1 | AA | A | A | AA | A |
| Ex. 16 | Compound (5) | 0.1 | AA | AA | B | AA | AA |
| Ex. 17 | Compound (8) | 0.01 | AA | AA | A | AA | A |
| Ex. 18 | Compound (10) | 0.01 | AA | A | A | AA | A |
| Ex. 19 | Compound (12) | 0.01 | AA | A | A | AA | A |
| Ex. 20 | Compound (14) | 0.01 | AA | A | A | AA | A |
| Ex. 21 | Compound (20) | 0.05 | AA | AA | A | AA | AA |

TABLE 1-continued

| | Material | Concentration (wt %) | Average film thickness | Shape of surface | Adsorption performance UV not irradiated | Adsorption performance UV irradiated | Head floating stability |
|---|---|---|---|---|---|---|---|
| Ex. 22 | Compound (22) | 0.05 | AA | AA | A | AA | AA |
| Ex. 23 | Compound (24) | 0.05 | AA | AA | A | AA | AA |
| Ex. 24 | Compound (26) | 0.05 | AA | AA | A | AA | AA |
| Ex. 25 | Compound (28) | 0.05 | AA | AA | A | AA | AA |
| Ex. 26 | Compound (31) | 0.05 | AA | AA | A | AA | AA |
| Ex. 27 | Compound (33) | 0.05 | AA | AA | A | AA | AA |
| Ex. 28 | Compound (35) | 0.05 | AA | AA | A | AA | AA |
| Comp. Ex. 1 | Compound (36) | 0.2 | A | B | B | A | B |
| Comp. Ex. 2 | Compound (37) | 0.2 | B | B | B | B | C |
| Comp. Ex. 3 | Compound (38) | 0.2 | AA | A | B | A | B |
| Comp. Ex. 4 | Compound (39) | 0.2 | B | B | B | B | C |
| Comp. Ex. 5 | Compound (40) | 0.2 | A | A | A | A | B |

An RAS device was installed in a sample chamber of a complete vacuum FT-IR spectrometer "FT-IR6400" manufactured by JASCO Corporation, whereby an IR spectrum was measured with respect to the respective magnetic disks.

As a result, it was confirmed that all of the magnetic disks for test of Examples 1 to 4 showed a sharp peak attributed to a stretching vibration of $CF_3$ in a range of 1255 cm$^{-1}$ to 1270 cm$^{-1}$. This result suggests that in the exemplary compound, the PFPE chain is oriented vertically with respect to the layer surface on the protective layer surface.

4. Production and Evaluation of Head Slider

Example 29

Production of Head Slider

The compound (5) was dissolved in a fluorine-based solvent (Vertrel manufactured by Du Pont-Mitsui Fluorochemicals Co., Ltd., or HFE-7100DL manufactured by Sumitomo 3M, Ltd.) or trifluoroethanol in a concentration of 0.1% by mass, thereby preparing a coating liquid.

The coating liquid was coated on the femto slider by a dip coating method. Specifically, the femto slider was dipped in the coating liquid for 1 minute and coated at a lifting rate of 1 mm/sec, followed by an ultraviolet radiation treatment for 5 minutes under a nitrogen atmosphere using an ultraviolet irradiating device (PL16-110D manufactured by Senengineering Co., Ltd.), thereby forming a lubricating layer 6, and thus obtaining a magnetic disk for test. Thereafter, the magnetic disk for test was washed by being dipped in a fluorine-based solvent "Vertrel" (manufactured by Du Pont-Mitsui Fluorochemicals Co., Ltd.) for 1 minute. Thus, a head slider for test having a lubricating film was produced.

Example 30

In the same manner except that the compound (5) was changed to the following compound (20) and the compound (20) was dissolved in the concentration of 0.05% by mass in the preparation method of Example 29, a head slider for test of Example 30 was produced.

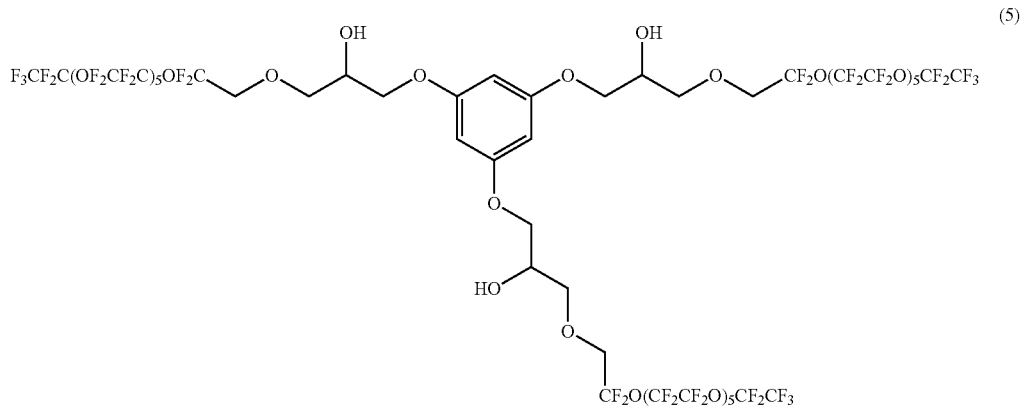

(20)

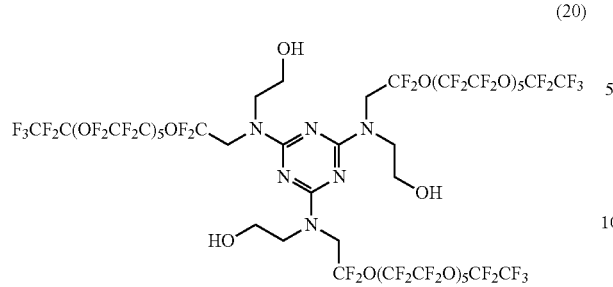

Comparative Example 6

In the same manner except that the compound (5) was changed to the following compound (36) and the compound (36) was dissolved in the concentration of 0.2% by mass in the preparation method of Example 29, a head slider for test of Comparative Example 6 was produced.

(36)

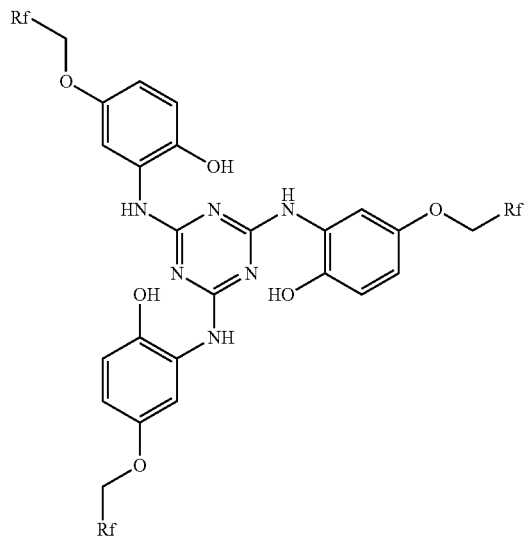

Rf: —CF$_2$O(CF$_2$CF$_2$O)$_2$C$_2$F$_5$

Comparative Example 7

In the same manner except that the compound (5) was changed to the following compound (40) and the compound (40) was dissolved in the concentration of 0.2% by mass in the preparation method of Example 29, a head slider for test of Comparative Example 7 was produced.

(40)

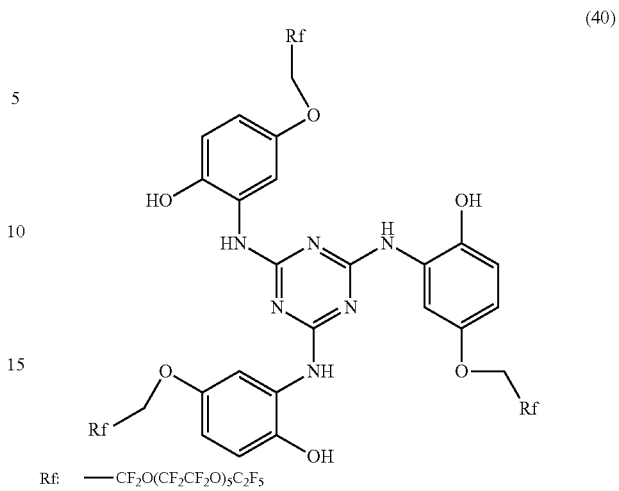

Rf: —CF$_2$O(CF$_2$CF$_2$O)$_5$C$_2$F$_5$

Evaluation:

2.5-inch magnetic media in which a lubricating film was formed by coating of "Z-Tetraol" were rotated at 5400 PRM in a pressure reduction spin stand, and the respective sliders of Examples 29 and 30, and Comparative Examples 6 and 7 were loaded by ramp load and caused to seek a radial position at 22 mm. From when the head floated stably, the chamber pressure was reduced. When an AE sensor detected a moment at which flying height decreased, and the head contacted the media, the pressure was returned to atmospheric pressure, and the fly height was raised.

The pressure at the time when the AE detects the contact is called TDP (touch down pressure), and the pressure at the time when the AE is stabilized due to the return to the atmospheric pressure is called TOP (take off pressure). The smaller these pressures, the larger the head-disk clearance. The friction force caused during the contact was measured using a friction gauge that was installed in a head pivot portion. This operation was repeated three times, and the average value thereof was calculated.

The head after the contact was observed by a microscope to observe the attachment of the lubricant to the head, and evaluated according to the following criteria.

Evaluation Criteria for Head Contamination

AA: No transfer of the lubricant to the head was observed and the head was in the clear state.

A: Slight transfer of the lubricant to the head was partially observed, but there was contamination having a size of 10 μm or less at three or less places on the head.

B: Transfer of the lubricant to the head was observed, and there was contamination having a size of 10 μm or more or contamination having a size of 10 m or less at four or more places on the head. However, the head was refloatable.

C: Transfer of the lubricant to the front side of the head was observed, and the head was not refloatable.

The results are shown in the following Table.

TABLE 2

| | Material of lubricating film | Friction force (gf) | TDP (Torr) | Head contamination |
|---|---|---|---|---|
| Example 29 | Compound (5) | A (3 gf or less) | 401 | AA |
| Example 30 | Compound (20) | A (3 gf or less) | 401 | AA |
| Comparative Example 6 | Compound (36) | A (3 gf or less) | 400 | B |

TABLE 2-continued

| | Material of lubricating film | Friction force (gf) | TDP (Torr) | Head contamination |
|---|---|---|---|---|
| Comparative Example 7 | Compound (40) | A (3 gf or less) | 402 | A |

From the results shown in Table above, it can be confirmed that a head slider having film including the lubricant composition of the present invention has low friction and less head contamination.

The invention claimed is:

1. A lubricant composition comprising at least one kind of compound represented by following formula (1):

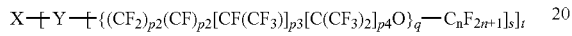

where X represents a cyclic group that may be substituted; Y represents a divalent or higher-valent linking group having at least one polar group and having no aromatic cyclic group; p1 represents an integer of 1 to 4; p2, p3, and p4 each represents an integer of 0 to 4; q represents an integer of 1 to 30; n represents an integer of 1 to 10; s represents an integer of 1 to 4; and t represents an integer of 2 to 10, provided that the binding sequence of $-(CF_2)_{p1}-$, $-(CF)_{p2}-$, $-[CF(CF_3)]_{p3}-$, and $-[C(CF_3)_2]_{p4}-$ that constitute $-\{(CF_2)_{p1}(CF)_{p2}[CF(CF_3)]_{p3}[C(CF_3)_2]_{p4}O\}-$ in formula (1) is not limited, and $-\{(CF_2)_{p1}(CF)_{p2}[CF(CF_3)]_{p3}[C(CF_3)_2]_{p4}O\}-$ means a perfluoroalkyleneoxy group in which a perfluoroalkylene unit selected from $-(CF_2)_{p1}-$, $-(CF)_{p2}-$, $-[CF(CF_3)]_{p3}-$, and $-[C(CF_3)_2]_{p4}-$ and an oxygen atom are distributed randomly; when q is 2 or more, a plurality of $-\{(CF_2)_{p1}(CF)_{p2}[CF(CF_3)]_{p3}[C(CF_3)_2]_{p4}O\}-$ may be the same as or different from each other; when s is 2 or more, a plurality of n's and q's may be the same as or different from each other; and when t is 2 or more, a plurality of s's and Y's may be the same as or different from each other; and when p2 is 1 or more, the perfluoroalkyleneoxy group has a branched structure.

2. The lubricant composition according to claim 1, wherein the fluorine content per molecule of the compound is 37% by mass or more and 76% by mass or less.

3. The lubricant composition according to claim 1, wherein X is an aromatic cyclic group or non-aromatic cyclic group, which may be substituted.

4. The lubricant composition according to claim 1, wherein the polar group contained in Y is a polar group selected from the group consisting of a hydroxyl group, an amino group, a mercapto group, a carboxyl group, a carbamoyl group, a sulfonamide group, a phosphoric acid group, and a phosphate group.

5. The lubricant composition according to claim 1, wherein the polar group contained in Y is a hydroxyl group.

6. The lubricant composition according to claim 1, wherein Y is a linking group, which contains a $C_2$ to $C_{10}$ alkylene group, provided that one carbon atom or two or more carbon atoms that are not adjacent to each other in the alkylene group may be substituted with an oxygen atom, a nitrogen atom, a sulfur atom, or a carbonyl group (C=O), and further, a polar group is bonded to any carbon atom in the alkylene group or to a nitrogen atom in the case where the carbon atom is substituted with a nitrogen atom directly or via a $C_1$ to $C_5$ alkylene group.

7. The lubricant composition according to claim 1, wherein Y contains a partial structure represented by the following formula:

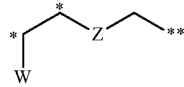

where W represents a polar group, Z represents an oxygen atom, a sulfur atom, or a nitrogen atom; any one of carbon atoms marked with * or Z in the case where Z is a nitrogen atom is bonded to X directly or via a $C_1$ to $C_8$ alkylene group, provided that one carbon atom or two or more carbon atoms that are not adjacent to each other in the alkylene group may be substituted with an oxygen atom, a nitrogen atom, a sulfur atom, or a carbonyl group (C=O); and a carbon atom marked with ** is bonded to $-\{(CF_2)_{p1}(CF)_{p2}[CF(CF_3)]_{p3}[C(CF_3)_2]_{p4}O\}_q-C_nF_{2n+1}$.

8. The lubricant composition according to claim 1, wherein Y is a group represented by any of the following formulae (Y1) to (Y3):

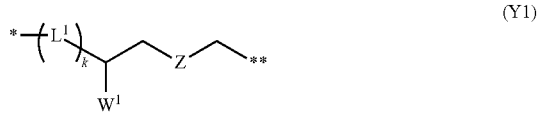

where $W^1$ and $W^2$ each represents a polar group, or a group having a polar group including one or more polar groups, one or more methylene groups ($CH_2$), one or more methine groups (CH), one or more quaternary carbon atoms, or a group formed by combination of two or more thereof; k represents 0 or 1; $L^1$ to $L^3$ each represents $-CH_2-$, $-OCH_2-$, $-CH_2O-$, or $-C(=O)-$; Z represents an oxygen atom or NH; and * and ** each represents binding positions with X and $-\{(CF_2)_{p1}(CF)_{p2}[CF(CF_3)]_{p3}[C(CF_3)_2]_{p4}O\}_q-C_nF_{2n+1}$, respectively.

9. The lubricant composition according to claim 1, wherein the perfluoroalkyleneoxy group in the formula (1) is a group represented by the following formula (2a) or (2b):

-continued

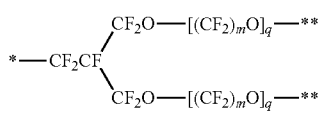
(2b)

where, in formulae (2a) and (2b), m represents an integer of 2 to 4, q represents an integer of 1 to 30, a plurality of m's in the case where q in the formula (2a) is 2 or more, and a plurality of m's in the formula (2b) may be the same as or different from each other, * represents a binding position with Y, and ** represents a binding position with $C_nF_{2n+1}$.

10. The lubricant composition according to claim 1, wherein the perfluoroalkyleneoxy group in the formula (1) is a group represented by the following formula (3a) or (3b):

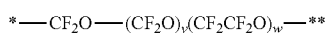
(3a)

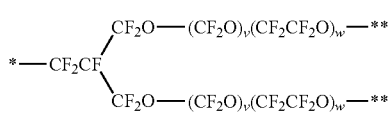
(3b)

in the formulae (3a) and (3b), v represents an integer of 1 to 20 and w represents an integer of 1 to 20, provided that (v+w) is an integer of 1 to 30; the binding sequence of ($CF_2O$) and ($CF_2CF_2O$) is not limited, * represents a binding position with Y, and ** represents a binding position with $C_nF_{2n}$—$p_1$.

11. The lubricant composition according to claim 1, wherein at least one kind of compound represented by the formula (1) is a compound represented by any of the following formulae (1a) to (1f):

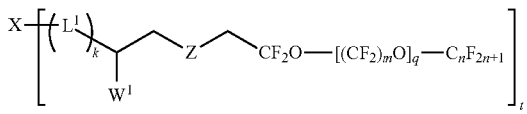
(1a)

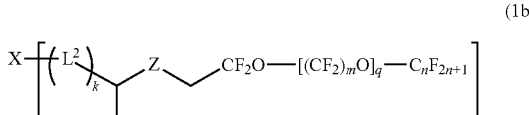
(1b)

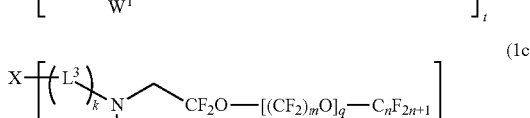
(1c)

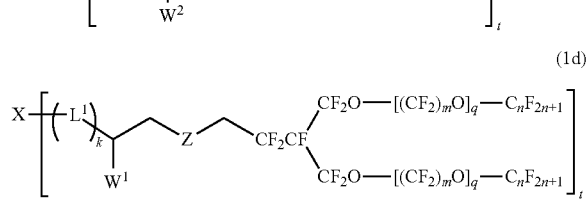
(1d)

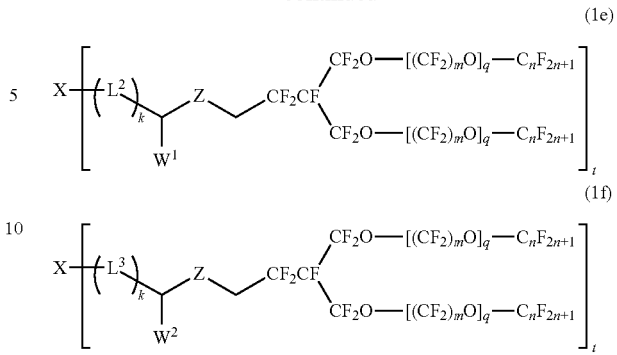
(1e)

(1f)

where in the formulae, X represents a cyclic group which may be substituted; $W^1$ and $W^2$ each represents a polar group, or a group having a polar group including one or more polar groups, one or more methylene groups ($CH_2$), one or more methine groups (CH), one or more quaternary carbon atoms, or a group formed by combination of two or more thereof; k represents 0 or 1; $L^1$ to $L^3$ each represents —$CH_2$—, —$OCH_2$—, —$CH_2O$—, or —C(=O)—; Z represents an oxygen atom or NH; m represents an integer of 2 to 4; n represents an integer of 1 to 10; t represents an integer of 2 to 10; and q represents an integer of 1 to 30, provided that a plurality of $L^1$ to $L^3$, k, $W^1$, $W^2$, Z, m, n, and q each present in the formula may be the same as or different from each other.

12. The lubricant composition according to claim 1, wherein at least one kind of compound represented by the formula (1) is a compound represented by any of the following formulae (1g) to (11):

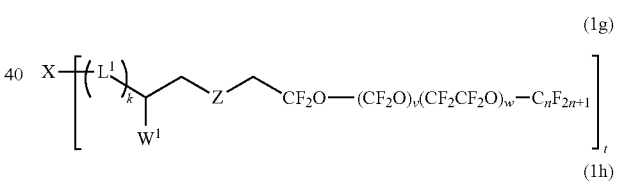
(1g)

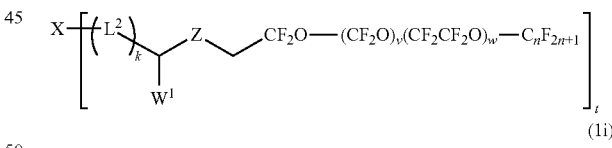
(1h)

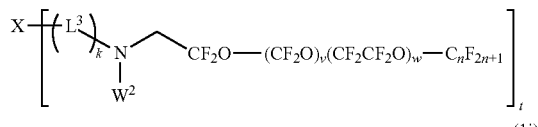
(1i)

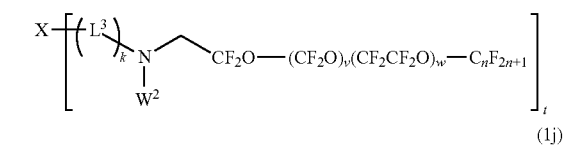
(1j)

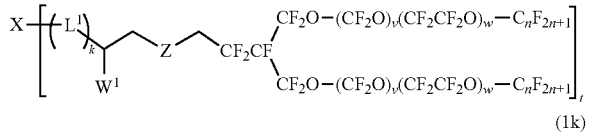
(1k)

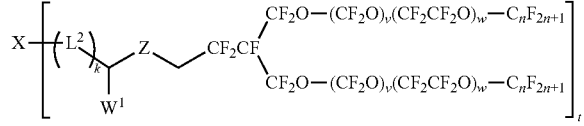

-continued

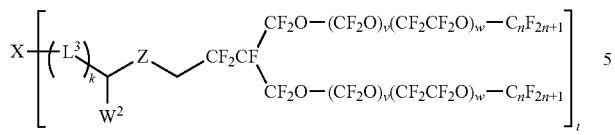
(II)

where, in the formulae, X represents a cyclic group which may be substituted; $W^1$ and $W^2$ each represents a polar group, or a group having a polar group including one or more polar groups, one or more methylene groups ($CH_2$), one or more methine groups (CH), one or more quaternary carbon atoms, or a group formed by combination of two or more thereof; k represents 0 or 1; $L^1$ to $L^3$ each represents —$CH_2$—, —$OCH_2$—, —$CH_2O$—, or —C(=O)—; Z represents an oxygen atom or NH; v represents an integer of 1 to 20; and w represents an integer of 1 to 20, provided that (v+w) is an integer of 1 to 30; the binding sequence of ($CF_2O$) and ($CF_2CF_2O$) is not limited; n represents an integer of 1 to 10; and t represents an integer of 2 to 10, provided that a plurality of $L^1$ to $L^3$, k, $W^1$, $W^2$, Z, v, w, and n each present in the formula may be the same as or different from each other.

13. The lubricant composition according to claim 1, wherein the lubricant composition is used as a lubricant of a disk for a magnetic recording medium.

14. A film comprising the lubricant composition according to claim 1.

15. The film according to claim 14, wherein the film is formed by a dip coating method, a spin coating method, or a vacuum—deposition method.

16. A laminate comprising:
a substrate having carbon as a main raw material on at least a part of the surface; and
the film according to claim 14 on the substrate.

17. The laminate according to claim 16, wherein the laminate is formed by carrying out an ultraviolet ray irradiation treatment or a heat treatment for adherence onto the substrate.

18. A magnetic recording medium comprising at least:
a magnetic layer and
the film according to claim 14.

19. The magnetic recording medium according to claim 18, comprising a protective layer between the magnetic layer and the film.

20. A magnetic recording device comprising the magnetic recording medium according to claim 18.

21. A head slider provided with a magnetic head, comprising the film according to claim 14 on at least a part of the surface.

22. A magnetic recording device comprising the head slider according to claim 21.

23. A fluorine—based compound represented by following formula (1):

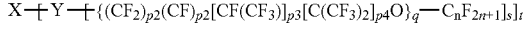
(1)

where X represents a cyclic group which may be substituted; Y represents a divalent or higher-valent linking group having at least one polar group and having no aromatic cyclic group; p1 represents an integer of 1 to 4; p2, p3, and p4 each represents an integer of 0 to 4; q represents an integer of 1 to 30; n represents an integer of 1 to 10; s represents an integer of 1 to 4; and t represents an integer of 2 to 10, provided that the binding sequence of —$(CF_2)_{p1}$—, —$(CF)_{p2}$—, —$[CF(CF_3)]_{p3}$—, and —$[C(CF_3)_2]_{p4}$— that constitute —$\{(CF_2)_{p1}(CF)_{p2}[CF(CF_3)]_{p3}[C(CF_3)_2]_{p4}O\}$— in the formula (1) is not limited, and —$\{(CF_2)_{p1}(CF)_{p2}[CF(CF_3)]_{p3}[C(CF_3)_2]_{p4}O\}$— means a perfluoroalkyleneoxy group in which a perfluoroalkylene unit selected from —$(CF_2)_{p1}$—, —$(CF)_{p2}$—, —$[CF(CF_3)]_{p3}$—, and —$[C(CF_3)_2]_{p4}$— and an oxygen atom are distributed randomly; when q is 2 or more, a plurality of —$\{(CF_2)_{p1}(CF)_{p2}[CF(CF_3)]_{p3}[C(CF_3)_2]_{p4}O\}$— may be the same as or different from each other; when s is 2 or more, a plurality of n's and q's may be the same as or different from each other; and when t is 2 or more, a plurality of s's and Y's may be the same as or different from each other; and when p2 is 1 or more, the perfluoroalkyleneoxy group has a branched structure.

24. The fluorine—based compound according to claim 23, wherein the fluorine content per molecule is 37% by mass or more and 76% by mass or less.

25. The fluorine—based compound according to claim 23, wherein X is a group selected from the group consisting of benzene, cyclohexane, triazine, isocyanurate, pyrimidine, and 1,4,7,10-tetraazacyclododecane, which may be substituted.

26. The fluorine-based compound according to claim 23, wherein X is a cyclic group of any of the following formulae (X1) to (X4):

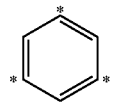
(X1)

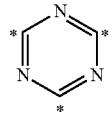
(X2)

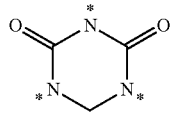
(X3)

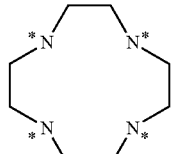
(X4)

where, in the formula, * represents a position at which Y can be bonded, and Y's are bonded to two or more * positions of the respective formulae, and other substituents may be bonded at the * position at which Y is not bonded or at the other positions at which Y can be bonded.

27. The fluorine-based compound according to claim 23, wherein Y in the formula (1) is a linear or branched divalent to pentavalent linking group having 1 to 15 carbon atoms, having at least one atom or atom group selected from a group consisting of an ether-based oxygen atom, an amine-based nitrogen atom, and an amide bond.

28. The fluorine—based compound according to claim 23, wherein Y is a linking group, which contains a $C_2$ to $C_{10}$ alkylene group, provided that one carbon atom or two or more carbon atoms that are not adjacent to each other in the alkylene group may be substituted with an oxygen atom, a nitrogen atom, a sulfur atom, or a carbonyl group (—(C=O)—), and further, a polar group is bonded to any carbon atom in the alkylene group or to a nitrogen atom in the case where the carbon atom is substituted with a nitrogen atom directly or via a $C_1$ to $C_5$ alkylene group.

29. The fluorine-based compound according to claim 23, wherein Y contains a partial structure represented by the following formula:

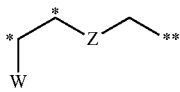

where, in the formula, W represents a polar group, Z represents an oxygen atom, a sulfur atom, or a nitrogen atom; any one of carbon atoms marked with * or Z in the case where Z is a nitrogen atom is bonded to X directly or via a $C_1$ to $C_8$ alkylene group, provided that one carbon atom or two or more carbon atoms that are not adjacent to each other in the alkylene group may be substituted with an oxygen atom, a nitrogen atom, a sulfur atom, or a carbonyl group (C=O)); and a carbon atom marked with ** is bonded to —{$(CF_2)_{p1}(CF)_{p2}[CF(CF_3)]_{p3}[C(CF_3)_2]_{p4}O\}_q$—$C_nF_{2n+1}$.

30. The fluorine-based compound according to claim 23, wherein Y is a linking group represented by any of the following formulae (Y1) to (Y3):

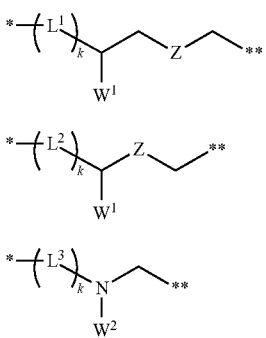

where, in the formula, $W^1$ and $W^2$ each represents a polar group, or a group having a polar group including one or more polar groups, one or more methylene groups ($CH_2$), one or more methine groups (CH), one or more quaternary carbon atoms, or a group formed by combination of two or more thereof; k represents 0 or 1; $L^1$ to $L^3$ each represents —$CH_2$—, —$OCH_2$—, —$CH_2O$—, or —C(=O)—; Z represents an oxygen atom or NH; and * and ** each represents binding positions with X and —{$(CF_2)_{p1}(CF)_{p2}[CF(CF_3)]_{p3}[C(CF_3)_2]_{p4}O\}_q$—$C_nF_{2n+1}$.

31. The fluorine—based compound according to claim 23, wherein the perfluoroalkyleneoxy group in the formula (1) is a group represented by the following formula (2a) or (2b):

where, in the formulae, m represents an integer of 2 to 4, q represents an integer of 1 to 30, a plurality of m's in the case where q in the formula (2a) is 2 or more, and a plurality of m's in the formula (2b) may be the same as or different from each other, * represents a binding position with Y, and ** represents a binding position with $C_nF_{2n+1}$.

32. The fluorine-based compound according to claim 23, wherein the perfluoroalkyleneoxy group in the formula (1) is a group represented by the following formula (3a) or (3b):

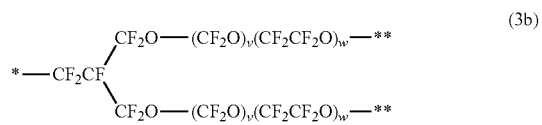

where in the formulae, v represents an integer of 1 to 20 and w represents an integer of 1 to 20, provided that (v+w) is an integer of 1 to 30; the binding sequence of ($CF_2O$) and ($CF_2CF_2O$) is not limited, * represents a binding position with Y, and ** represents a binding position with $C_nF_{2n+1}$.

33. A fluorine-based compound represented by any of following formulae (1a) to (1f):

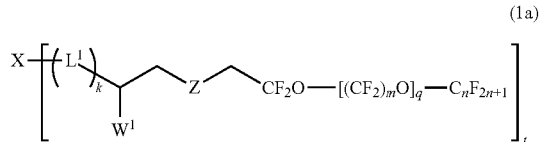

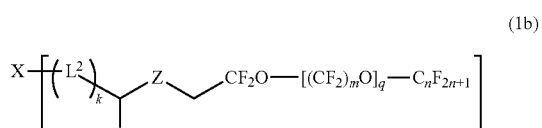

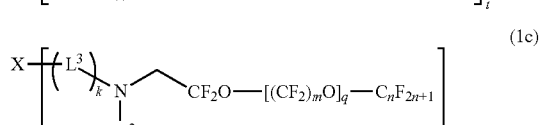

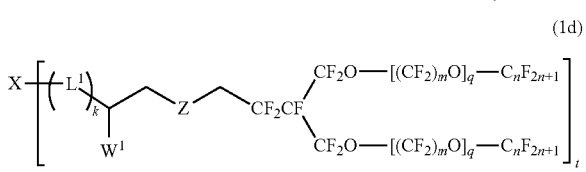

(1e)

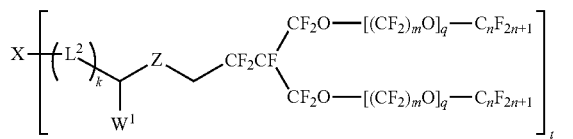

(1f)

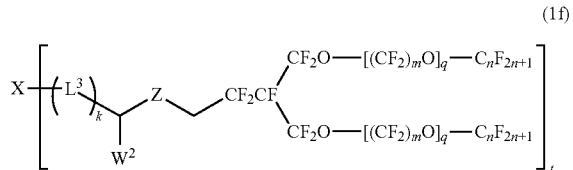

where, in the formulae, X represents a cyclic group which may be substituted; $W^1$ and $W^2$ each represents a polar group, or a group having a polar group including one or more polar groups, one or more methylene groups ($CH_2$), one or more methine groups (CH), one or more quaternary carbon atoms, or a group formed by combination of two or more thereof; k represents 0 or 1; $L^1$ to $L^3$ each represents —$CH_2$—, —$OCH_2$—, —$CH_2O$—, or —C(=O)—; Z represents an oxygen atom or NH; m represents an integer of 2 to 4; n represents an integer of 1 to 10; t represents an integer of 2 to 10; and q represents an integer of 1 to 30, provided that a plurality of $L^1$ to $L^3$, k, $W^1$, $W^2$, Z, m, n, and q each present in the formula may be the same as or different from each other.

34. A fluorine-based compound represented by any of following formulae (1g) to (1l):

(1g)

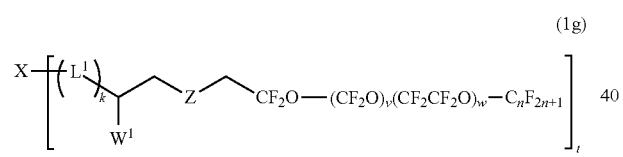

(1h)

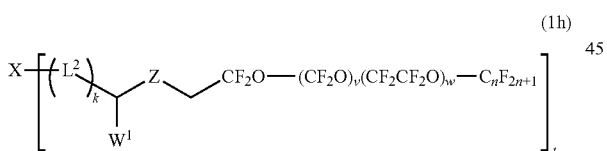

(1i)

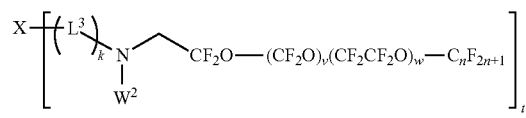

(1j)

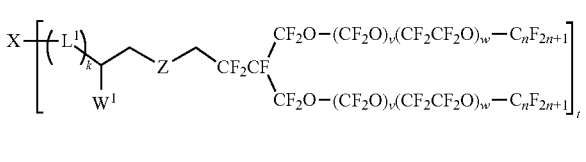

(1k)

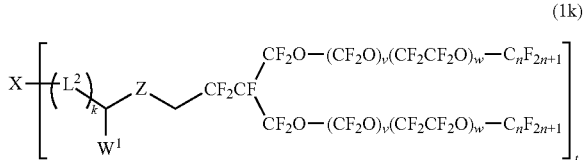

(1l)

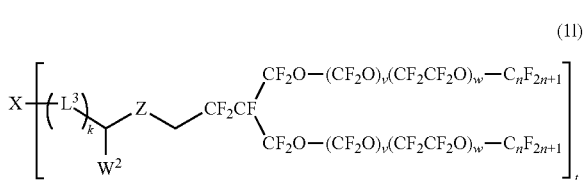

where in the formulae, X represents a cyclic group which may be substituted; $W^1$ and $W^2$ each represents a polar group, or a group having a polar group including one or more polar groups, one or more methylene groups ($CH_2$), one or more methine groups (CH), one or more quaternary carbon atoms, or a group formed by combination of two or more thereof; k represents 0 or 1; $L^1$ to $L^3$ each represents —$CH_2$—, —$OCH_2$—, —$CH_2O$—, or —C(=O)—; Z represents an oxygen atom or NH; v represents an integer of 1 to 20; and w represents an integer of 1 to 20, provided that (v+w) is an integer of 1 to 30; the binding sequence of ($CF_2O$) and ($CF_2CF_2O$) is not limited; n represents an integer of 1 to 10; and t represents an integer of 2 to 10, provided that a plurality of $L^1$ to $L^3$, k, $W^1$, $W^2$, Z, v, w, and n each present in the formula may be the same as or different from each other.

35. A fluorine-based compound of any of the following L-1 to L-14:

L-1

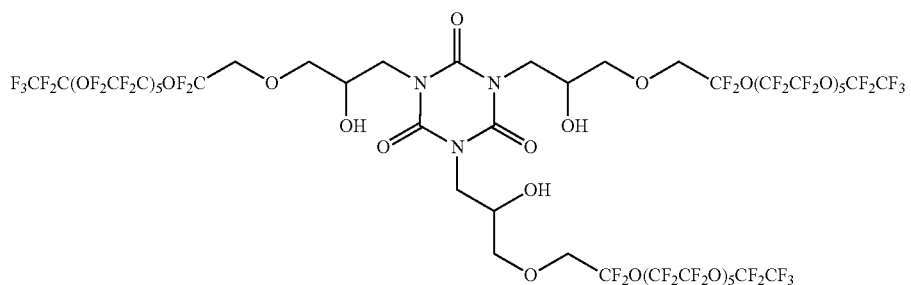

-continued
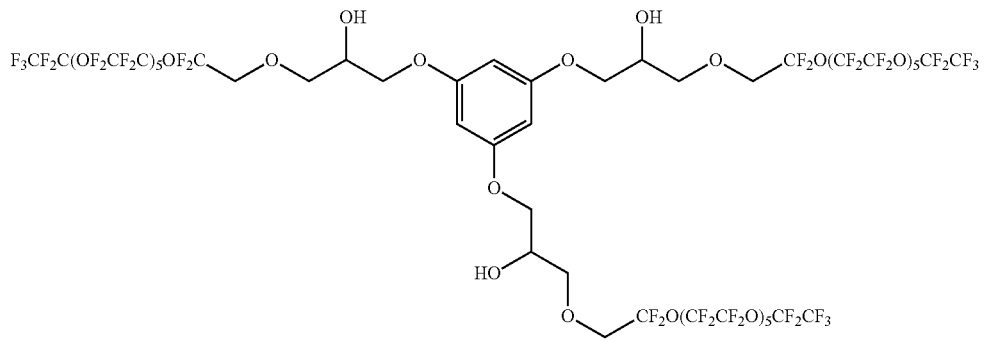
L-2
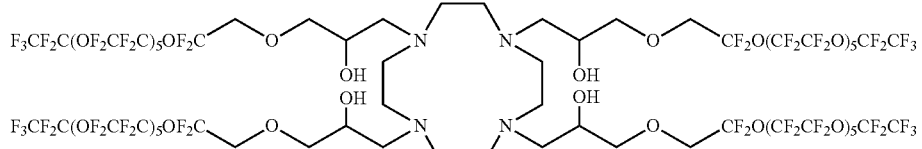
L-3
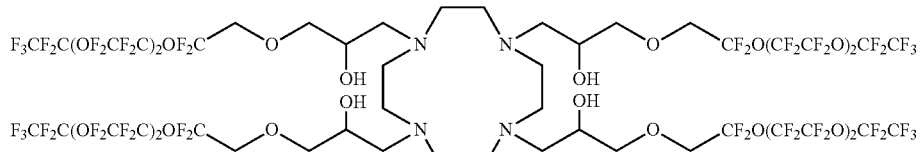
L-4
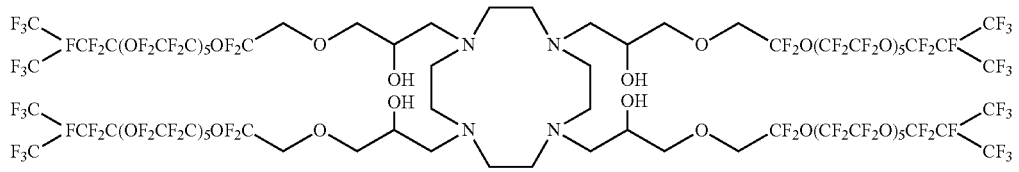
L-5
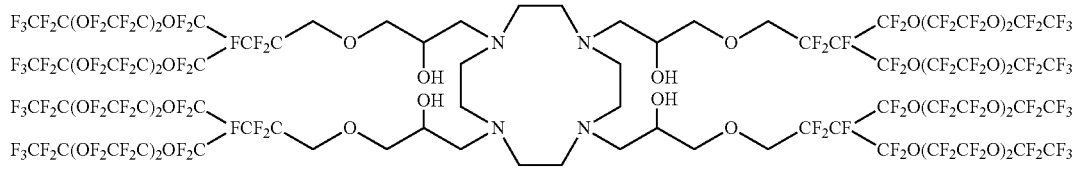
L-6
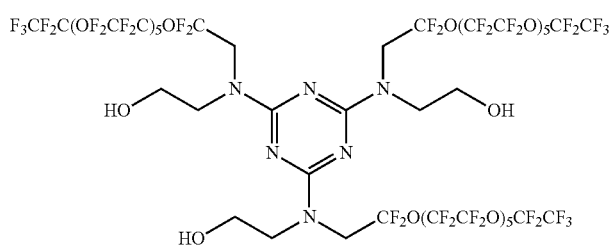
L-7
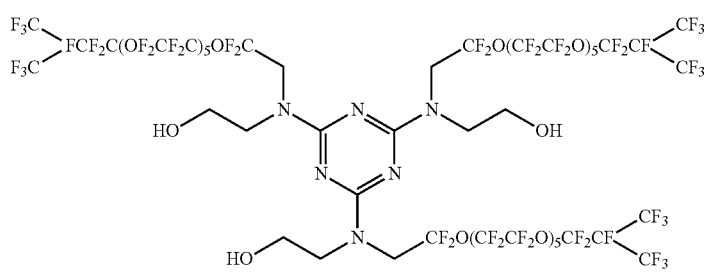
L-8

-continued
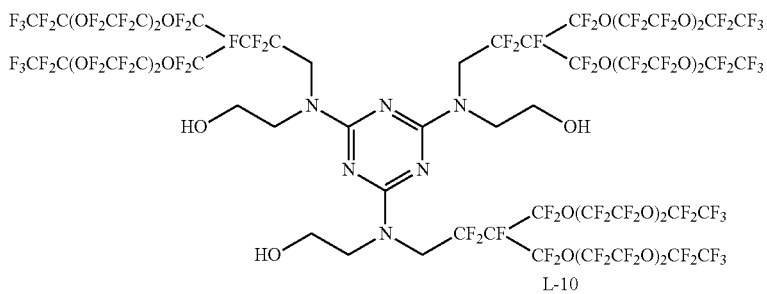
L-9
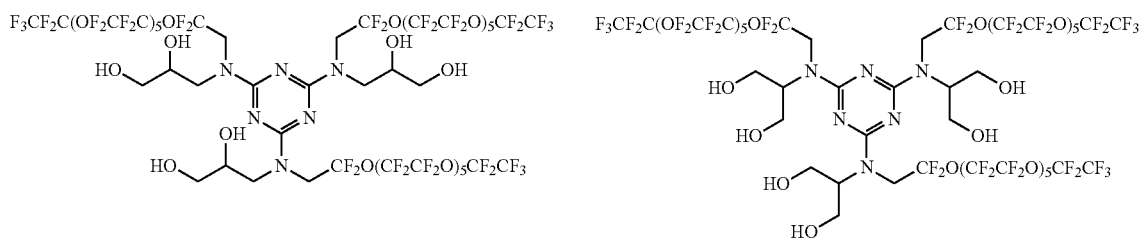
L-10
L-11
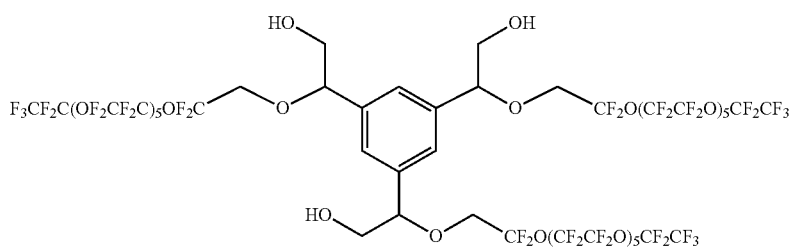
L-12
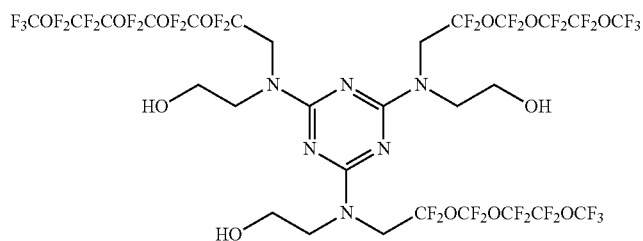
L-13
L-14
where, in the formula (L-14), m represents an integer of 1 to 20, n represents an integer of 1 to 20, provided that (m+n) is an integer of 1 to 30 and the binding sequence of $(CF_2O)$ and $(CF_2CF_2O)$ is not limited.
* * * * *